United States Patent
Yamada et al.

(10) Patent No.: US 9,911,921 B2
(45) Date of Patent: Mar. 6, 2018

(54) ORGANIC COMPOUND AND ORGANIC LIGHT-EMITTING DEVICE

(71) Applicant: CANON KABUSHIKI KAISHA, Tokyo (JP)

(72) Inventors: Naoki Yamada, Inagi (JP); Jun Kamatani, Tokyo (JP); Akihito Saitoh, Gotemba (JP); Yosuke Nishide, Kawasaki (JP); Masanori Muratsubaki, Tokyo (JP); Ryuji Ishii, Yokohama (JP); Koichi Ishige, Yokohama (JP); Takayuki Ito, Kawasaki (JP); Norifumi Kajimoto, Tokyo (JP); Nobutaka Mizuno, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/766,298

(22) PCT Filed: Apr. 3, 2014

(86) PCT No.: PCT/JP2014/060350
§ 371 (c)(1),
(2) Date: Aug. 6, 2015

(87) PCT Pub. No.: WO2014/163211
PCT Pub. Date: Oct. 9, 2014

(65) Prior Publication Data
US 2015/0372238 A1  Dec. 24, 2015

(30) Foreign Application Priority Data

Apr. 3, 2013  (JP) ................ 2013-077439
Apr. 2, 2014  (JP) ................ 2014-076287

(51) Int. Cl.

| | |
|---|---|
| H01L 51/54 | (2006.01) |
| C07C 13/567 | (2006.01) |
| H01L 51/00 | (2006.01) |
| C07C 43/275 | (2006.01) |
| C07C 25/22 | (2006.01) |
| C07C 13/615 | (2006.01) |
| C07C 22/08 | (2006.01) |
| C07C 13/66 | (2006.01) |
| G03G 15/04 | (2006.01) |
| G06F 3/041 | (2006.01) |
| H01L 27/32 | (2006.01) |
| H05B 33/08 | (2006.01) |
| H01L 51/50 | (2006.01) |

(52) U.S. Cl.
CPC ........ *H01L 51/0058* (2013.01); *C07C 13/567* (2013.01); *C07C 13/615* (2013.01); *C07C 13/66* (2013.01); *C07C 22/08* (2013.01); *C07C 25/22* (2013.01); *C07C 43/275* (2013.01); *G03G 15/04063* (2013.01); *G06F 3/0412* (2013.01); *H01L 27/3248* (2013.01); *H01L 51/006* (2013.01); *H01L 51/0052* (2013.01); *H01L 51/0054* (2013.01); *H01L 51/0055* (2013.01); *H01L 51/0059* (2013.01); *H01L 51/0072* (2013.01); *H05B 33/0896* (2013.01); *C07C 2601/14* (2017.05); *C07C 2603/18* (2017.05); *C07C 2603/26* (2017.05); *C07C 2603/40* (2017.05); *C07C 2603/42* (2017.05); *C07C 2603/48* (2017.05); *C07C 2603/50* (2017.05); *C07C 2603/74* (2017.05); *H01L 51/0074* (2013.01); *H01L 51/0085* (2013.01); *H01L 51/5056* (2013.01)

(58) Field of Classification Search
CPC ..................................... C07C 13/567
See application file for complete search history.

(56) References Cited

U.S. PATENT DOCUMENTS 5,989,737 A  * 11/1999  Xie et al. ............... C09K 11/06
                                                   313/502
7,229,702 B2  6/2007  Saitoh et al.
(Continued)

FOREIGN PATENT DOCUMENTS

| JP | 2000-68064 A | 3/2000 |
| JP | 2003-77676 A | 3/2003 |

(Continued)

OTHER PUBLICATIONS

U.S. Appl. No. 14/996,349, filed Jan. 15, 2016, published Jul. 21, 2016 as U.S. 2016/0211467 A1.
International Search Report dated Jul. 8, 2014 issued in PCT/JP2014/060350 (3 pages).
Written Opinion of the International Searching Authority dated Jun. 26, 2014 issued in PCT/JP2014/060350 (6 pages).
Extended European Search Report dated Mar. 15, 2017, in counterpart EP Application No. 14778819.4 (8 pages).

*Primary Examiner* — Marie R. Yamnitzky
(74) *Attorney, Agent, or Firm* — Fitzpatrick, Cella, Harper & Scinto

(57) ABSTRACT

Provided is an organic light-emitting device capable of outputting light with high efficiency and high luminance. The organic light-emitting device includes an anode, a cathode, an emission layer placed between the anode and the cathode, and an organic compound layer placed between the anode and the emission layer, in which the organic compound layer contains the following compound A and compound B: [Compound A] an organic compound free of a nitrogen atom and a metal atom, the compound having $SP^2$ carbon atoms and $SP^3$ carbon atoms, and having a ratio of the number of the $SP^3$ carbon atoms to the number of the $SP^2$ carbon atoms of 40% or more; and [Compound B] a compound having a tertiary amine structure.

20 Claims, 1 Drawing Sheet

(56) References Cited

U.S. PATENT DOCUMENTS

| | | | |
|---|---|---|---|
| 7,361,414 B2 | 4/2008 | Tsuboyama et al. | |
| 7,375,250 B2 | 5/2008 | Saitoh et al. | |
| 7,387,845 B2 | 6/2008 | Saitoh et al. | |
| 7,422,799 B2 | 9/2008 | Mishima et al. | |
| 7,491,450 B2 | 2/2009 | Okinaka et al. | |
| 7,632,577 B2 | 12/2009 | Saitoh et al. | |
| 7,691,491 B2 | 4/2010 | Saitoh et al. | |
| 7,709,104 B2 | 5/2010 | Saitoh et al. | |
| 7,740,958 B2 | 6/2010 | Saitoh et al. | |
| 7,785,719 B2 | 8/2010 | Yamada et al. | |
| 7,923,129 B2 | 4/2011 | Igawa et al. | |
| 7,952,269 B2 | 5/2011 | Okinaka et al. | |
| 7,960,039 B2 | 6/2011 | Abe et al. | |
| 7,976,958 B2 | 7/2011 | Takiguchi et al. | |
| 7,998,597 B2 | 8/2011 | Saitoh et al. | |
| 8,017,774 B2 | 9/2011 | Kamatani et al. | |
| 8,021,767 B2 | 9/2011 | Yamada et al. | |
| 8,283,053 B2 | 10/2012 | Hashimoto et al. | |
| 8,288,018 B2 | 10/2012 | Abe et al. | |
| 8,330,153 B2 | 12/2012 | Ooishi et al. | |
| 8,421,339 B2 | 4/2013 | Nishino et al. | |
| 8,691,398 B2 | 4/2014 | Yamada et al. | |
| 8,790,795 B2 | 7/2014 | Iwawaki et al. | |
| 9,130,173 B2 | 9/2015 | Abe et al. | |
| 9,373,800 B2 | 6/2016 | Kamatani et al. | |
| 2005/0202277 A1 | 9/2005 | Mishima et al. | |
| 2005/0208327 A1* | 9/2005 | Begley et al. | C09K 11/06 428/690 |
| 2007/0111029 A1 | 5/2007 | Yamada et al. | |
| 2008/0166591 A1 | 7/2008 | Yamada et al. | |
| 2009/0039776 A1 | 2/2009 | Yamada et al. | |
| 2009/0091244 A1 | 4/2009 | Negishi et al. | |
| 2009/0102371 A1 | 4/2009 | Hashimoto et al. | |
| 2009/0134788 A1 | 5/2009 | Yamada et al. | |
| 2009/0218938 A1* | 9/2009 | Takeda et al. | H01L 51/5016 313/504 |
| 2010/0327274 A1* | 12/2010 | Okajima et al. | C09K 11/06 257/40 |
| 2010/0327779 A1 | 12/2010 | Nishino et al. | |
| 2011/0300770 A1 | 12/2011 | Fukuda et al. | |
| 2013/0228770 A1 | 9/2013 | Kosuge et al. | |
| 2015/0270493 A1 | 9/2015 | Nishide et al. | |
| 2016/0118607 A1 | 4/2016 | Nishide et al. | |

FOREIGN PATENT DOCUMENTS

| | | |
|---|---|---|
| JP | 2004-277368 A | 10/2004 |
| JP | 2005-294249 A | 10/2005 |
| JP | 2007-314506 A | 12/2007 |
| JP | 2007-314510 A | 12/2007 |
| JP | 2009-170812 A | 7/2009 |
| JP | 2011-8918 A | 1/2011 |
| JP | 2011-9573 A | 1/2011 |

* cited by examiner

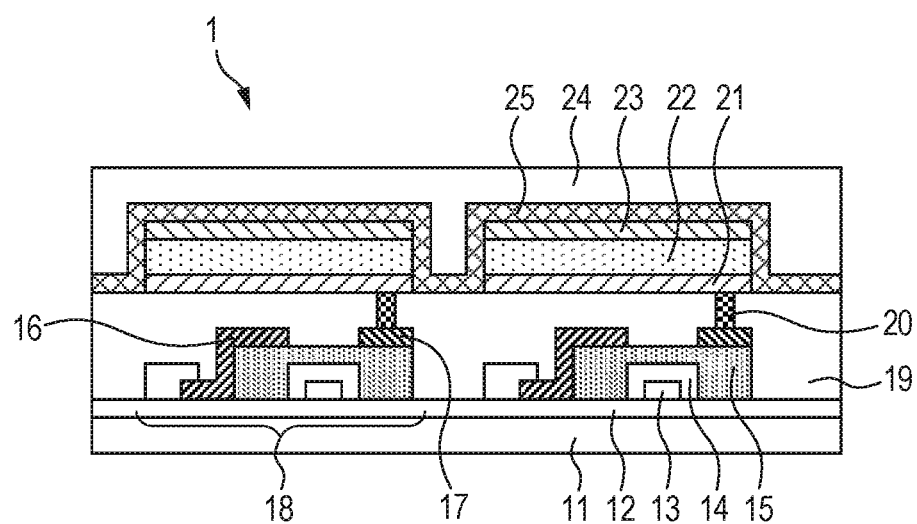

ORGANIC COMPOUND AND ORGANIC LIGHT-EMITTING DEVICE

TECHNICAL FIELD

The present invention relates to an organic compound and an organic light-emitting device using the compound.

BACKGROUND ART

An organic light-emitting device is an electronic device including a pair of electrodes and an organic compound layer placed between the electrodes. An electron and a hole are injected from the pair of electrodes, the electron and the hole recombine in the organic compound layer to produce an exciton of a luminous organic compound, and the organic light-emitting device emits light when the exciton returns to its ground state.

Multiple elements for an improvement in emission efficiency of the organic light-emitting device exist, and one of the elements is to improve charge (hole and electron) injection/transport properties. In addition, the research and development of a material and device construction intended for the improvement of the charge injection/transport properties have heretofore been performed.

Patent Literature 1 proposes that an improvement in hole transport property be achieved by forming a hole transport layer from a mixture of different hole transportable materials. In addition, Patent Literature 2 discloses an organic light-emitting device including a layer obtained by doping a tertiary amine compound with rubrene or an anthracene compound. Further, Patent Literature 3 and Patent Literature 4 propose compounds shown below.

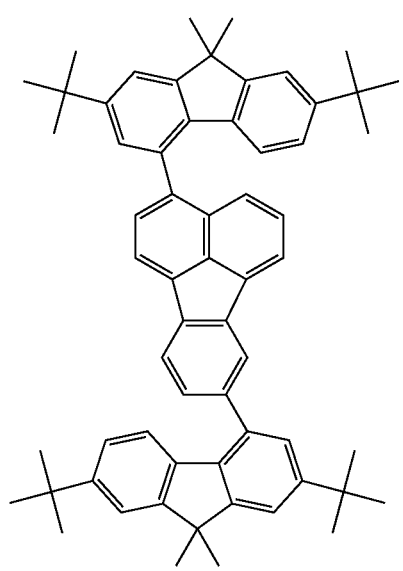

C-1

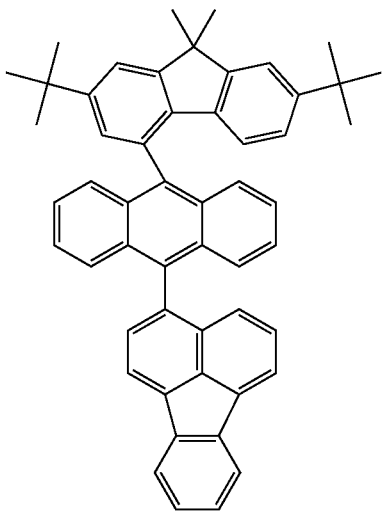

C-2

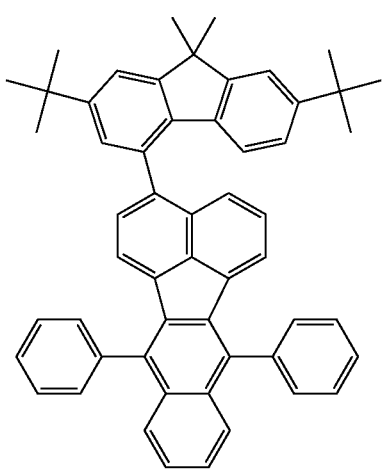

C-3

CITATION LIST

Patent Literature

PTL 1: Japanese Patent Application Laid-Open No. 2000-68064
PTL 2: Japanese Patent Application Laid-Open No. 2003-77676
PTL 3: Japanese Patent Application Laid-Open No. 2007-314510
PTL 4: Japanese Patent Application Laid-Open No. 2007-314506

SUMMARY OF INVENTION

Technical Problem

The present invention has been made to solve the problems and an object of the present invention is to provide an organic light-emitting device capable of outputting light with high efficiency and high luminance.

Solution to Problem

An organic light-emitting device according to one embodiment of the present invention includes: an anode; a cathode; an emission layer placed between the anode and the cathode; and an organic compound layer placed between the anode and the emission layer, wherein the organic compound layer contains the following compound A and compound B:

[Compound A] an organic compound free of a nitrogen atom and a metal atom, the compound having $SP^2$ carbon atoms and $SP^3$ carbon atoms, and having a ratio of the number of the $SP^3$ carbon atoms to the number of the $SP^2$ carbon atoms of 40% or more; and

[Compound B] a compound having a tertiary amine structure.

Advantageous Effects of Invention

According to one embodiment of the present invention, it is possible to provide the organic light-emitting device that outputs light with high efficiency and high luminance. It should be noted that the organic compound of the present invention does not cause association between its molecules and has a wide band gap in a film.

Further features of the present invention will become apparent from the following description of exemplary embodiments with reference to the attached drawings.

BRIEF DESCRIPTION OF DRAWINGS

The FIGURE is a schematic sectional view of a display apparatus including an organic light-emitting device and a switching device connected to the organic light-emitting device.

DESCRIPTION OF EMBODIMENTS

Hereinafter, the present invention is described in detail.
(1) Organic Light-Emitting Device First, an organic light-emitting device of the present invention is described. The organic light-emitting device of the present invention includes: an anode; a cathode; an emission layer placed between the anode and the cathode; and an organic compound layer placed between the anode and the emission layer.

In the present invention, the organic compound layer contains the following compound A and compound B:
[Compound A] an aromatic hydrocarbon compound having $SP^2$ carbon atoms and $SP^3$ carbon atoms, and having a ratio of the number of the $SP^3$ carbon atoms to the number of the $SP^2$ carbon atoms of 40% or more; and
[Compound B] a compound having a tertiary amine structure.

In the present invention, specific constructions of the organic light-emitting device include at least the following constructions (A) to (C).
(A) (Substrate/) anode/hole transport layer/emission layer/electron transport layer/cathode
(B) (Substrate/) anode/hole injection layer/hole transport layer/emission layer/electron transport layer/cathode
(C) (Substrate/) anode/hole transport layer/emission layer/hole•exciton-blocking layer/electron transport layer/cathode It should be noted that the present invention is not limited to the aspects (A) to (C). In particular, for example, the following aspects (D) and (E) can also be included in the specific constructions of the organic light-emitting device depending on the compound A in the organic compound layer.

(D) (Substrate/) anode/emission layer/cathode
(E) (Substrate/) anode/hole transport layer/electron transport layer/cathode.

It should be noted that specific examples of the compound A capable of adopting not only the aspects (A) to (C) but also the aspects (D) and (E) are described later. In addition, in the case of the construction (E), an interface between the hole transport layer and the electron transport layer emits light.

In the present invention, the following may be adopted: the cathode constituting the organic light-emitting device is formed on the substrate as an electrode close to the substrate before the respective layers are formed.

In the present invention, the organic compound layer incorporated into the organic light-emitting device as a layer different from the emission layer is a layer formed between the anode and the emission layer as described above. At this time, the layer construction of the organic compound layer is not limited to a single layer and may be a laminate formed of multiple layers. In the present invention, the organic compound layer in the organic light-emitting device is preferably a layer having a function of transporting a hole, and is specifically a hole injection layer, a hole transport layer, or a laminate obtained by laminating a hole injection layer and a hole transport layer.

Here, the $SP^2$ carbon atoms in the compound A are carbon atoms for forming an unsaturated carbon-carbon bond (C=C) and are carbon atoms constituting mainly the main skeleton of the aromatic hydrocarbon compound. In addition, the $SP^3$ carbon atoms in the compound A are carbon atoms for forming a saturated carbon-carbon bond (C—C) and are carbon atoms constituting mainly an alkyl group bonded to the main skeleton of the aromatic hydrocarbon compound.

In the present invention, the compound A is preferably a compound represented by the following general formula [1] or [2].

$$Z_1\text{-}(Ar_1)_n \qquad [1]$$

$$Ar_2\text{---}Ar_3 \qquad [2]$$

In the general formula [1], $Z_1$ represents an aryl group (aromatic hydrocarbon group), an aliphatic condensed polycyclic group, a carbon atom, or an oxygen atom.

Examples of the aryl group represented by $Z_1$ include: a monovalent aryl group such as a phenyl group, a naphthyl group, a pentalenyl group, an indenyl group, an azulenyl group, an anthryl group, a pyrenyl group, an indacenyl group, an acenaphthenyl group, a phenanthryl group, a phenalenyl group, a fluoranthenyl group, an acephenanthryl group, an aceanthryl group, a triphenylenyl group, a chrysenyl group, a naphthacenyl group, a perylenyl group, a pentacenyl group, a biphenyl group, a terphenyl group, or a fluorenyl group; and a 2- to 6-valent aryl group derived from the monovalent aryl group (that is, a 2- to 6-valent aryl group obtained by removing 1 to 5 hydrogen atoms from the monovalent aryl group).

Examples of the aliphatic condensed polycyclic group represented by $Z_1$ include ring structures listed below.

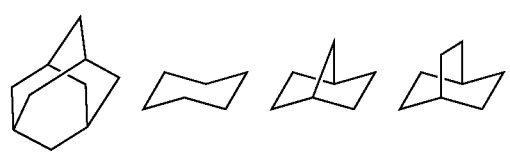

It should be noted that the substituent (aryl group, aliphatic condensed polycyclic group, carbon atom, or oxygen atom) represented by $Z_1$ may further have: an alkyl group such as a methyl group, an ethyl group, an n-propyl group, an isopropyl group, an n-butyl group, a tert-butyl group, a sec-butyl group, an octyl group, a 1-adamantyl group, a 2-adamantyl group, a cyclohexyl group, a cyclopentyl group, or a cyclohexylmethyl group; an alkoxy group such as a methoxy group, an ethoxy group, an isopropoxy group, an n-propoxy group, a sec-butoxy group, a tert-butoxy group, or an octoxy group; an aryl group such as a phenyl group or a phenyl group having an alkyl group; or a halogen atom such as chlorine, bromine, or fluorine. Here, when the aryl group further has an alkyl group, the alkyl group is preferably an alkyl group having 10 or less carbon atoms such as an isopropyl group, an n-propyl group, an n-butyl group, a sec-butyl group, a tert-butyl group, an isoamyl group, an adamantyl group, a cyclohexyl group, a cyclopentyl group, or a cyclohexylmethyl group. Any such substituent promotes the lengthening of the lifetime of the organic light-emitting device because the substituent has good heat stability, plays a considerable role in preventing molecular association in a film, and suppresses the crystallization of the film. Of those, a branched alkyl group such as an isopropyl group, a tert-butyl group, an isoamyl group, an adamantyl group, a cyclohexyl group, a cyclopentyl group, or a cyclohexylmethyl group is more preferred. The presence of any such substituent improves the heat stability of the compound itself. Here, when the aryl group further has an alkoxy group, the aryl group is preferably substituted with an alkoxy group having 10 or less carbon atoms such as an isopropoxy group, an n-propoxy group, a sec-butoxy group, or a tert-butoxy group as the alkoxy group, and an alkoxy group having a branched alkyl group such as an isopropoxy group, a sec-butoxy group, or a tert-butoxy group is more preferred. In addition, when the aryl group further has a halogen atom, the halogen atom is preferably fluorine.

In the general formula [1], $Ar_1$ represents an aryl group, an aliphatic condensed polycyclic group, a carbon atom, or an oxygen atom. Specific examples of the aryl group and aliphatic condensed polycyclic group each represented by $Ar_1$ are the same as the specific examples of the aryl group and aliphatic condensed polycyclic group each represented by $Z_1$. In addition, when $Ar_1$ represents an aryl group, the aryl group may further have a substituent and specific examples of the substituent are the same as the specific examples of the substituent which the aryl group represented by $Z_1$ may further have. In the general formula [1], $Ar_1$ preferably represents a phenyl group having an alkyl group, a fluorenyl group having an alkyl group, a biphenyl group having an alkyl group, or a naphthyl group having an alkyl group.

In the general formula [1], n represents an integer of 1 to 6, provided that when $Z_1$ represents a carbon atom, n represents an integer of 1 to 4, and when $Z_1$ represents an oxygen atom, n represents 1 or 2. When n represents 2 or more, structures $Ar_1$'s in parentheses may be identical to or different from each other.

In the general formula [2], $Ar_2$ and $Ar_3$ each represent an aryl group or an aliphatic condensed polycyclic group. Specific examples of the aryl group and aliphatic condensed polycyclic group represented by $Ar_2$ and $Ar_3$ are the same as the specific examples of the aryl group and aliphatic condensed polycyclic group each represented by $Z_1$ in the formula [1]. In addition, when any one of $Ar_2$ and $Ar_3$ represents an aryl group, the aryl group may further have a substituent and specific examples of the substituent are the same as the specific examples of the substituent which the aryl group represented by $Z_1$ in the formula [1] may further have. The substituent represented by $Ar_2$ or $Ar_3$ in the general formula [2] is preferably a phenyl group having an alkyl group, a fluorenyl group having an alkyl group, a biphenyl group having an alkyl group, or a naphthyl group having an alkyl group.

Next, the compound B is described. The tertiary amine structure of the compound B refers to a structure formed of a nitrogen atom and three kinds of substituents except hydrogen bonded to the nitrogen atom. The compound B is a compound containing one or more tertiary amine structures of this type. In addition, the compound may be a low-molecular weight compound or may be a high-molecular weight compound.

When the compound having a tertiary amine structure serving as the compound B is, for example, a low-molecular weight compound, the compound is any one of the compounds listed in the following general formulae [11] to [17].

General formula [11]

General formula [12]

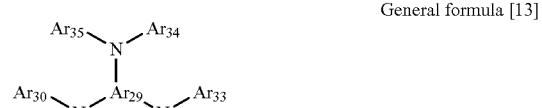

General formula [13]

General formula [14]

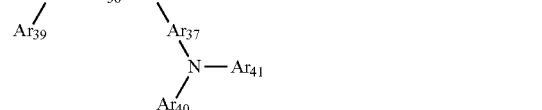

General formula [15]

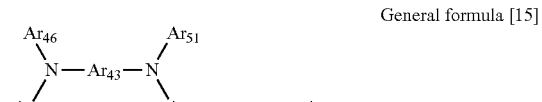

General formula [16]

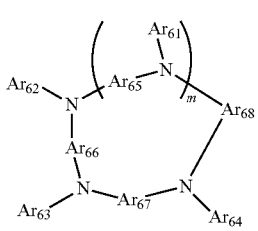

General formula [17]

In the general formulae [11] to [17], $Ar_{21}$ to $Ar_{27}$, $Ar_{30}$ to $Ar_{35}$, $Ar_{38}$ to $Ar_{42}$, $Ar_{46}$ to $Ar_{51}$, $Ar_{55}$ to $Ar_{60}$, and $Ar_{61}$ to $Ar_{64}$ each represent a substituted or unsubstituted, monovalent aryl group, a substituted or unsubstituted, monovalent heterocyclic group, or a substituted or unsubstituted, monovalent alkyl group. In the general formula [17], m represents an integer of 1 to 5.

In addition, when the compound B is a high-molecular weight compound, the compound is, for example, a polymer compound having any one of the general formulae [11] to [17] as a repeating unit.

Examples of the monovalent aryl group include monovalent substituents such as a phenyl group, a naphthyl group, a pentalenyl group, an indenyl group, an azulenyl group, an anthryl group, a pyrenyl group, an indacenyl group, an acenaphthenyl group, a phenanthryl group, a phenalenyl group, a fluoranthenyl group, an acephenanthryl group, an aceanthryl group, a triphenylenyl group, a chrysenyl group, a naphthacenyl group, a perylenyl group, a pantacenyl group, a biphenyl group, a terphenyl group, and a fluorenyl group.

Examples of the monovalent heterocyclic group include monovalent substituents such as a thienyl group, a pyrrolyl group, a pyridyl group, an oxazolyl group, an oxadiazolyl group, a thiazolyl group, a thiadiazolyl group, a terthienyl group, a dibenzothiophenyl group, a dibenzofuryl group, and a phenanthryl group.

Examples of the monovalent alkyl group include monovalent alkyl groups such as a methyl group, an ethyl group, an n-propyl group, an isopropyl group, an n-butyl group, a tert-butyl group, a sec-butyl group, an octyl group, a 1-adamantyl group, and a 2-adamantyl group. Of those, an alkyl group having 4 or less carbon atoms such as a methyl group, an ethyl group, an n-propyl group, an isopropyl group, an n-butyl group, a tert-butyl group, or a sec-butyl group is preferred.

As a substituent that the monovalent aryl group, the monovalent heterocyclic group, or the monovalent alkyl group may have, there are given, for example: an alkyl group such as a methyl group, an ethyl group, an n-propyl group, an isopropyl group, an n-butyl group, a tert-butyl group, a sec-butyl group, an octyl group, a 1-adamantyl group, or a 2-adamantyl group; an aryl group such as a phenyl group, a naphthyl group, a pentalenyl group, an indenyl group, an azulenyl group, an anthryl group, a pyrenyl group, an indacenyl group, an acenaphthenyl group, a phenanthryl group, a phenalenyl group, a fluoranthenyl group, an acephenanthryl group, an aceanthryl group, a triphenylenyl group, a chrysenyl group, a naphthacenyl group, a perylenyl group, a pentacenyl group, a biphenyl group, a terphenyl group, or a fluorenyl group; a heterocyclic group such as a thienyl group, a pyrrolyl group, a pyridyl group, an oxazolyl group, an oxadiazolyl group, a thiazolyl group, a thiadiazolyl group, a terthienyl group, a dibenzothiophenyl group, a dibenzofuryl group, or a phenanthryl group; a substituted amino group such as a dimethylamino group, a diethylamino group, a dibenzylamino group, a diphenylamino group, a ditolylamino group, or a dianisoylamino group; an alkoxy group such as a methoxy group, an ethoxy group, or a propoxy group (preferably an alkoxy group having 4 or less carbon atoms, e.g., a methoxy group, an ethoxy group, a propoxy group, or an n-butoxy group); an aryloxy group such as a phenoxy group; a halogen atom such as fluorine, chlorine, bromine, or iodine (preferably a fluorine atom); and a cyano group.

In the general formulae [11] to [17], $Ar_{28}$, $Ar_{29}$, $Ar_{36}$, $Ar_{37}$, $Ar_{43}$ to $Ar_{45}$, $Ar_{52}$ to $Ar_{54}$, and $Ar_{65}$ to $Ar_{68}$ each represent a substituted or unsubstituted, divalent aryl group, a substituted or unsubstituted, divalent heterocyclic group, or a substituted or unsubstituted, divalent alkyl group.

Examples of the divalent aryl group include divalent substituents derived from a phenyl group, a naphthyl group, a pentalenyl group, an indenyl group, an azulenyl group, an anthryl group, a pyrenyl group, an indacenyl group, an acenaphthenyl group, a phenanthryl group, a phenalenyl group, a fluoranthenyl group, an acephenanthryl group, an aceanthryl group, a triphenylenyl group, a chrysenyl group, a naphthacenyl group, a perylenyl group, a pantacenyl group, a biphenyl group, a terphenyl group, and a fluorenyl group.

Examples of the divalent heterocyclic group include divalent substituents derived from a thienyl group, a pyrrolyl group, a pyridyl group, an oxazolyl group, an oxadiazolyl group, a thiazolyl group, a thiadiazolyl group, a terthienyl group, a dibenzothiophenyl group, a dibenzofuryl group, and a phenanthryl group.

Examples of the divalent alkyl group include divalent alkyl groups derived from a methyl group, an ethyl group, an n-propyl group, an isopropyl group, an n-butyl group, a tert-butyl group, a sec-butyl group, an octyl group, a 1-adamantyl group, and a 2-adamantyl group. Of those, a divalent substituent derived from an alkyl group having 4 or less carbon atoms such as a methyl group, an ethyl group, an n-propyl group, an isopropyl group, an n-butyl group, a tert-butyl group, or a sec-butyl group is preferred.

As a substituent that the aryl group, the heterocyclic group, or the alkyl group may have, there are given, for example: an alkyl group such as a methyl group, an ethyl group, an n-propyl group, an isopropyl group, an n-butyl group, a tert-butyl group, a sec-butyl group, an octyl group, a 1-adamantyl group, or a 2-adamantyl group; an aryl group such as a phenyl group, a naphthyl group, a pentalenyl group, an indenyl group, an azulenyl group, an anthryl group, a pyrenyl group, an indacenyl group, an acenaphthenyl group, a phenanthryl group, a phenalenyl group, a fluoranthenyl group, an acephenanthryl group, an aceanthryl group, a triphenylenyl group, a chrysenyl group, a naphthacenyl group, a perylenyl group, a pentacenyl group, a biphenyl group, a terphenyl group, or a fluorenyl group; a heterocyclic group such as a thienyl group, a pyrrolyl group, a pyridyl group, an oxazolyl group, an oxadiazolyl group, an thiazolyl group, a thiadiazolyl group, a terthienyl group, a dibenzothiophenyl group, a dibenzofuryl group, or a phenanthryl group; a substituted amino group such as a dimethylamino group, a diethylamino group, a dibenzylamino group, a diphenylamino group, a ditolylamino group, or a dianisoylamino group; an alkoxy group such as a methoxy group, an ethoxy group, or a propoxy group (preferably an alkoxy group having 4 or less carbon atoms, e.g., a methoxy group, an ethoxy group, a propoxy group, or an n-butoxy group); an aryloxy group such as a phenoxy group; a halogen atom such as fluorine, chlorine, bromine, or iodine (preferably a fluorine atom); and a cyano group.

In the general formula [11], $Ar_{21}$ to $Ar_{23}$ may be identical to or different from one another. In addition, any one of the combinations of $Ar_{21}$ and $Ar_{22}$, $Ar_{21}$ and $Ar_{23}$, and $Ar_{22}$ and $Ar_{23}$ may wind in a ring (that is, for example, $Ar_{21}$ and $Ar_{22}$ may be bonded to turn into —$Ar_{21}$—$Ar_{22}$—, thereby forming a ring with N) to form a nitrogen-containing heterocyclic skeleton such as a carbazole skeleton.

In the general formula [12], $Ar_{24}$ to $Ar_{27}$ may be identical to or different from one another. In addition, any one of the combinations of $Ar_{24}$ and $Ar_{25}$, and $Ar_{26}$ and $Ar_{27}$ may wind in a ring to form a nitrogen-containing heterocyclic skeleton such as a carbazole skeleton.

In the general formula [13], $Ar_{30}$ to $Ar_{35}$ may be identical to or different from one another. In addition, any one of the combinations of $Ar_{30}$ and $Ar_{31}$, $Ar_{32}$ and $Ar_{33}$, and $Ar_{34}$ and $Ar_{35}$ may wind in a ring to form a nitrogen-containing heterocyclic skeleton such as a carbazole skeleton.

In the general formula [14], $Ar_{36}$ and $Ar_{37}$ may be identical to or different from each other. In addition, in the general formula [14], $Ar_{38}$ to $Ar_{42}$ may be identical to or different from one another. In addition, any one of the combinations of $Ar_{38}$ and $Ar_{39}$, and $Ar_{40}$ and $Ar_{41}$ may wind in a ring to form a nitrogen-containing heterocyclic skeleton such as a carbazole skeleton.

In the general formula [15], $Ar_{43}$ to $Ar_{45}$ may be identical to or different from one another. In addition, in the general formula [15], $Ar_{46}$ to $Ar_{51}$ may be identical to or different from one another. In addition, any one of the combinations of $Ar_{46}$ and $Ar_{47}$, and $Ar_{49}$ and $Ar_{50}$ may wind in a ring to form a nitrogen-containing heterocyclic skeleton such as a carbazole skeleton.

In the general formula [16], $Ar_{52}$ to $Ar_{54}$ may be identical to or different from one another. In addition, in the general formula [16], $Ar_{55}$ to $Ar_{60}$ may be identical to or different from one another. In addition, any one of the combinations of $Ar_{55}$ and $Ar_{56}$, $Ar_{57}$ and $Ar_{58}$, and $Ar_{59}$ and $Ar_{60}$ may wind in a ring to form a nitrogen-containing heterocyclic skeleton such as a carbazole skeleton.

In the general formula [17], $Ar_{61}$ to $Ar_{63}$ may be identical to or different from one another. In addition, in the general formula [17], $Ar_{65}$ to $Ar_{68}$ may be identical to or different from one another. In addition, a compound according to the general formula [17] comprehends a polymer compound having a large number (m value) of repeating units.

The organic light-emitting device of the present invention includes at least one organic compound layer (such as a hole transport layer or an electron-blocking layer) between the anode and the emission layer. In addition, the organic compound layer contains the compound A and the compound B. Thus, the organic light-emitting device of the present invention has good emission efficiency.

The inventors of the present invention have produced an organic light-emitting device having a device construction shown in Table 1 below by using compounds shown below with a view to investigating the operation and effect of the incorporation of the compound A and the compound B into the organic compound layer formed between the anode and the emission layer. It should be noted that multiple compounds different from each other in $SP^3$ carbon atom content were prepared as compounds each serving as the compound A. Details about the foregoing are described below.

<Compound Used as Compound A>

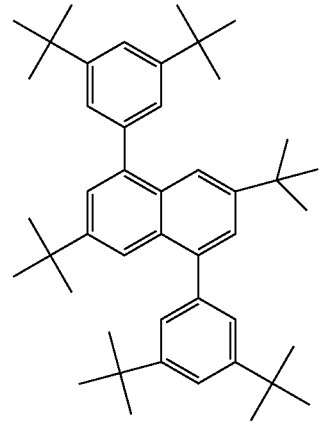

AC-6

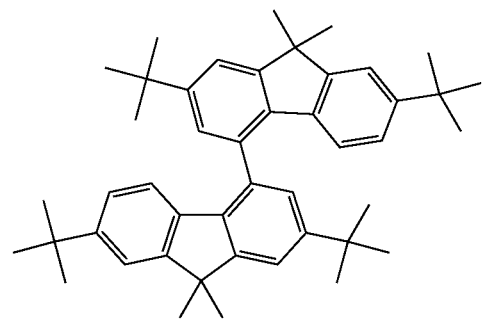

AA-1

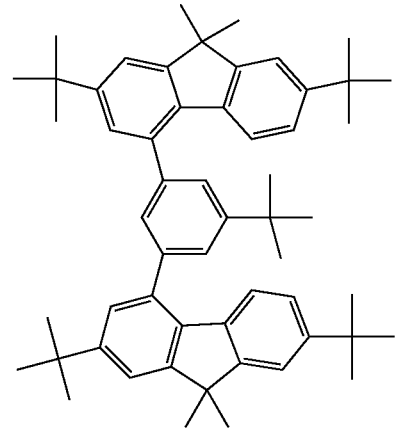

AA-7

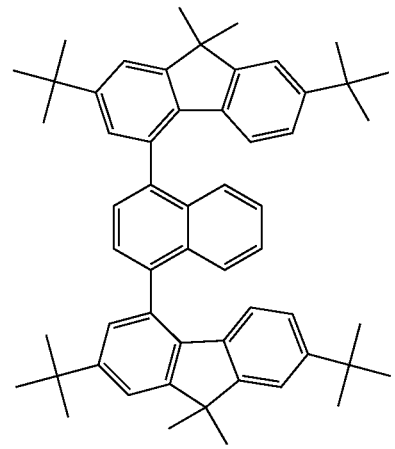

AA-9

-continued
AB-3
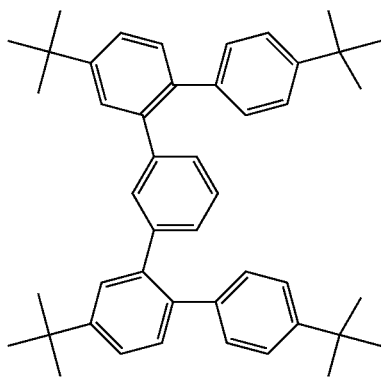
AB-7
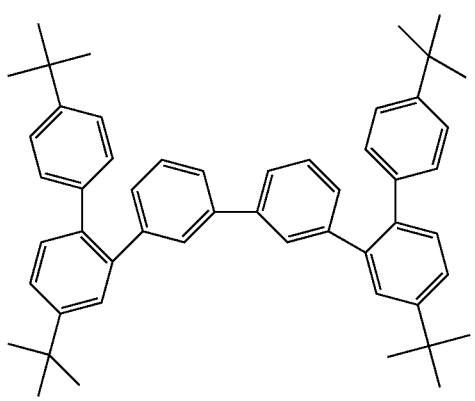
AB-6
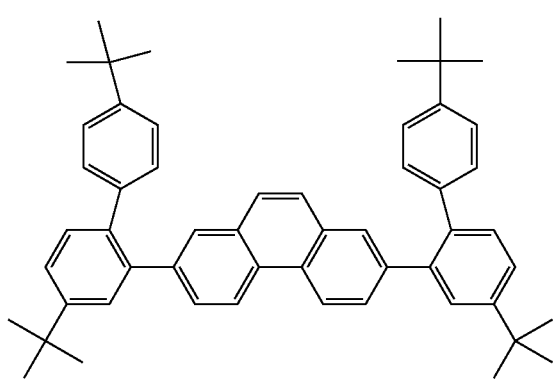
AZ-1
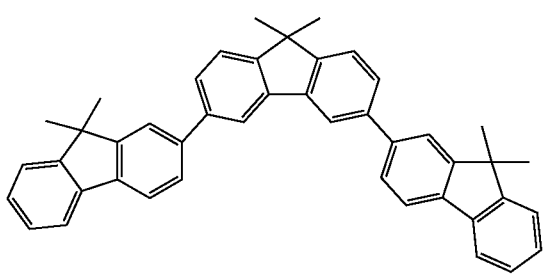
-continued
AZ-2
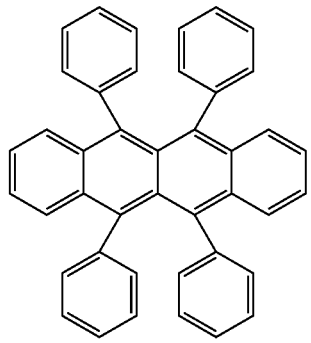
AZ-3
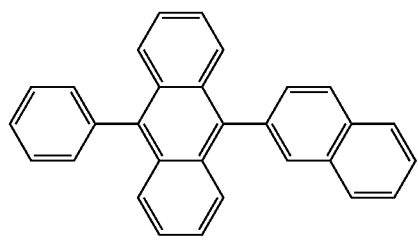
<Compound Used as Compound B>
BC-4
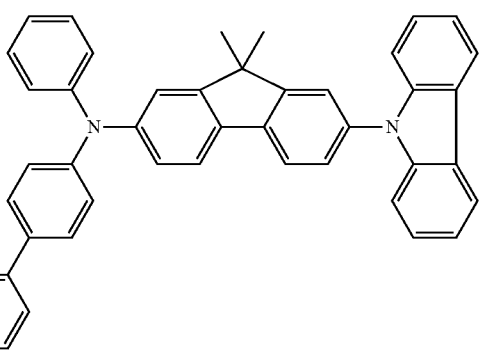
<Others>
c-1
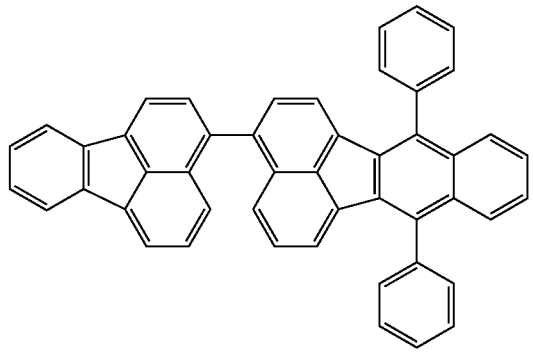

-continued

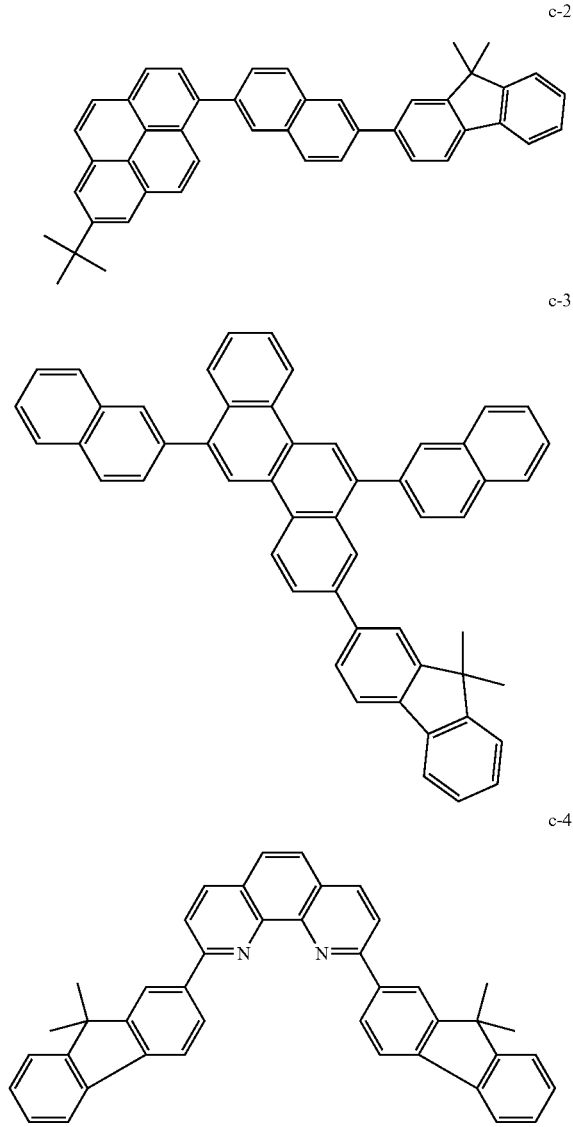

TABLE 1

| | Constituent material | Thickness [nm] |
|---|---|---|
| Anode | ITO | — |
| Organic compound layer | Compound A<br>Compound B (BC-4)<br>(compound A:compound B =<br>2:1 (weight ratio)) | 30 |
| Emission layer | c-2 (host)<br>c-1 (guest)<br>(host:guest = 95:5<br>(weight ratio)) | 20 |
| Hole-blocking layer | c-3 | 40 |
| Electron transport layer | c-4 | 20 |
| First electrode layer (cathode) | LiF | 0.5 |
| Second electrode layer (cathode) | Al | 1,500 |

The produced organic light-emitting device was evaluated for its emission efficiency, external quantum yield, and chromaticity coordinates when caused to emit light under the condition of 2,000 cd/m$^2$.

By the way, the relative ratio (%) of the SP$^3$ carbon atoms in the compound A can be determined from the following equation. It should be noted that the resultant value is rounded off to the nearest integer. [Number of SP$^3$ carbon atoms in compound A]/[number of SP$^2$ carbon atoms in compound A]×100

Table 2 below shows the results of the evaluations of the emission efficiency, the external quantum yield, and the chromaticity coordinates.

TABLE 2

| Compound used as compound A | SP$^3$ carbon atom [relative ratio, %] | Emission efficiency [cd/A] | External quantum yield [%] | Chromaticity coordinates [x, y] |
|---|---|---|---|---|
| AC-6 | 109 | 13.0 | 7.0 | (0.15, 0.26) |
| AA-1 | 92 | 11.7 | 6.5 | (0.16, 0.26) |
| AA-7 | 87 | 11.3 | 6.3 | (0.16, 0.26) |
| AA-9 | 65 | 11.1 | 6.2 | (0.16, 0.26) |
| AB-3 | 53 | 12.3 | 6.9 | (0.16, 0.25) |
| AB-7 | 44 | 11.5 | 6.6 | (0.15, 0.25) |
| AB-6 | 42 | 12.1 | 6.8 | (0.15, 0.25) |
| AZ-1 | 25 | 8.8 | 4.9 | (0.16, 0.24) |
| AZ-2 | 0 | —[Note 1] | | |
| AZ-3 | 0 | 7.8 | 4.3 | (0.15, 0.25) |
| (None) | — | 8.3 | 4.7 | (0.15, 0.25) |

[Note 1]AZ-2 emits light.

It is understood from Table 2 that the emission efficiency is improved by incorporating, into the organic compound layer formed between the anode and the emission layer, a compound having a relative ratio (%) of the SP$^3$ carbon atoms of 40% or more out of the organic compounds each used as the compound A together with the compound B as a hole transportable compound.

The result probably originates from the fact that an operation and effect described below are exhibited.

SP$^3$ carbon atoms generally have the following features (1a-1) and (1a-2):

(1a-1) a feature that an SP$^3$ carbon atom suppresses intermolecular stacking in a film to suppress the contraction of a band gap; and (1a-2) a feature that there is no absorption (derived from a substituent (such as an alkyl group or an aliphatic condensed polycyclic group) constituted of an SP$^3$ carbon atom)) in a visible region.

Meanwhile, SP$^2$ carbon atoms generally have the following features (1b-1) and (1b-2):

(1b-1) a feature that the SP$^2$ carbon atoms each generally have absorption in the visible region (an absorption region shifts to longer wavelengths as the linking number of their aromatic rings increases or the number of their condensed rings increases); and (1b-2) a feature that a band gap contraction effect in which a band gap in a thin-film state narrows as compared with that in a dilute solution state occurs.

It should be noted that the feature (1b-2) is a feature caused by the fact that a stacking interaction is strengthened by the presence of a large amount of electrons delocalized by π-electron systems on a rigid planar structure and SP$^2$ hybrid orbital. In addition, the feature (1b-2) becomes more significant as the number of π-electrons increases.

In view of the foregoing, increasing the relative ratio (%) of (the number of) the SP$^3$ carbon atoms in the compound A to the number of the SP$^2$ carbon atoms in the compound A leads to a preventing effect on the contraction of the band gap of the compound B as a compound containing a tertiary amine structure. Thus, the diffusion and injection of an exciton and electron from the emission layer can be suppressed. As a result, the emission efficiency improves.

In contrast, when a compound having a low (less than 40%) relative ratio of (the number of) $SP^3$ carbon atoms or a relative ratio of zero, e.g., Compound AZ-2 is used as the compound A, the band gap additionally narrows and hence light emission from AZ-2 is observed. Accordingly, an emission spectrum derived from Compound c-1 incorporated into the emission layer as a dopant is not obtained. In addition, when any one of Compounds AZ-1 and AZ-3 is used, the resultant efficiency is substantially the same as that of an organic light-emitting device that does not contain a compound serving as the compound A and hence no improvement is observed.

The matters described above are summarized as follows: the emission efficiency improves as an $SP^3$ carbon atom in an alkyl group or the like of an organic compound corresponding to the compound A is incorporated in a certain amount or more, in other words, the ratio of a substituent (such as an alkyl group) formed of an $SP^3$ carbon atom in a molecule increases. In addition, as shown in Table 2, the improving effect on the emission efficiency appears when the relative ratio (%) of the $SP^3$ carbon atoms is 40% or more. In the present invention, the relative ratio (%) of the number of the $SP^3$ carbon atoms in the compound A to the number of the $SP^2$ carbon atoms in the compound A is preferably 80% or more.

However, it is not preferred to use a compound formed only of an $SP^3$ carbon atom as the compound A because the compound inhibits carrier transport. Accordingly, a carrier-transporting function needs to be secured by incorporating a certain amount of an $SP^2$ carbon atom into the compound.

The structure and substituent of the compound A are not particularly limited as long as the compound has a relative ratio (%) of the $SP^3$ carbon atoms of 40% or more. However, the compound is preferably of a structure free of a nitrogen atom and a metal atom because the difficulty with which the compound interacts with the compound B is preferably high.

In addition, $Ar_2$ and $Z_1$ in the general formula [1], and $Ar_2$ and $Ar_3$ in the general formula [2] are each more preferably of a structure having a wide band gap. Specifically, the structure contains an aryl group such as a phenyl group, a fluorenyl group, a biphenyl group, or a naphthyl group. This is because the structure has suppressing effects on the movement of an exciton and the injection of an electron.

In addition, a mixing ratio between the compound A and compound B in the organic compound layer is not particularly limited. However, a higher ratio of the compound A may improve the emission efficiency and a higher ratio of the compound B may reduce the driving voltage of the device. Accordingly, when compatibility between high efficiency and low-voltage driving is to be achieved, the ratio (mixing ratio, weight base) of the compound B in the organic compound layer is preferably 10 wt % to 90 wt %, more preferably 20 wt % to 70 wt % with reference to the total of the compound A and the compound B.

It should be noted that in the present invention, an assist material that may promote carrier injection may be incorporated into the organic compound layer in addition to the compound A and the compound B.

Specific examples of the compound A are shown below.

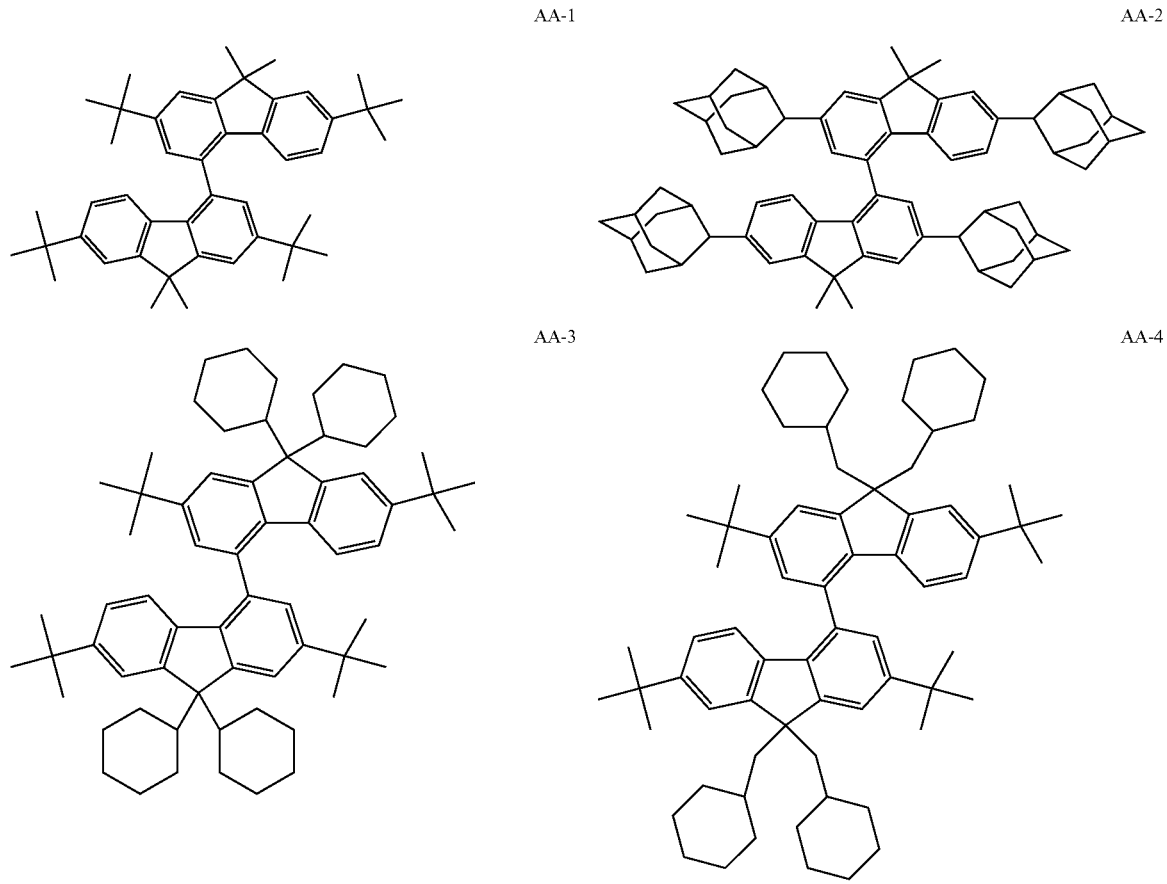

-continued
AA-5
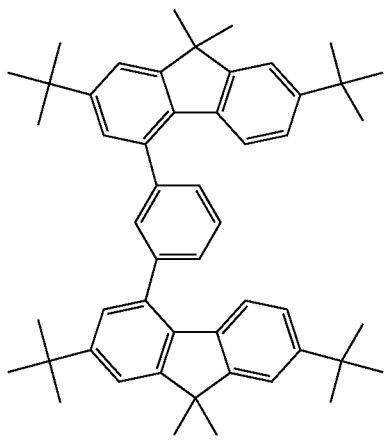
AA-6
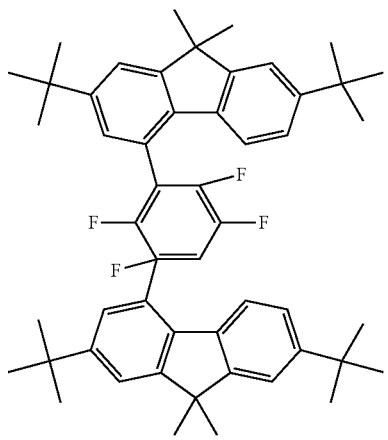
AA-7
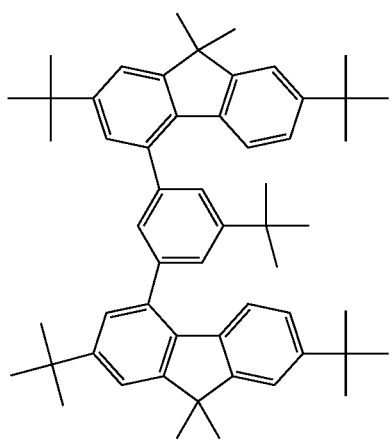
AA-8
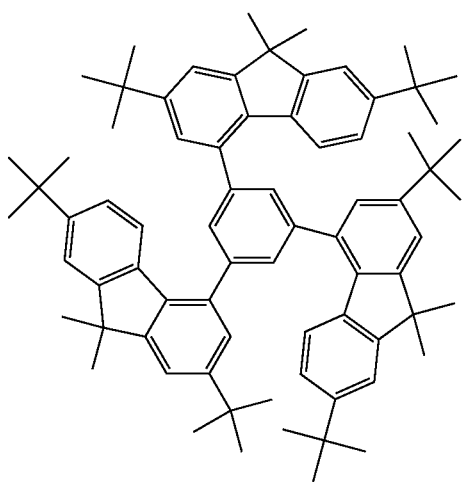
AA-9
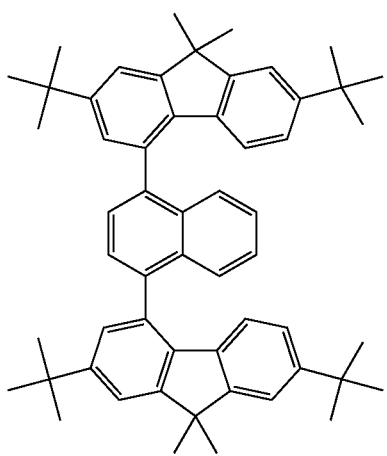
AA-10
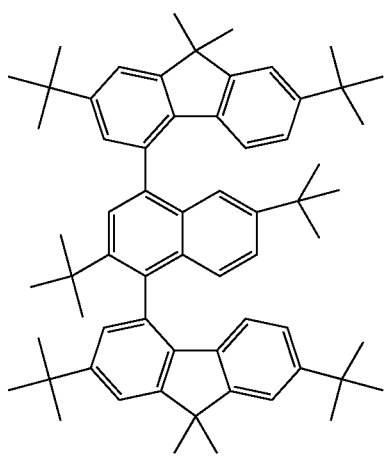

-continued
AA-11
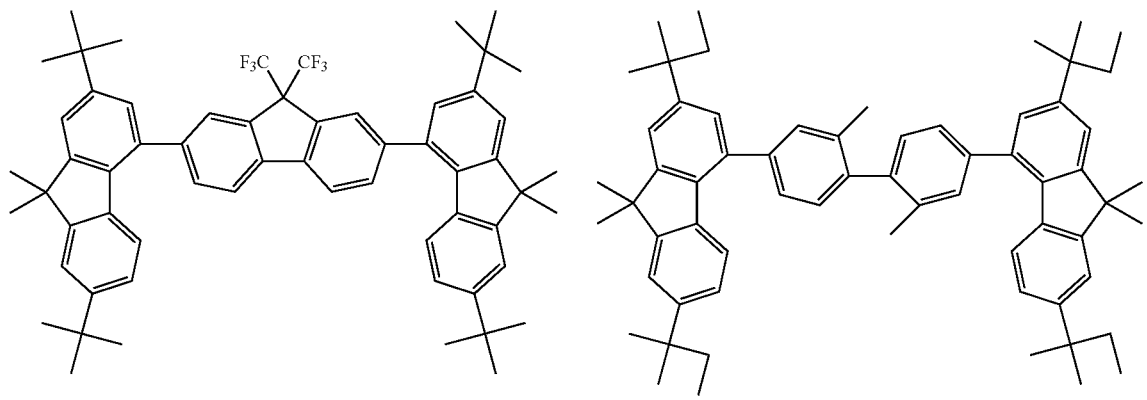
AA-12
AA-13
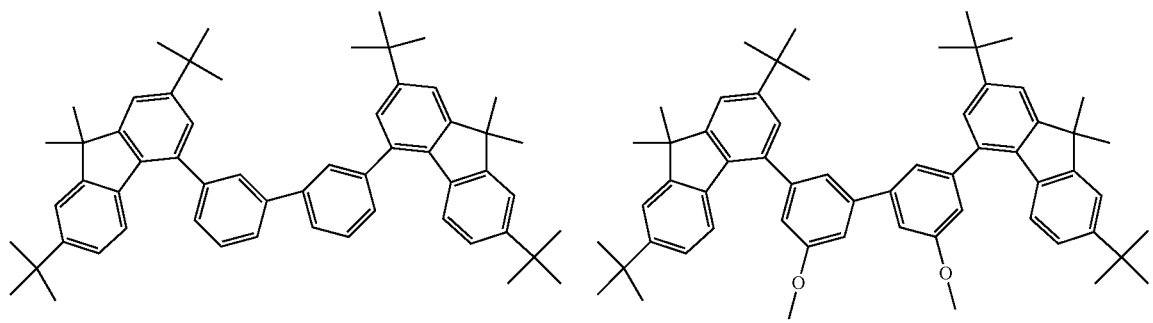
AA-14
AA-15
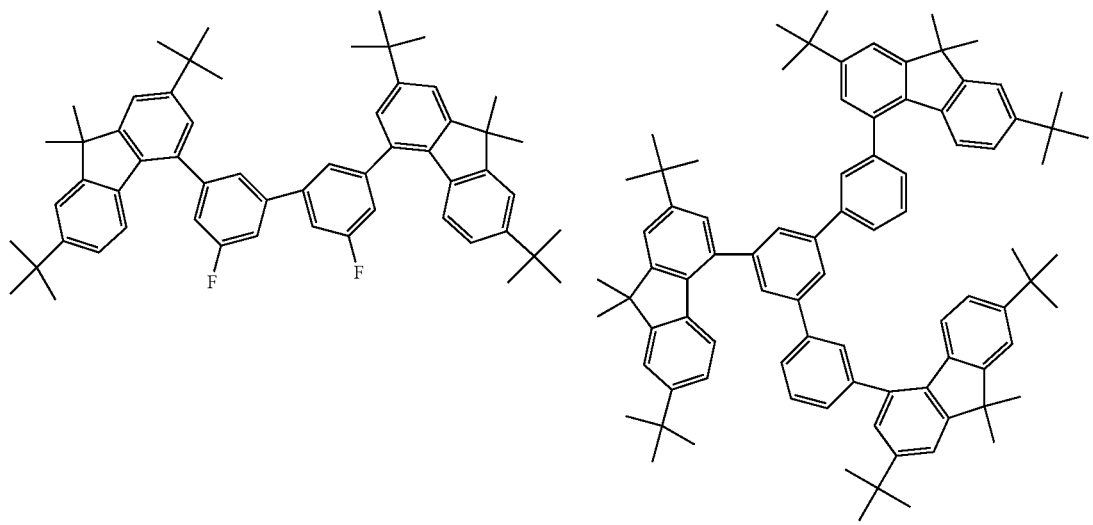
AA-16

-continued
AA-17
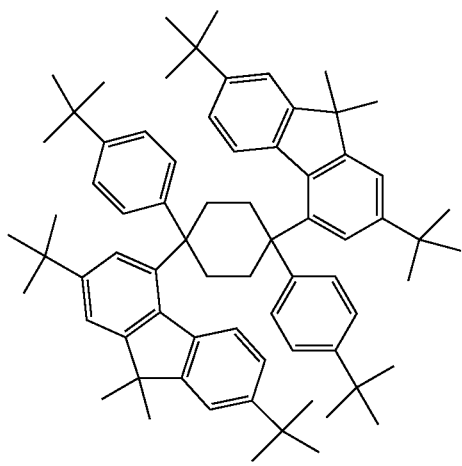
AA-18
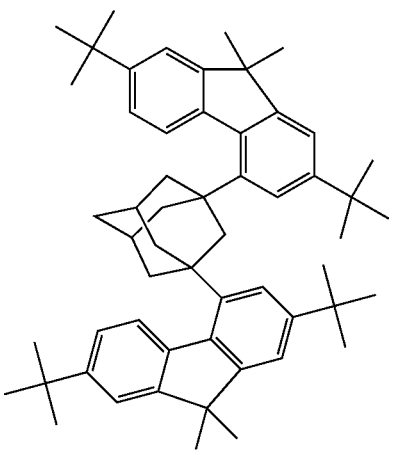
AA-19
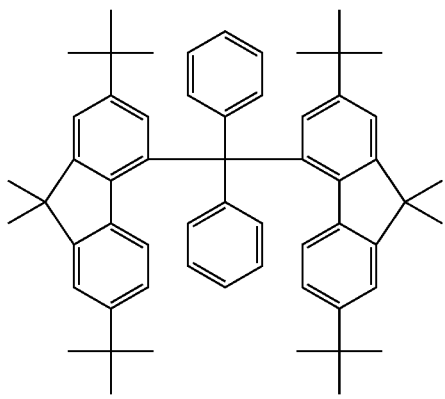
AA-20
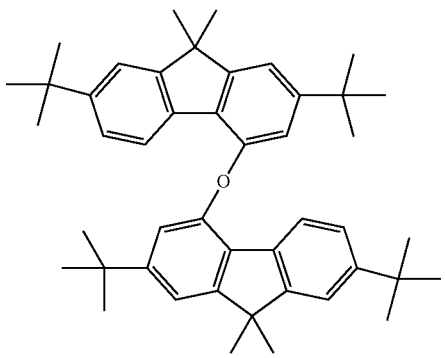
AA-21
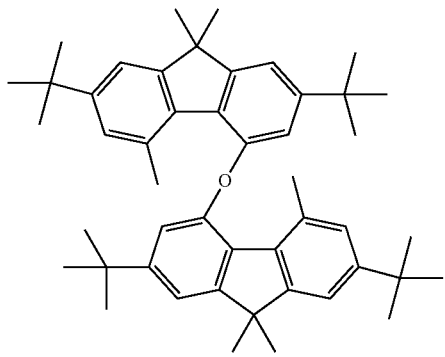
AA-22
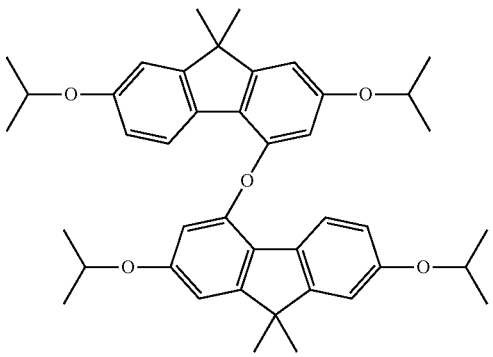
AA-23
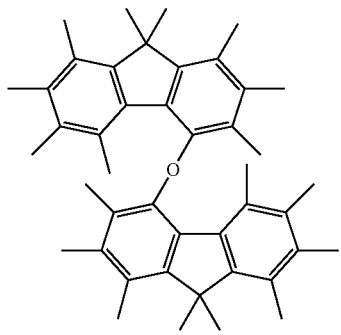
AA-24
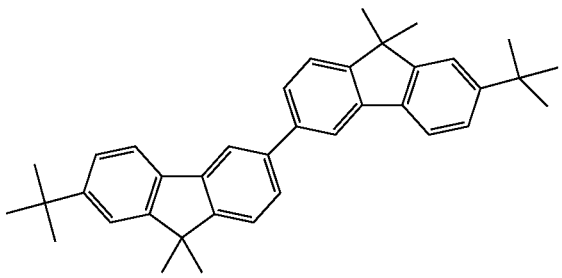

AA-25
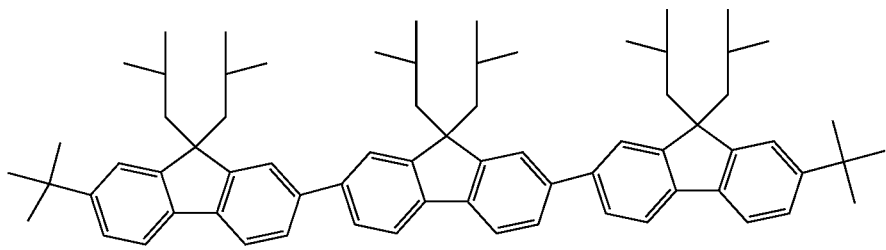
AA-26
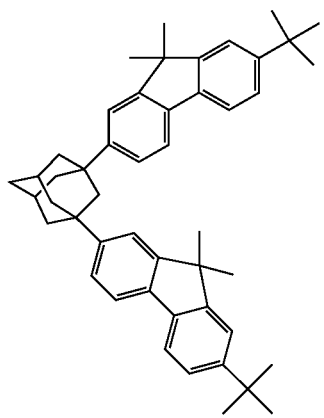
AA-27
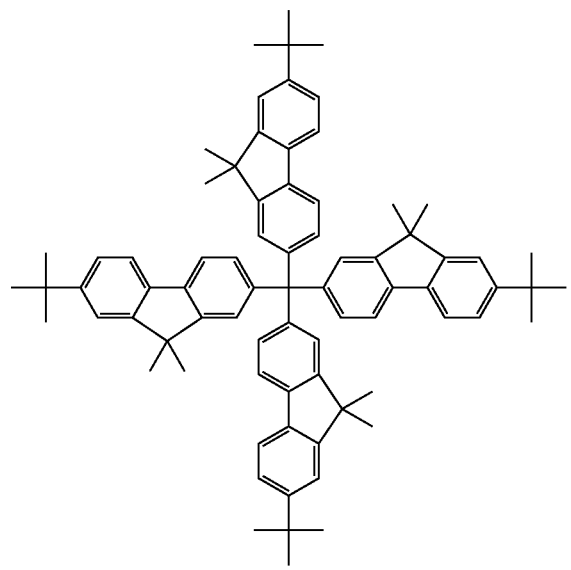
AA-28
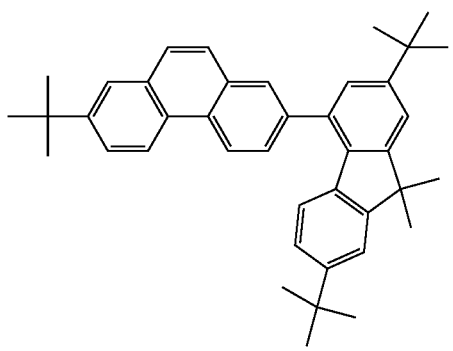
AA-29
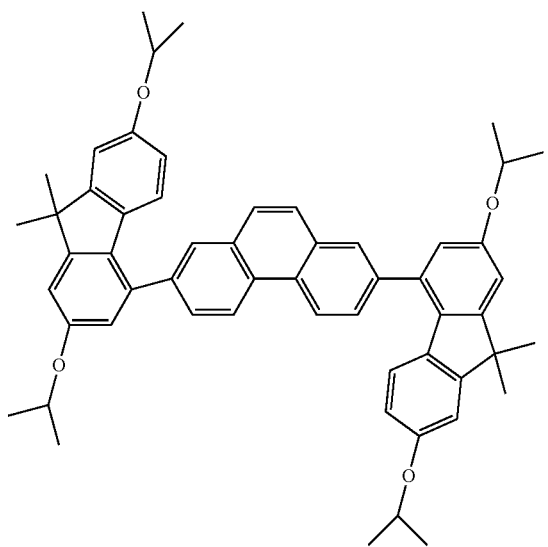

-continued
AA-30
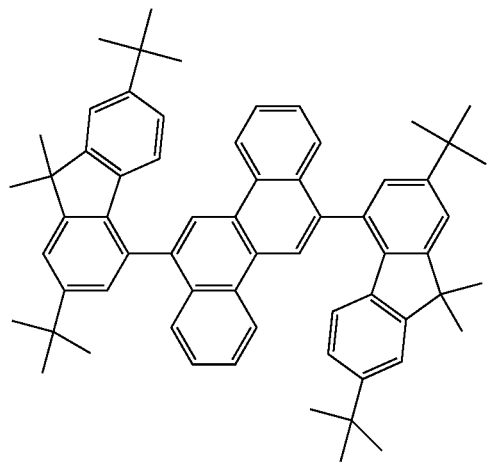
AA-31
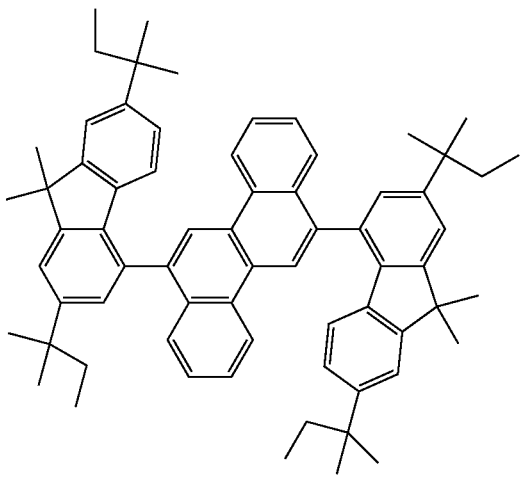
AA-32
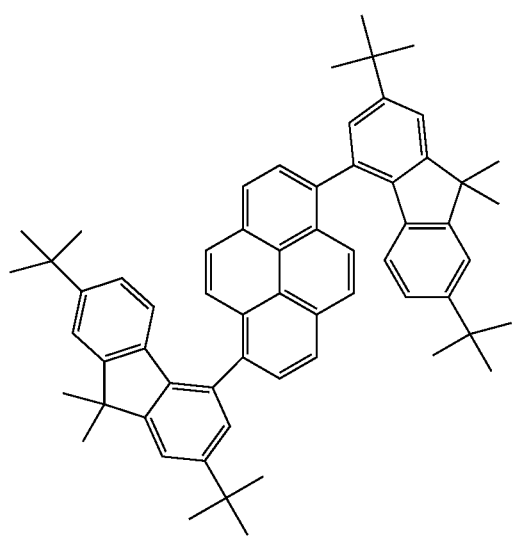
AA-33
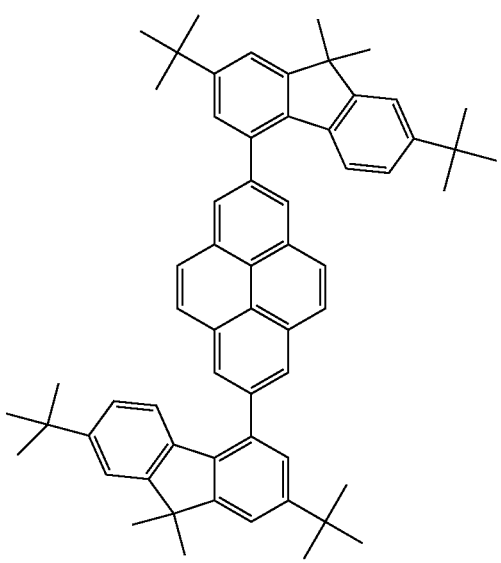
AA-34
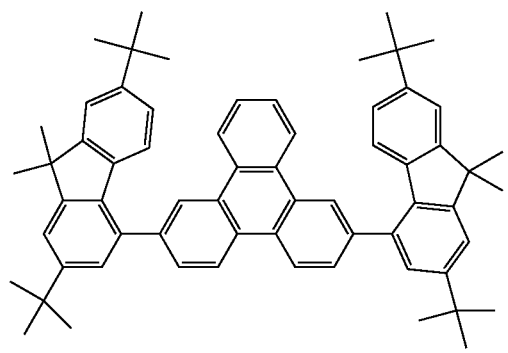
AA-35
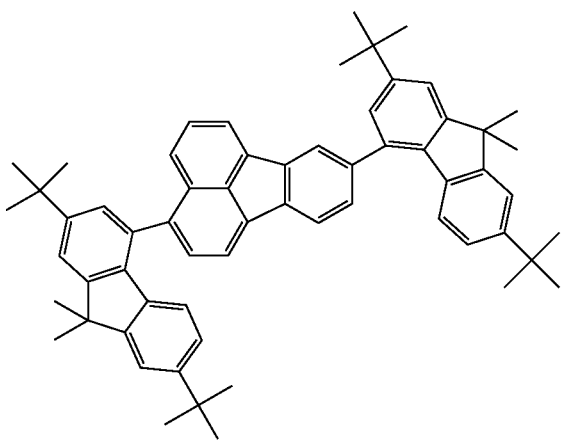

-continued
AB-1
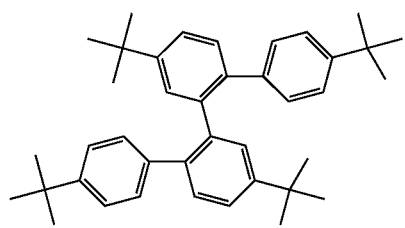
AB-2
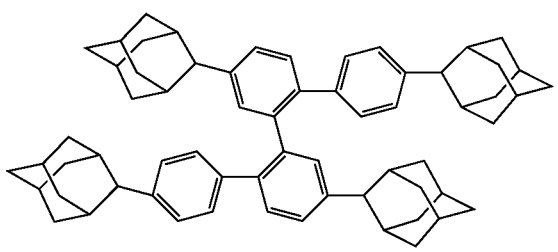
AB-3
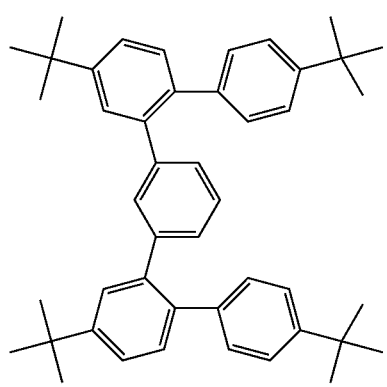
AB-4
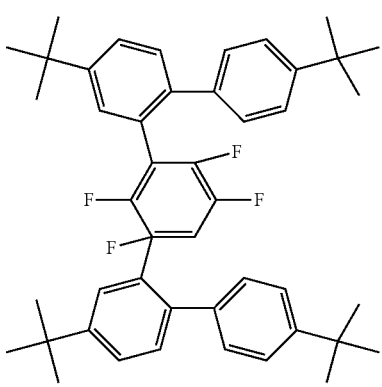
AB-5
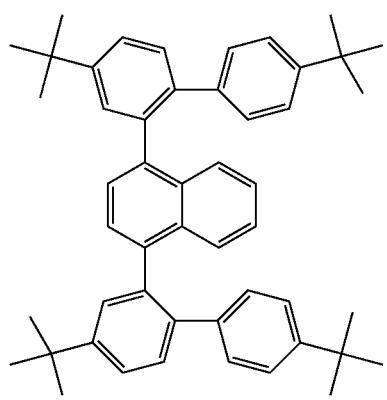
AB-6
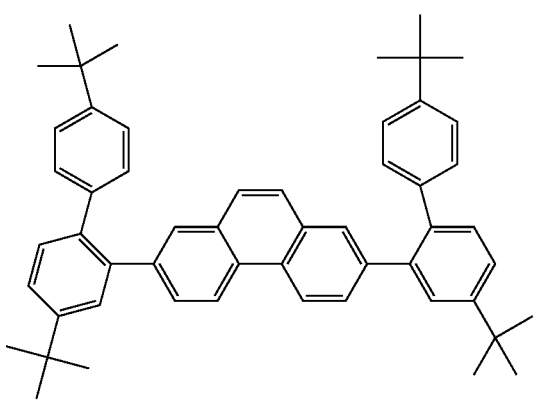
AB-7
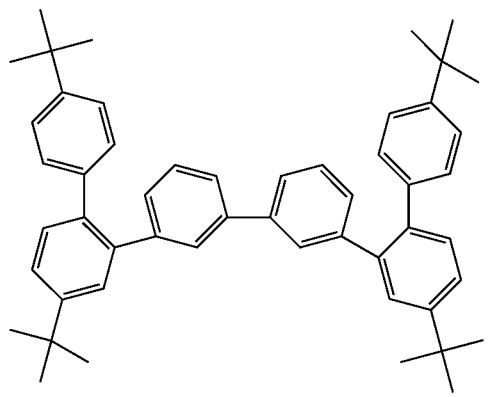
AB-8
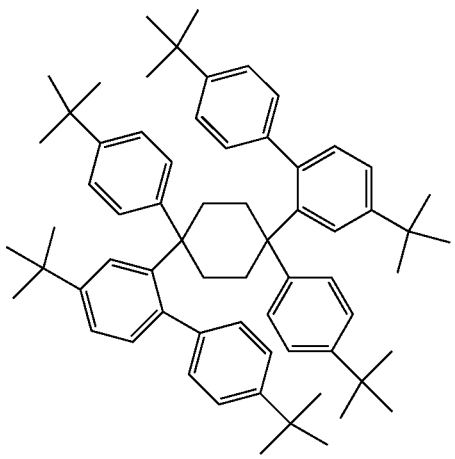

-continued
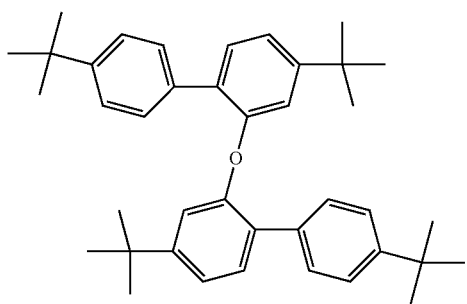
AB-9
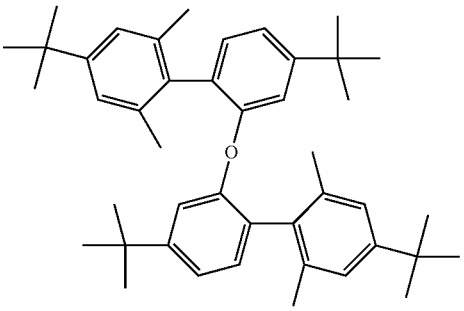
AB-10
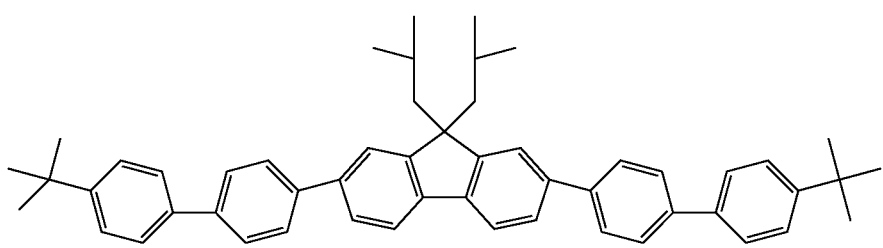
AB-11
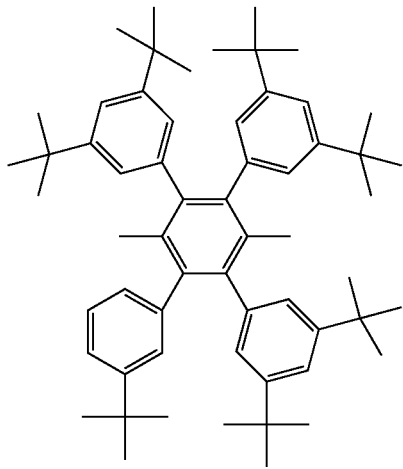
AC-1
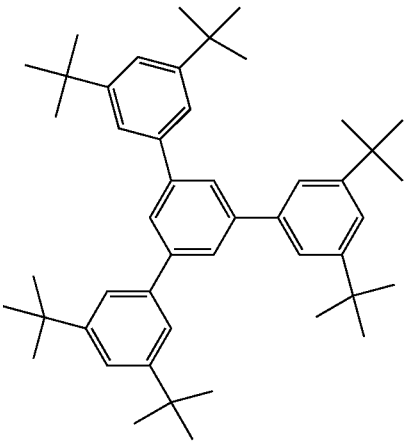
AC-2
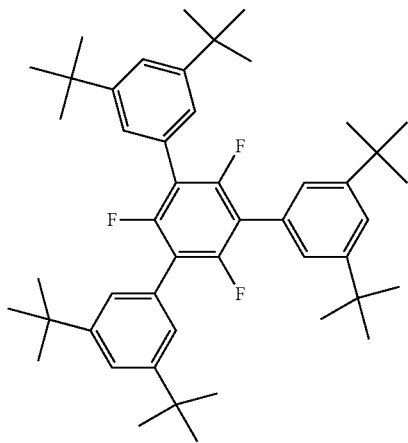
AC-3
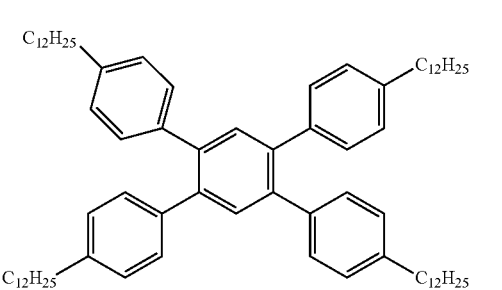
AC-4

-continued
AC-5
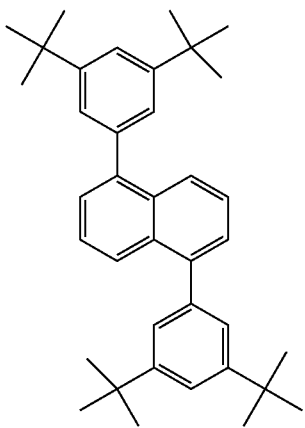
AC-6
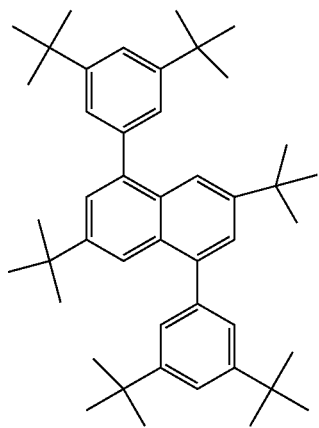
AC-7
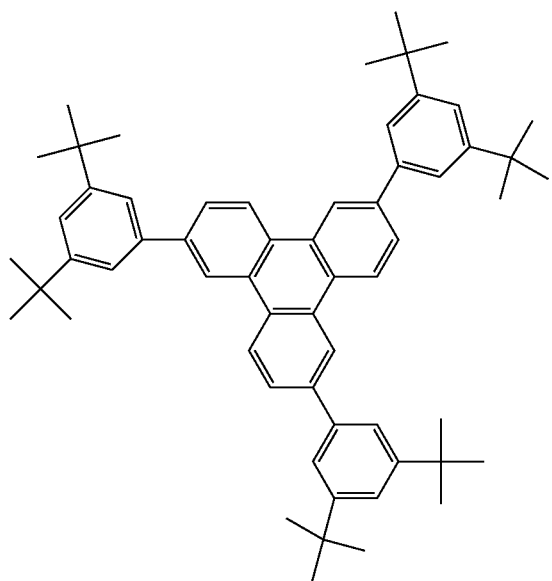
AC-8
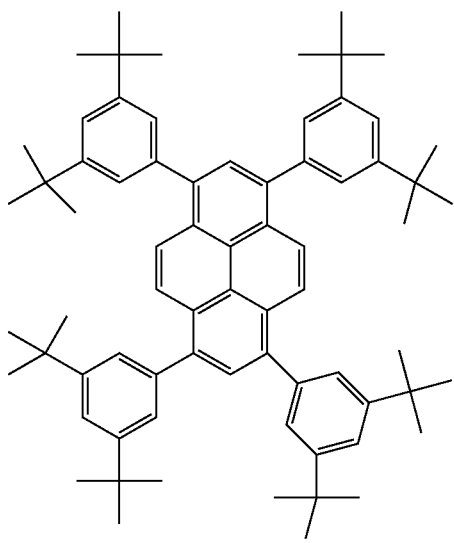
AC-9
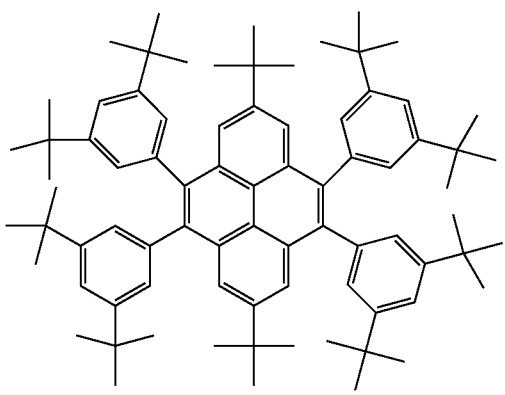
AC-10
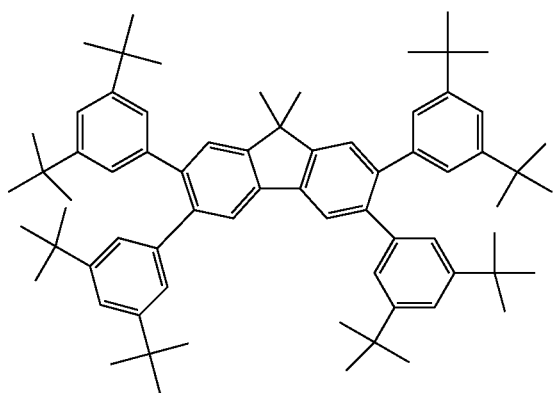

-continued
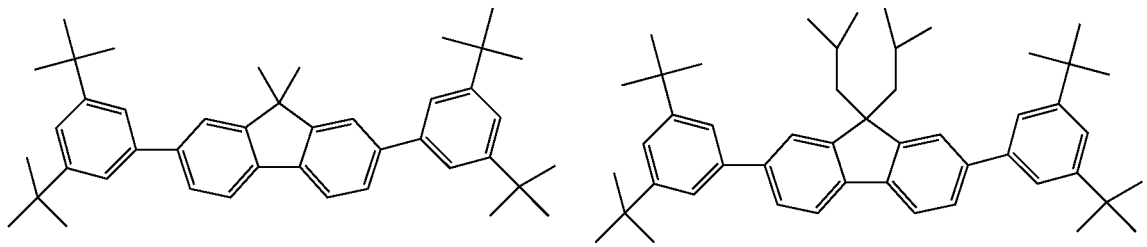
AC-11
AC-12
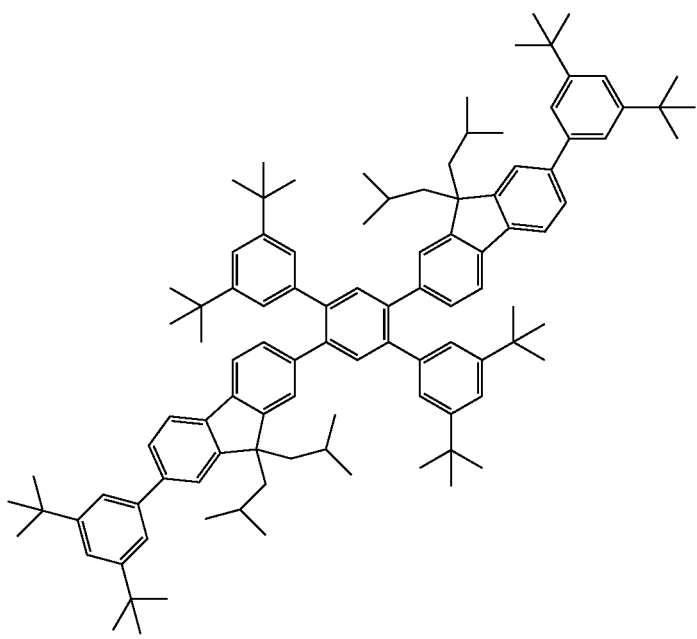
AC-13
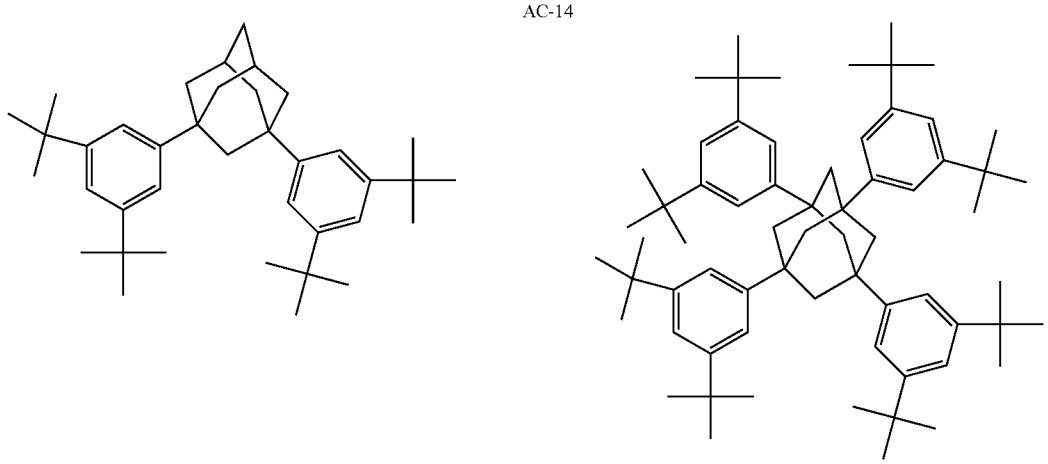
AC-14
AC-15

-continued
AC-16
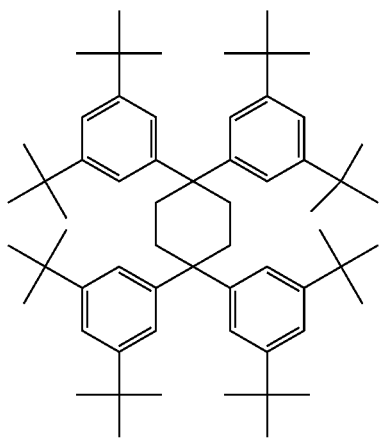
AC-17
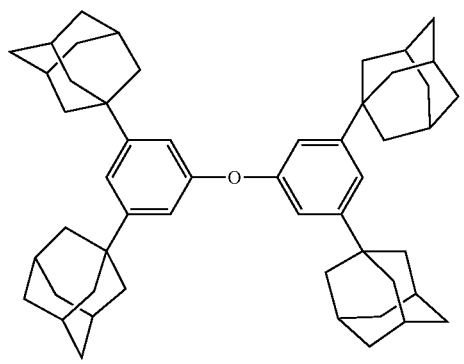
AD-1
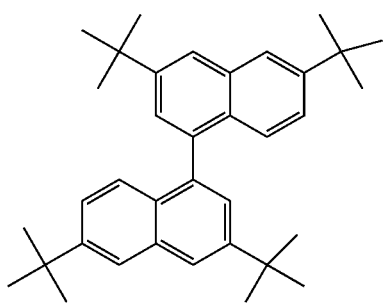
AD-2
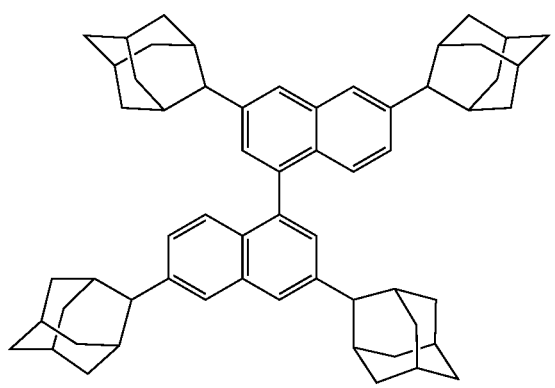
AD-3
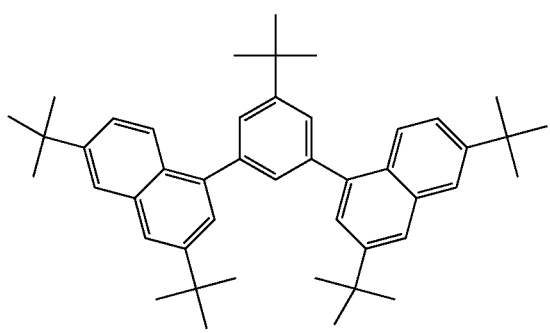
AD-4
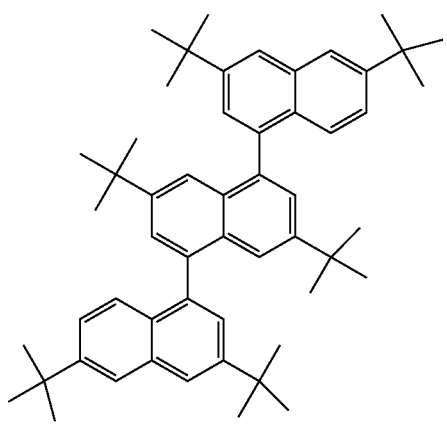

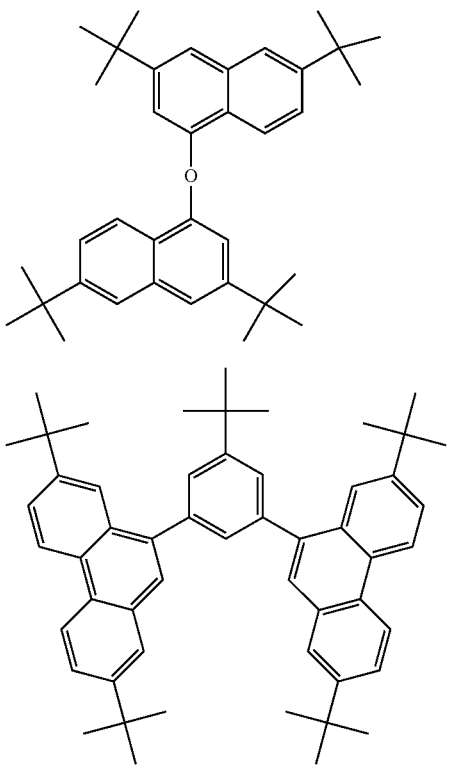

AD-5

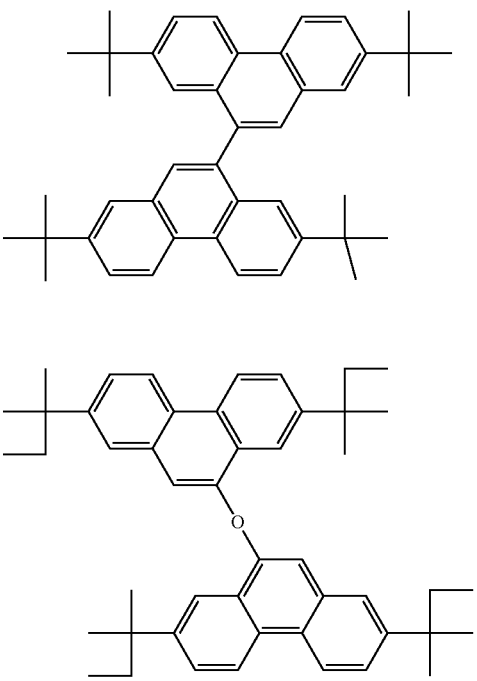

AE-1

AE-2

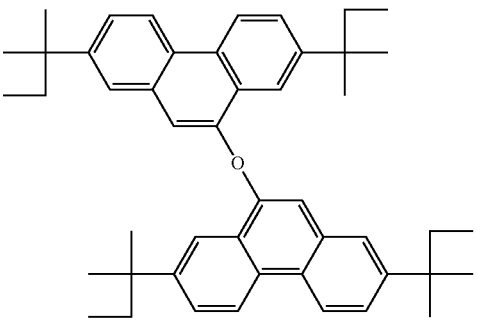

AE-3

Of the listed compounds, Exemplified Compounds AA-1 to AA-35 are each a compound having the following feature: the compound has a wide band gap and a high glass transition temperature.

Of the listed compounds, Exemplified Compounds AB-1 to AB-11 are a group of compounds in each of which $Ar_1$ represents, or $Ar_2$ and $Ar_3$ each represent, a biphenyl group. Each compound belonging to the compound group has a wide band gap and a low sublimation temperature because the compound has a rotation axis in a biphenyl skeleton.

Of the listed compounds, Exemplified Compounds AC-1 to AC-17 are a group of compounds in each of which $Ar_1$ represents, or $Ar_2$ and $Ar_3$ each represent, a phenyl group. Here, in the compound group, a compound having a wide band gap is easily designed because the band gap of a phenyl group is wide. In addition, the sublimation temperature of the compound can be reduced because its molecular weight can be reduced.

Of the listed compounds, Exemplified Compounds AD-1 to AD-5 are a group of compounds in each of which $Ar_1$ represents, or $Ar_2$ and $Ar_3$ each represent, a naphthyl group. Each compound belonging to the compound group has the following feature: the compound has a wide band gap and a high glass transition temperature.

Of the listed compounds, Exemplified Compounds AE-1 to AE-3 are a group of compounds in each of which $Ar_1$ represents, or $Ar_2$ and $Ar_3$ each represent, a phenanthryl group. Each compound belonging to the compound group has the following feature: the compound has a wide band gap and a high glass transition temperature, though having a large molecular weight.

Next, specific examples of the compound B are shown.

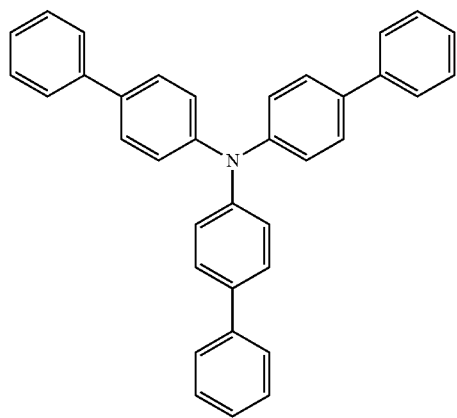

BA-1

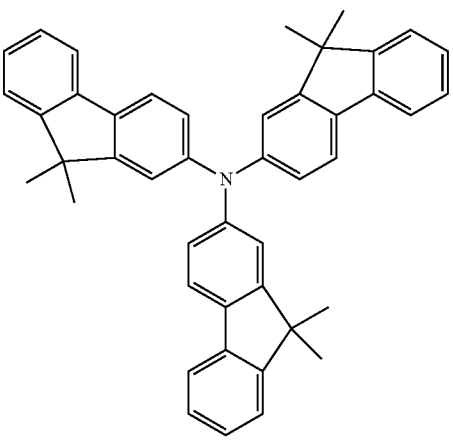

BA-2

-continued
BA-3
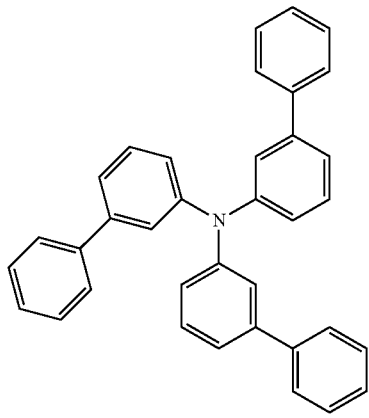
BA-4
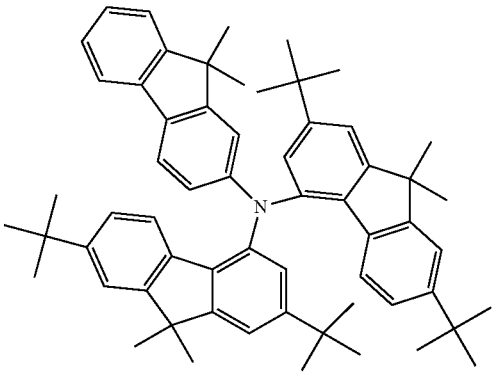
BA-5
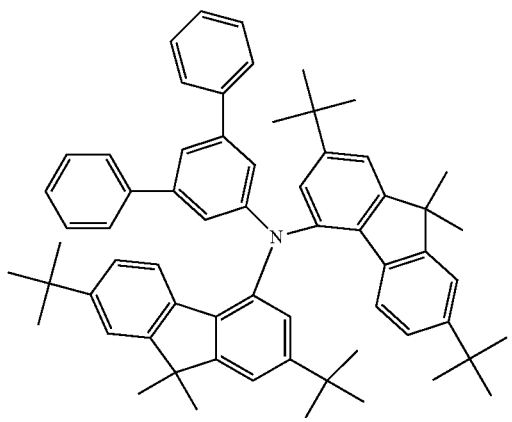
BA-6
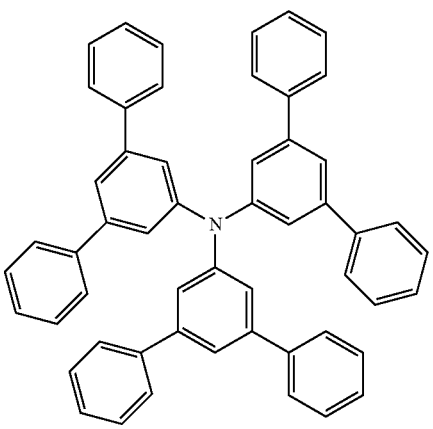
BA-7
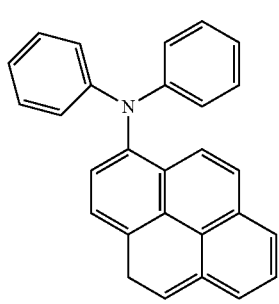
BA-8
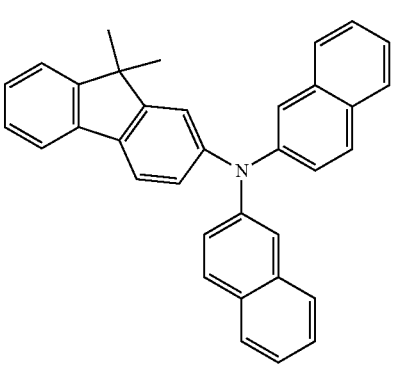
BB-1
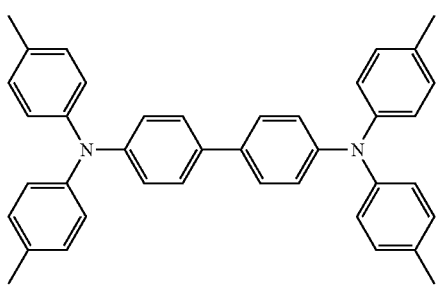
BB-2
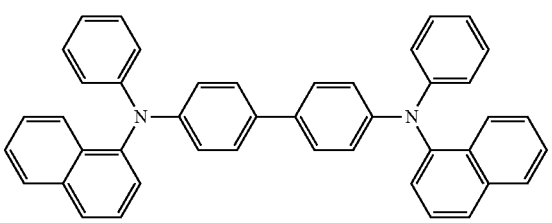

-continued
BB-3
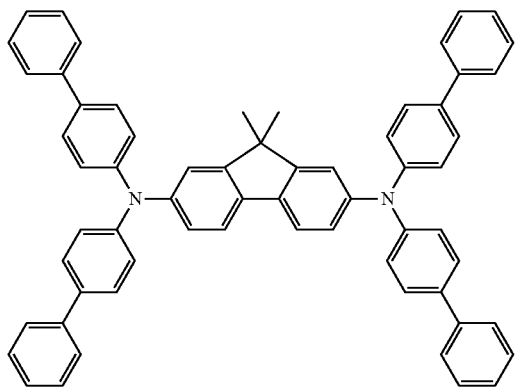
BB-4
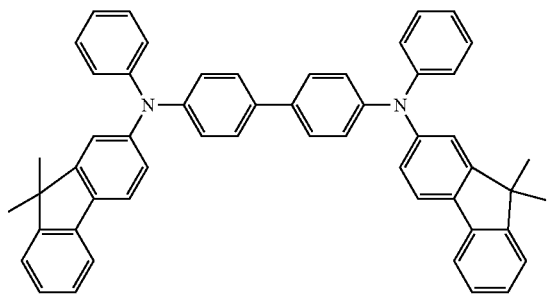
BB-5
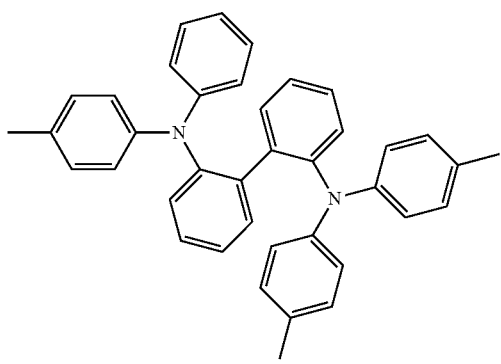
BB-6
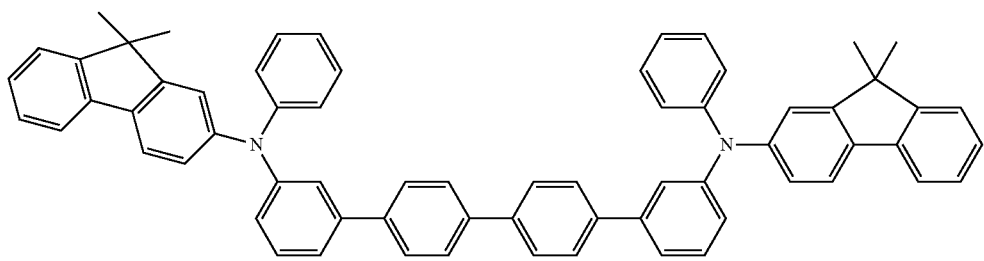
BB-7
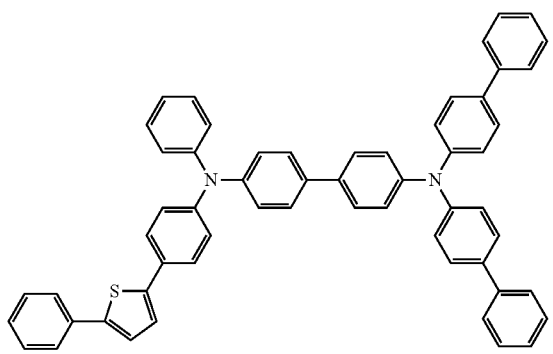
BB-8
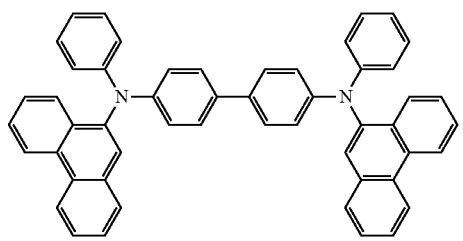

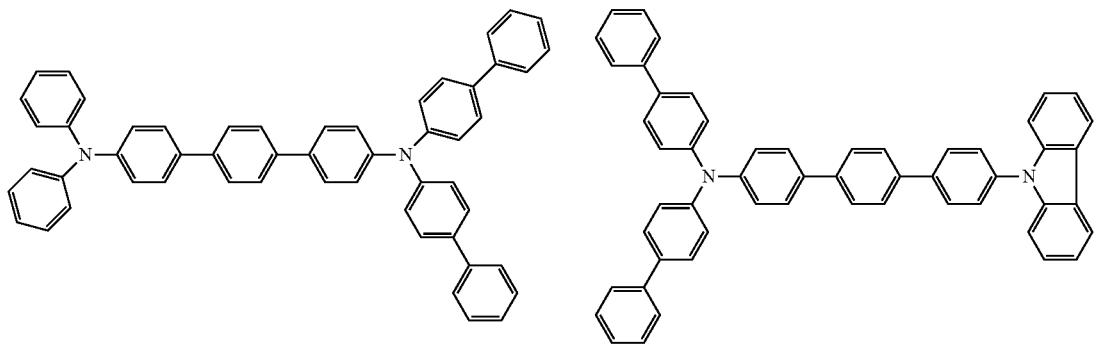
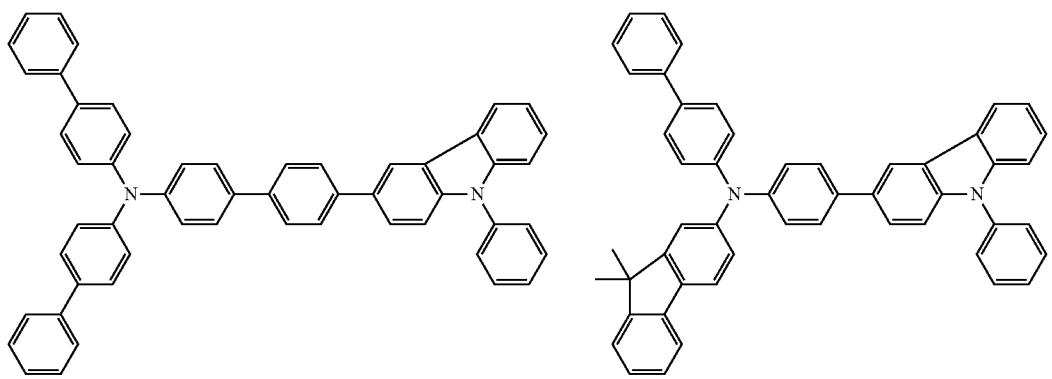
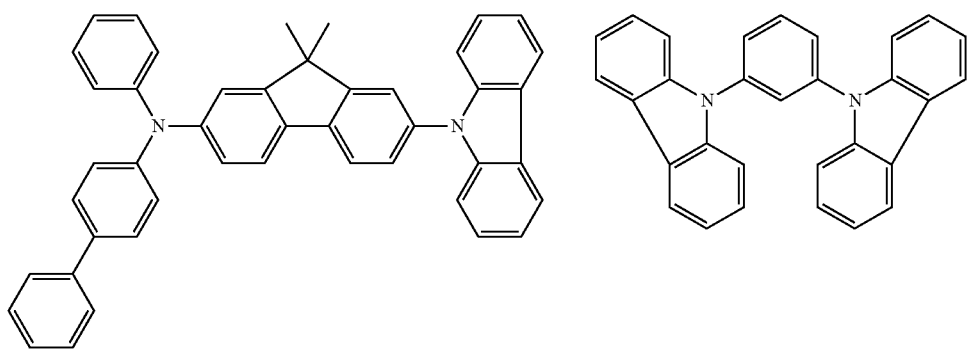
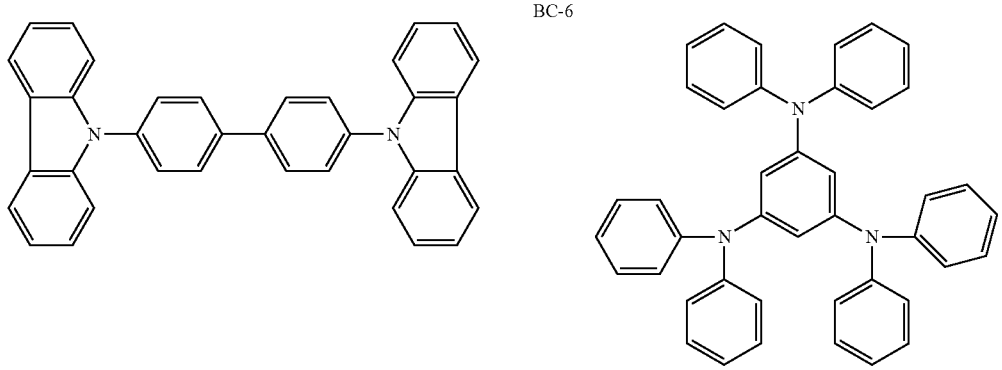

-continued
BD-2
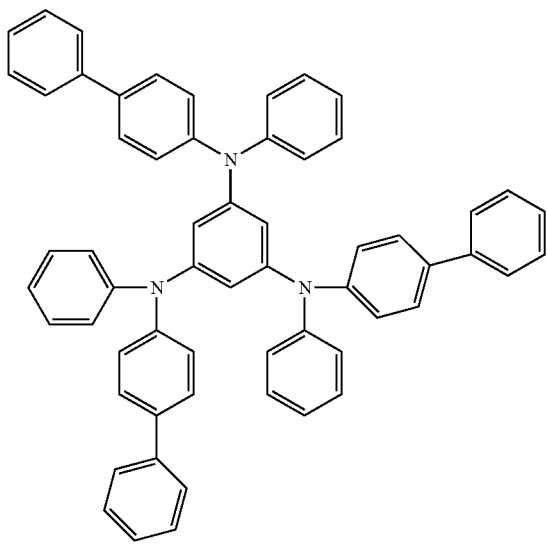
BD-3
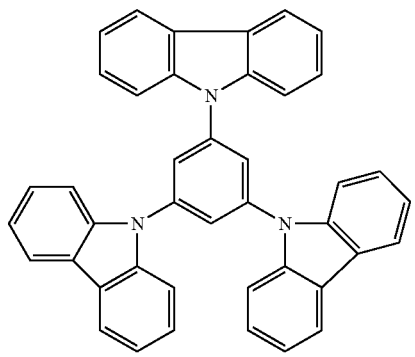
BE-1
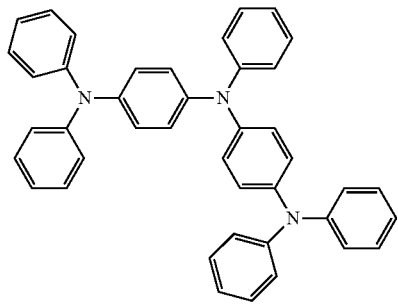
BE-2
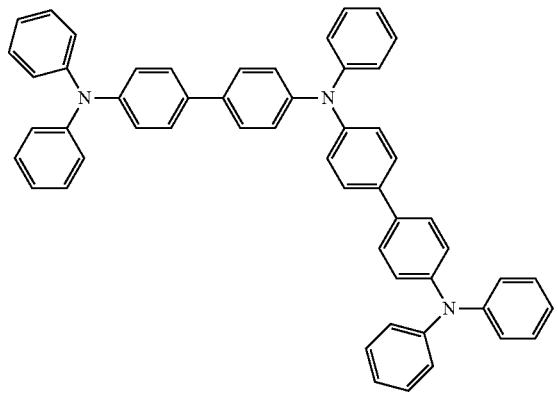
BE-3
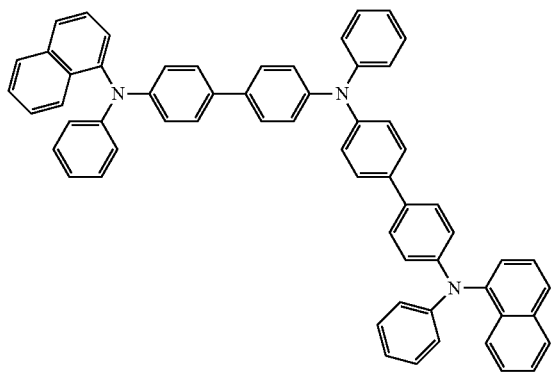
BF-1
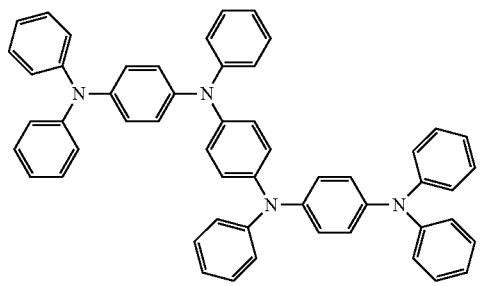

BF-2
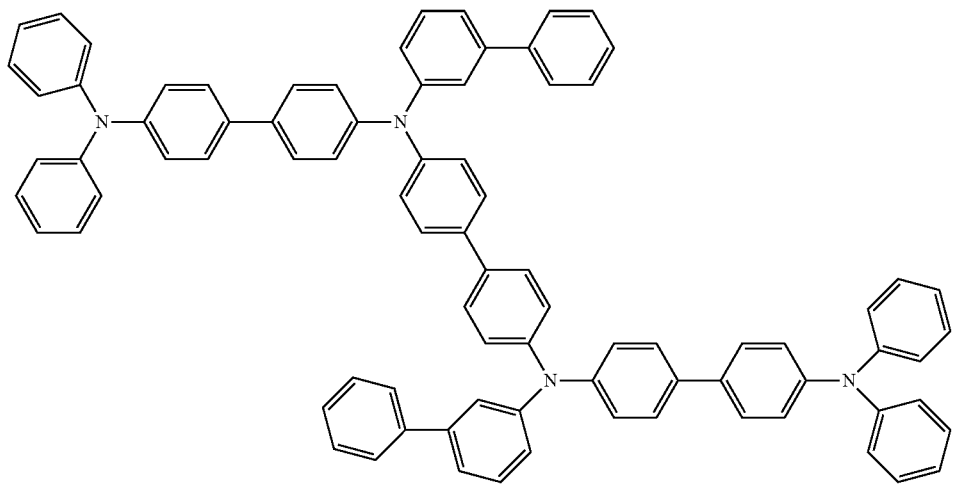
BF-3
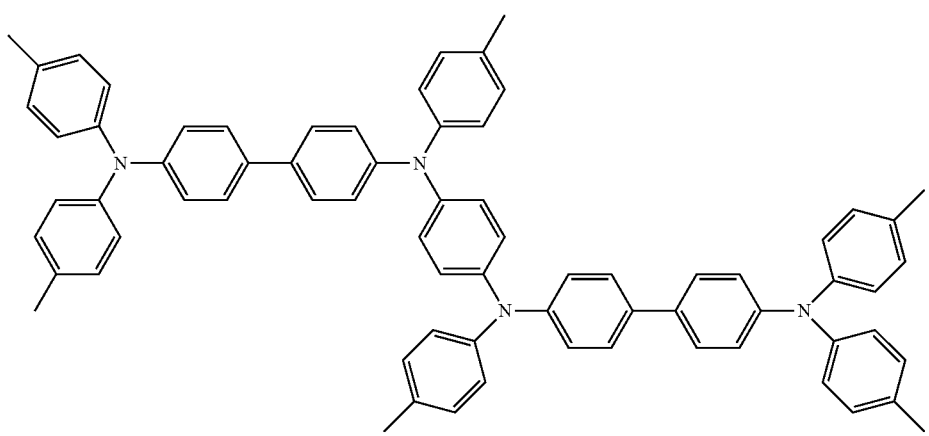
BG-1     BG-2
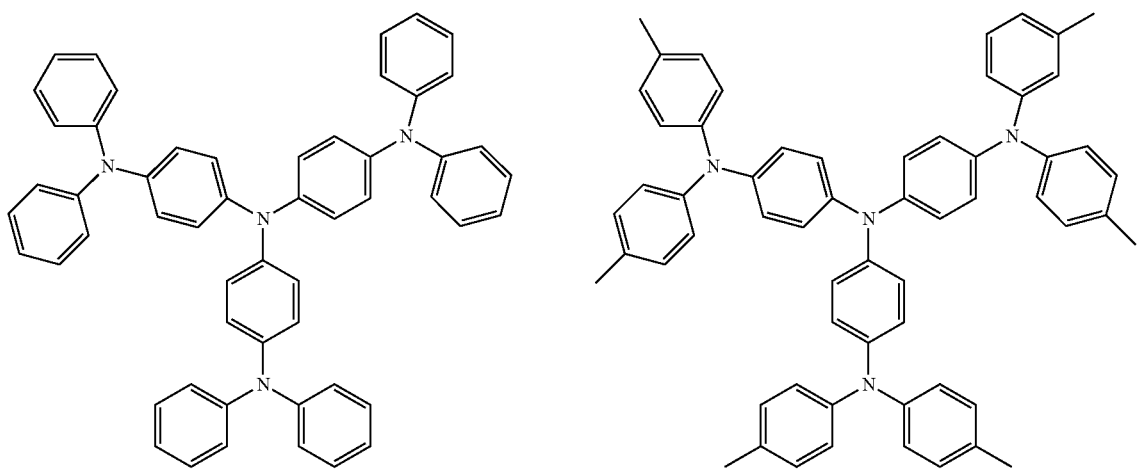

-continued
BG-3
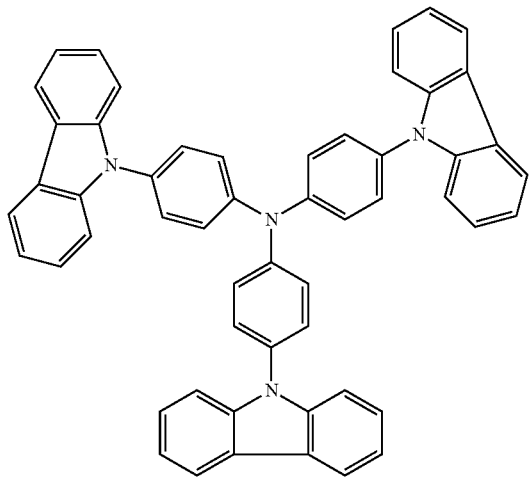
BH-1
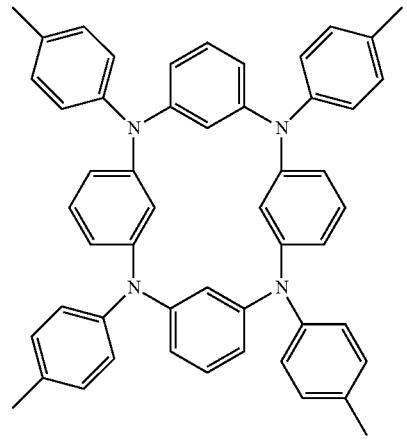
BH-2
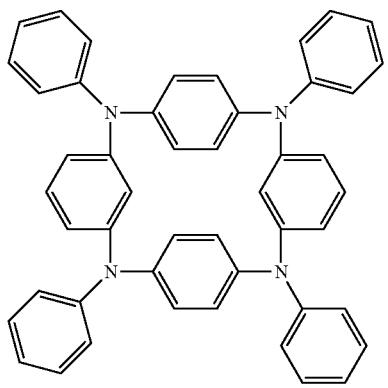
BH-3
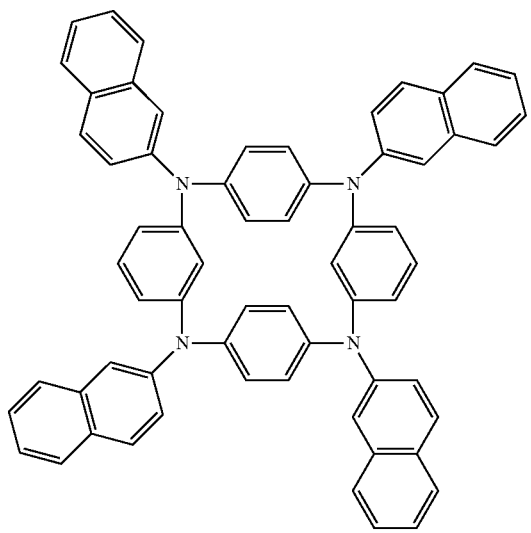
BH-4
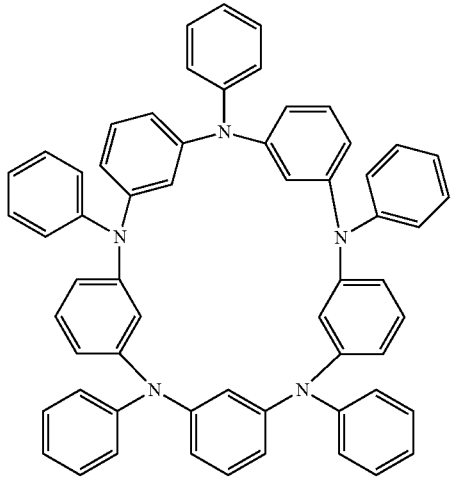
BH-5
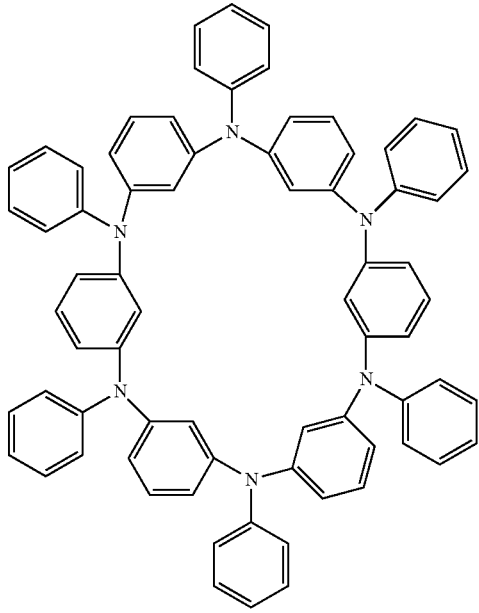

-continued

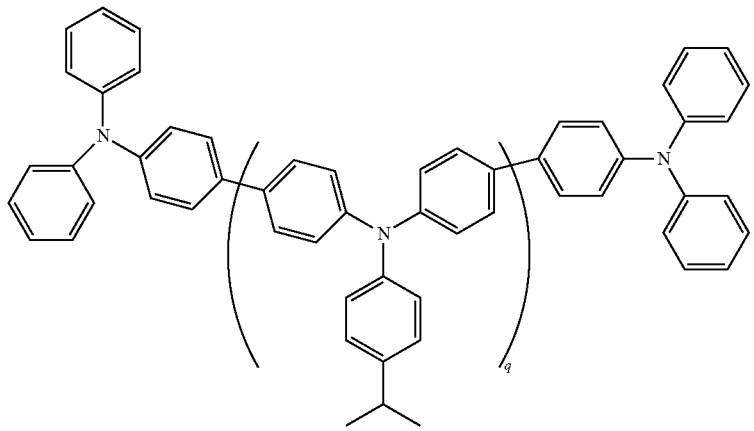

(q represents an integer of 1 or more.)

BI-1

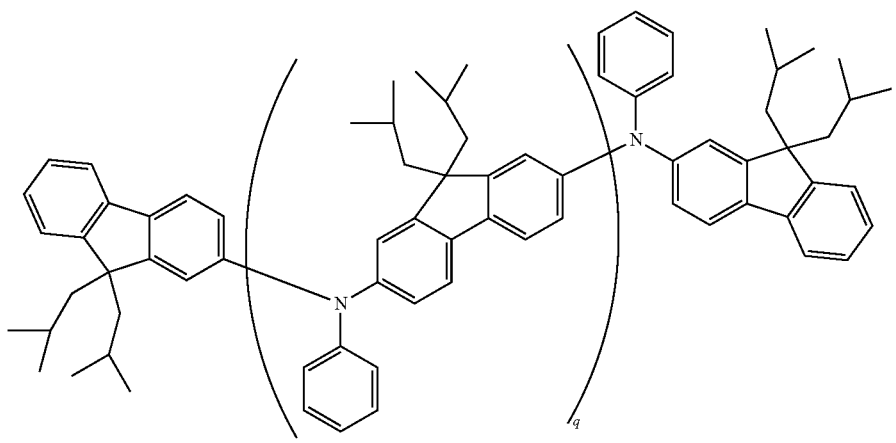

(q represnets an integer of 1 or more.)

BI-2

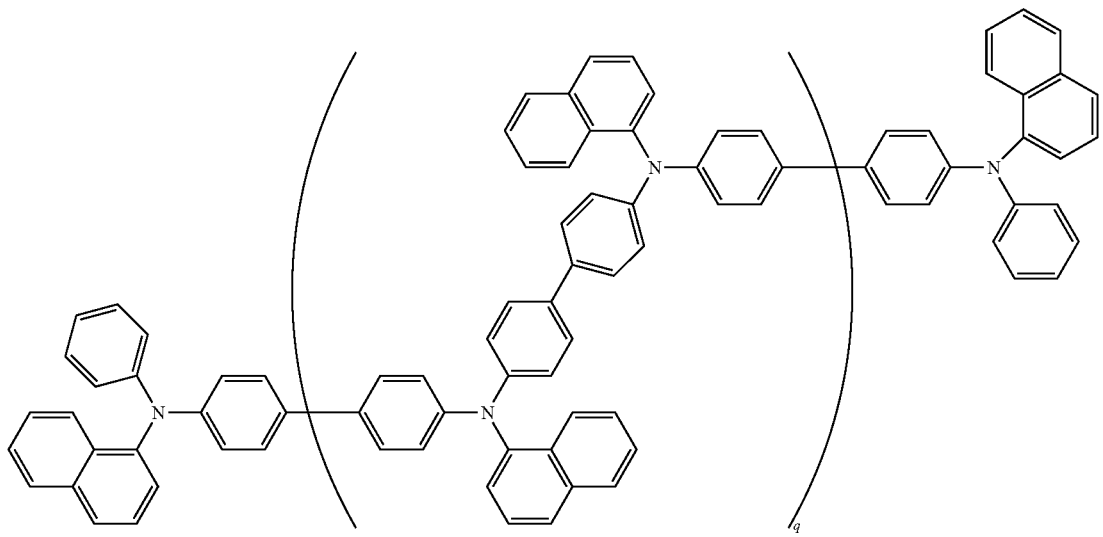

(q represents an integer of 1 or more.)

BI-3

The organic light-emitting device of the present invention, in particular, the compound A (organic compound free of a nitrogen atom and a metal atom) and the compound B (compound having a tertiary amine structure) as main constituent materials have been described above. However, the constituent materials for the organic light-emitting device of the present invention are not limited to the compound A and the compound B. It should be noted that any other constituent material to be incorporated into the organic light-emitting device of the present invention is separately described.

(2) Organic Compound

Next, an organic compound of the present invention is described. The organic compound of the present invention is a compound represented by the following general formula [3] or [4].

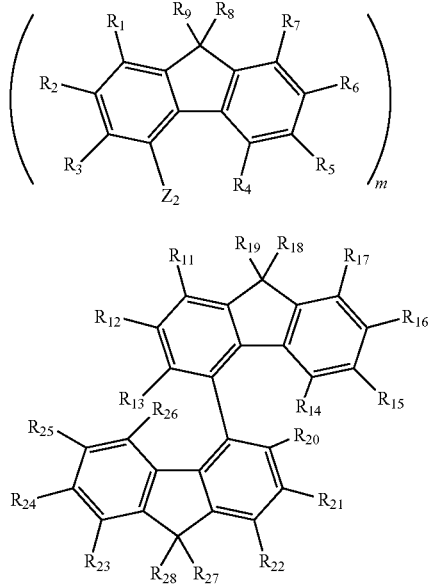

In the general formula [3], $Z_2$ represents a naphthyl group, a fluorenyl group, a phenanthryl group, a triphenylenyl group, an aliphatic condensed polycyclic group, a carbon atom, or an oxygen atom. That is, $Z_2$ represents a monovalent group, i.e., a naphthyl group, a fluorenyl group, a phenanthryl group, or a triphenylenyl group, a 2- to 6-valent group derived from the monovalent group, an aliphatic condensed polycyclic group, a carbon atom, or an oxygen atom. It should be noted that the substituent represented by $Z_2$ may further have an alkyl group, an alkoxy group, an aryl group, or a halogen atom. It is preferred that $Z_2$ represent an aliphatic condensed polycyclic group, carbon atom, or oxygen atom that may further have an alkyl group, an alkoxy group, an aryl group, or a halogen atom.

Examples of the aliphatic condensed polycyclic group represented by $Z_2$ include substituents derived from aliphatic condensed polycyclic compounds shown below.

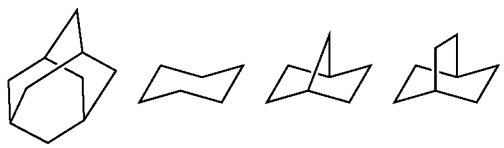

It should be noted that the substituent represented by $Z_2$ may further have: an alkyl group such as a methyl group, an ethyl group, an n-propyl group, an isopropyl group, an n-butyl group, a tert-butyl group, a sec-butyl group, an octyl group, a 1-adamantyl group, a 2-adamantyl group, a cyclohexyl group, a cyclopentyl group, or a cyclohexylmethyl group; an alkoxy group such as a methoxy group, an ethoxy group, an isopropoxy group, an n-propoxy group, a sec-butoxy group, a tert-butoxy group, or an octoxy group; an aryl group such as a phenyl group or a phenyl group having an alkyl group; or a halogen atom such as chlorine, bromine, or fluorine.

In the general formula [3], $R_1$ to $R_9$ each represent a hydrogen atom, an alkyl group, an alkoxy group, or a halogen atom, provided that at least two of the substituents represented by $R_1$ to $R_9$ are alkyl groups.

In the general formula [3], m represents an integer of 1 to 6, provided that when $Z_2$ represents a carbon atom, m represents 1 to 4, and when $Z_2$ represents an oxygen atom, m represents 1 or 2. When m represents 2 or more, structures in parentheses may be identical to or different from each other.

m preferably represents 2 or more because crystallinity is reduced and film property is improved.

In the general formula [4], $R_{11}$ to $R_{28}$ each represent a hydrogen atom, an alkyl group, an alkoxy group, or a halogen atom, provided that at least two of the substituents represented by $R_{11}$ to $R_{28}$ are alkyl groups.

The alkyl group represented by any one of $R_1$ to $R_9$ and $R_{11}$ to $R_{28}$ is preferably an alkyl group having 10 or less carbon atoms. Examples thereof include a methyl group, an ethyl group, an n-propyl group, an isopropyl group, an n-butyl group, a tert-butyl group, a sec-butyl group, an octyl group, an isoamyl group, a 1-adamantyl group, a 2-adamantyl group, a cyclohexyl group, a cyclopentyl group, and a cyclohexylmethyl group. The introduction of any such substituent improves the heat stability of the compound itself. In addition, the introduction of any such substituent can prevent intermolecular association when the compound is formed into a film, and hence can suppress the crystallization of the film and provide a long-lifetime organic light-emitting device. Of those, a branched alkyl group such as an isopropyl group, a tert-butyl group, an isoamyl group, an adamantyl group, a cyclohexyl group, a cyclopentyl group, or a cyclohexylmethyl group is more preferred. This is because the introduction of any one of those substituents additionally improves the heat stability of the compound itself.

The alkoxy group represented by any one of $R_1$ to $R_9$ and $R_{11}$ to $R_{28}$ is preferably an alkoxy group having 10 or less carbon atoms. Examples thereof include a methoxy group, an ethoxy group, an isopropoxy group, an n-propoxy group, a sec-butoxy group, a tert-butoxy group, and an octoxy group. Of those, an alkoxy group in which a branched alkyl is introduced such as an isopropoxy group, a sec-butoxy group, or a tert-butoxy group is more preferred.

Examples of the halogen atom represented by any one of $R_1$ to $R_9$ and $R_{11}$ to $R_{28}$ include chlorine, bromine, and fluorine. Of those, fluorine is preferred because it has a large preventing effect on the association of fluorene skeletons in the molecules.

In the present invention, the organic compound represented by the general formula [3] is preferably an organic compound represented by the following general formula [5]. In addition, the organic compound represented by the general formula [4] is preferably an organic compound represented by the following general formula [6].

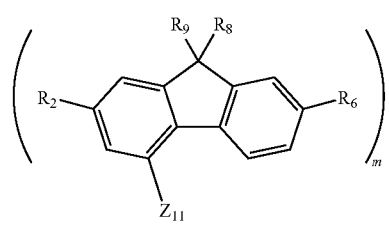

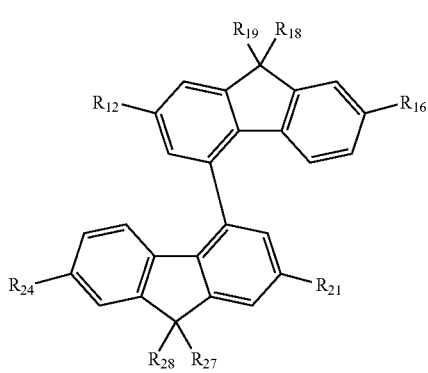

In the general formula [5], $Z_{11}$ represents a naphthyl group, a fluorenyl group, a phenanthryl group, a triphenylenyl group, an aliphatic condensed polycyclic group, a carbon atom, or an oxygen atom. It should be noted that the substituent represented by $Z_{11}$ may further have an alkyl group, an alkoxy group, an aryl group, or a halogen atom. It is preferred that $Z_{11}$ represent an aliphatic condensed polycyclic group, carbon atom, or oxygen atom that may further have an alkyl group, an alkoxy group, an aryl group, or a halogen atom.

Specific examples of the aliphatic condensed polycyclic group represented by $Z_{11}$ are the same as the specific examples of the aliphatic condensed polycyclic group represented by $Z_2$ in the general formula [3]. In addition, specific examples of the alkyl group, alkoxy group, aryl group, or halogen atom which the substituent represented by $Z_{11}$ may further have are the same as the specific examples of the alkyl group, alkoxy group, aryl group, or halogen atom which the substituent represented by $Z_2$ in the general formula [3] may further have.

In the general formula [5], m represents an integer of 1 to 6, provided that when $Z_{11}$ represents a carbon atom, m represents 1 to 4, and when $Z_{11}$ represents an oxygen atom, m represents 1 or 2. When m represents 2 or more, structures in parentheses may be identical to or different from each other.

$R_2$, $R_6$, $R_8$, $R_9$, $R_{12}$, $R_{16}$, $R_{18}$, $R_{19}$, $R_{21}$, $R_{24}$, $R_{27}$, and $R_{28}$ each represent an alkyl group or an alkoxy group, and may be identical to or different from one another. In the present invention, $R_2$, $R_6$, $R_8$, and $R_9$ in the general formula [5], and $R_{12}$, $R_{16}$, $R_{18}$, $R_{19}$, $R_{21}$, $R_{24}$, $R_{27}$, and $R_{28}$ in the general formula [6] each preferably represent an alkyl group or an alkoxy group. The reason for the foregoing is that the substitution of any one of the 2-, 7-, and 9-positions of a fluorene skeleton with an alkyl group or an alkoxy group can surely prevent the association of fluorene skeletons between molecules. In other words, when a compound is formed into a film, the occurrence of intermolecular association lengthens the wavelength of its band gap as compared with that in a dilute solution state, but each of the organic compounds represented by the general formulae [3] and [4] can prevent the lengthening of the wavelength of its band gap because intermolecular association is suppressed even when the compound is formed into a film.

Each of the organic compounds represented by the general formulae [3] to [6] has such features as described below:

(i) the compound has a wide band gap and the first peak value (peak value at the longest wavelength) of its absorption spectrum in a dilute solution is less than 400 nm; and (ii) the compound has a high lowest excited triplet state ($T_1$) and the first peak value (peak value at the shortest wavelength) of its phosphorescence emission spectrum in a low-temperature dilute solution is less than 520 nm.

As described later, the fluorene skeleton as a mother skeleton in the organic compound of the present invention is a skeleton having a first peak value of its absorption spectrum in a dilute solution state of 303 nm and having a wide band gap. In addition, the organic compound represented by the general formula [3] is such a compound that a carbon atom at the 4-position of the fluorene skeleton is substituted with the substituent $Z_2$, but the introduction of a substituent to the 4-position of the fluorene skeleton enlarges steric hindrance. In that case, conjugation between the substituent $Z_2$ and the fluorene skeleton is broken, and hence the band gap of the compound itself originates from the structure of one having the narrower band gap out of $Z_2$ and the fluorene skeleton.

By the way, $Z_2$ represents a divalent or more aromatic hydrocarbon group, aliphatic condensed polycyclic group, carbon atom, or oxygen atom that may have a substituent (an alkyl group, an alkoxy group, an aryl group, or a halogen atom). In particular, when $Z_2$ represents an aromatic hydrocarbon group, the compound is selected from aromatic hydrocarbon compounds each having a first peak value of its absorption spectrum in a dilute solution in a dilute solution state of less than 400 nm and each having a wide band gap.

Here, as shown in Table 3 below, for example, the absorption first peak wavelengths of triphenylene and phenanthrene are 336 nm and 352 nm, respectively.

TABLE 3

| Compound | Absorption first peak wavelength [nm] | $T_1$ [nm] |
| --- | --- | --- |
| c-11 (Triphenylene) | 336 | 435 |
| c-12 (Phenanthrene) | 352 | 462 |
| c-13 (Fluorene) | 303 | 429 |
| c-21 (Fluoranthene) | 362 | 540 |
| c-22 (Benzofluoranthene) | 405 | 566 |

Thus, the organic compound of the present invention has a wide band gap and the first peak value of its absorption spectrum in a dilute solution is maintained at less than 400 nm. In addition, the organic compound represented by the general formula [3] is of a structure in which each of multiple fluorene skeletons has a bonding hand with $Z_2$ at its 4-position. Accordingly, the first peak value of its absorption spectrum in a dilute solution is maintained at less than 400 nm.

Here, the organic compound of the present invention, and organic compounds (Compounds C-1 to C-3) according to Patent Literatures 3 and 4 listed below are compared from the viewpoint of the first peak value of an absorption spectrum in a dilute solution.

C-1

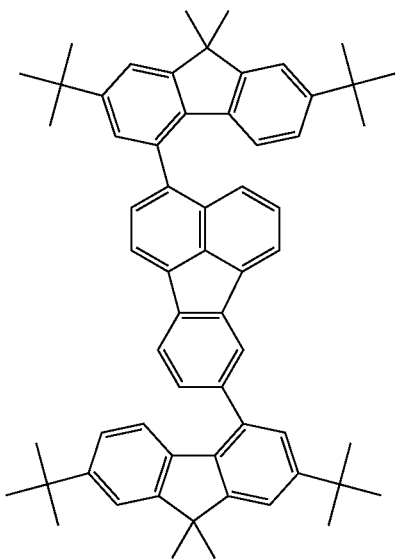

C-2

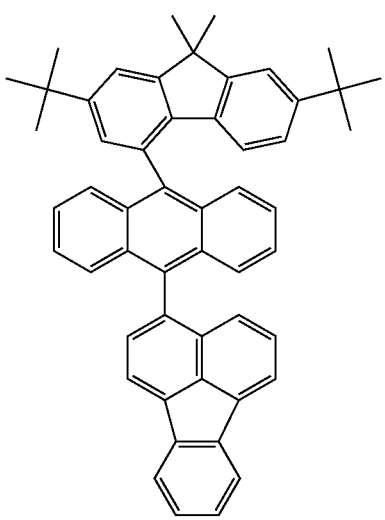

C-3

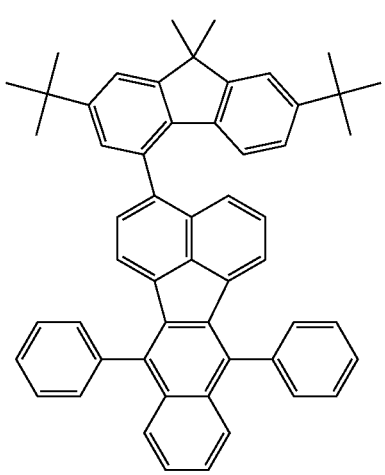

-continued c-11

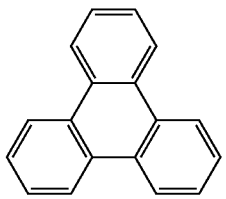

c-12

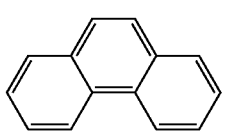

c-13

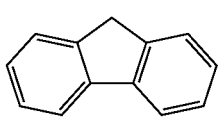

c-21

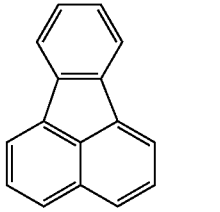

c-22

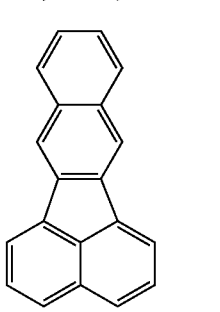

Compounds C-1 to C-3 above each have a fluoranthene skeleton or a benzofluoranthene skeleton in itself. However, fluoranthene and benzofluoranthene have narrow band gaps, and hence the first peak value of the absorption spectrum of each of the compounds in a dilute solution is 400 nm or more. For example, the first peak value of Compound C-1 is 405 nm.

The tendency concerning the band gap described above holds true for the $T_1$ as well.

The first peak value of the phosphorescence emission spectrum of fluorene, which is the mother skeleton of the organic compound of the present invention, in a low-temperature dilute solution is 429 nm. In addition, each (divalent or more) aromatic hydrocarbon group represented by $Z_2$ is selected from skeletons each having a first peak value of its phosphorescence emission spectrum in a low-temperature dilute solution of less than 520 nm and each having a high $T_1$.

Thus, the organic compound of the present invention has a high $T_1$ and the first peak value of its phosphorescence emission spectrum in a low-temperature dilute solution is maintained at less than 520 nm. On the other hand, each of Compounds C-1, C-2, and C-3 has a skeleton (a fluoranthene skeleton or a benzofluoranthene skeleton) having a $T_1$ lower than that of the (divalent or more) aromatic hydrocarbon group represented by $Z_2$. Accordingly, the first peak value of the phosphorescence emission spectrum of each of the compounds in a low-temperature dilute solution is 520 nm or more. For example, the first peak values of fluoranthene and benzofluoranthene are 540 nm and 566 nm, respectively. For information, the $T_1$ of Compound C-1 having a fluoranthene skeleton is 557 nm.

Here, Table 4 below shows an absorption first peak wavelength (first peak at longer wavelengths) in an absorption spectrum in a toluene dilute solution and a phosphorescence emission peak wavelength at 77 K in a toluene dilute solution.

TABLE 4

| Compound | Absorption first peak wavelength (nm) | $T_1$ (nm) |
|---|---|---|
| Exemplified Compound AA-1 | 308 | 444 |
| Exemplified Compound AA-9 | 308 | 505 |
| Exemplified Compound AA-20 | 303 | 443 |
| Compound c-1 | 405 | 557 |
| Compound c-11 | 336 | 435 |
| Compound c-12 | 352 | 462 |
| Compound c-13 | 303 | 429 |
| Compound c-21 | 362 | 540 |
| Compound c-22 | 405 | 566 |

(Note 1)
The absorption first peak wavelength is defined from the peak wavelength of the toluene solution ($1 \times 10^{-6}$ mol/l) at the longest wavelength. It should be noted that a spectrophotometer U-3010 manufactured by Hitachi, Ltd. is used in the measurement.
(Note 2)
The toluene solution ($1 \times 10^{-4}$ mol/l) is cooled to 77 K, its phosphorescence emission component is measured at an excitation wavelength of 320 nm, and the peak wavelength at the shortest wavelength is defined as the $T_1$. It should be noted that a spectrophotometer U-3010 manufactured by Hitachi, Ltd. is used in the measurement.

By the way, the structure of the entire molecule of each of the organic compounds represented by the general formulae [3] and [4] is non-planar because the compound is bonded to an adjacent substituent at the 4-position of its fluorene skeleton. When the organic compound of the present invention is brought into a thin-film state, the film becomes an amorphous film that hardly crystallizes and is stable by virtue of the presence of the foregoing feature. In addition, the presence of the feature can suppress the occurrence of an excimer because the presence suppresses the occurrence of intermolecular stacking.

By virtue of the foregoing features, the organic compound of the present invention is useful as a constituent material for an organic light-emitting device, specifically, a host to be incorporated into its emission layer. In addition, the organic compound of the present invention can provide an organic light-emitting device having high device durability because an amorphous film that hardly crystallizes and is stable can be formed from the compound.

In addition, the compound has a wide band gap and a $T_1$ of less than 520 nm. Accordingly, when the compound is used as a host for a blue fluorescent light-emitting material or for a blue or green phosphorescent light-emitting material out of the hosts, light emission derived from a light-emitting dopant can be output. Here, its features, i.e., a wide band gap and a $T_1$ of less than 520 nm exhibit a large suppressing effect on the diffusion of an exciton from the emission layer, and hence the compound is also useful as a transport layer such as a hole transport layer or an electron transport layer, or a layer for blocking a charge such as an electron-blocking layer or a hole-blocking layer.

Specific examples of the organic compound of the present invention are listed below.

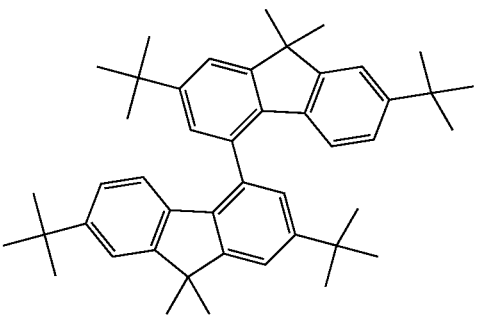

AA-1

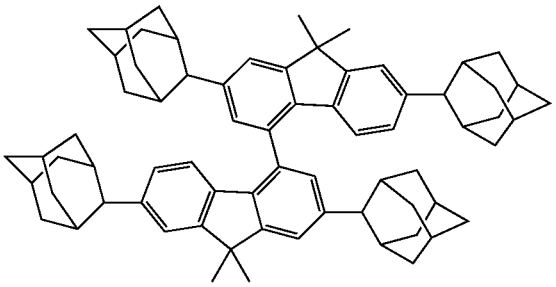

AA-2

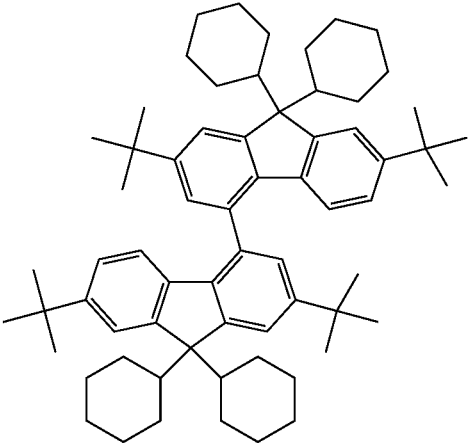

AA-3

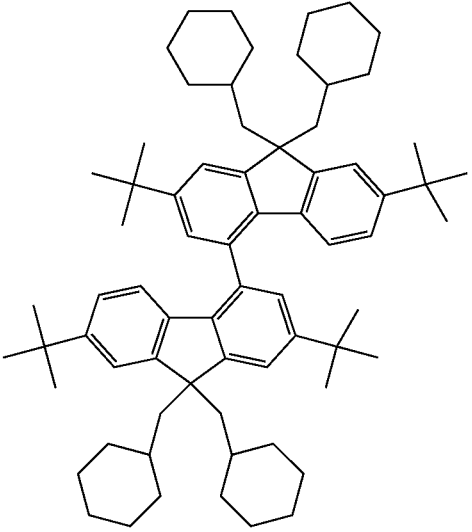

AA-4

AA-9
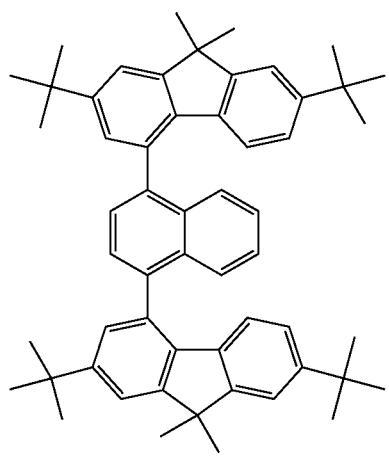
AA-17
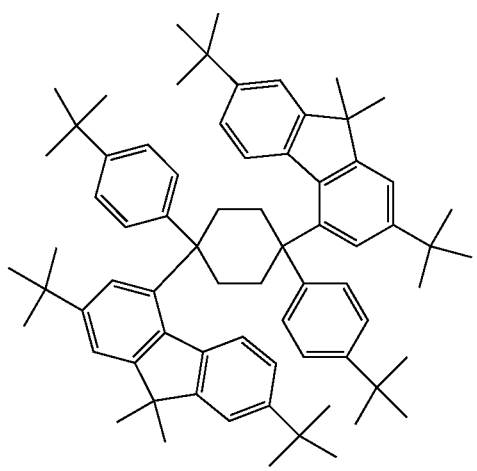
AA-10
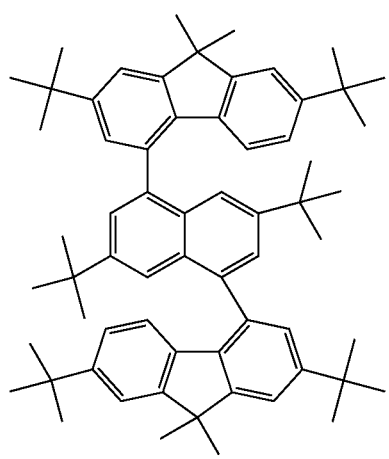
AA-18
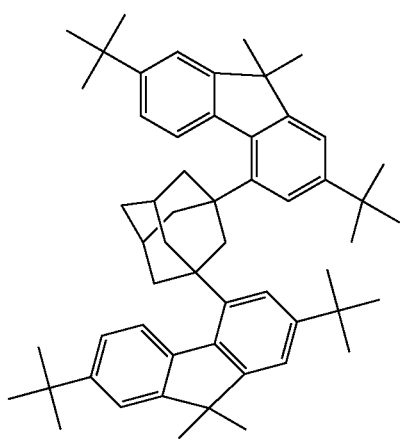
AA-11
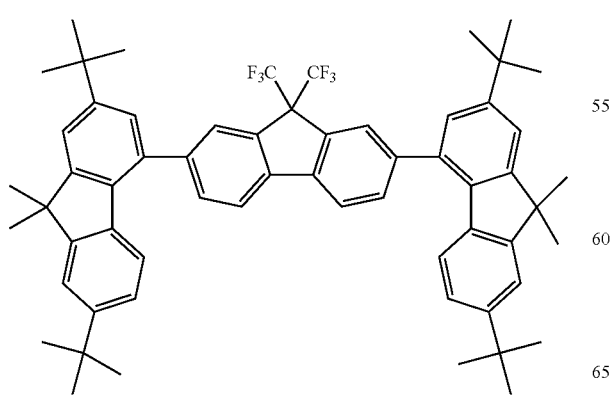
AA-19
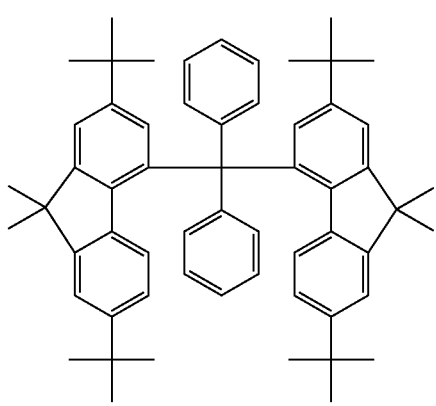

AA-20
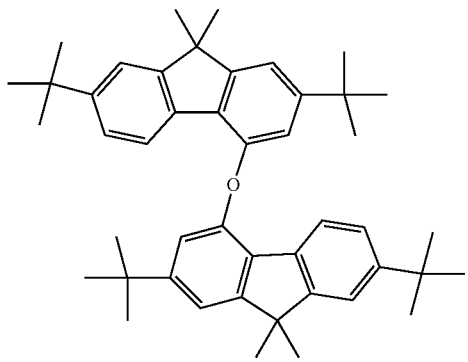
AA-21
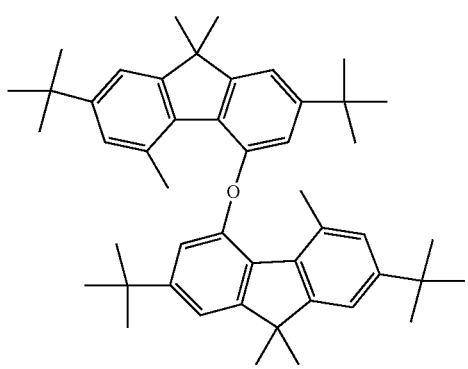
AA-22
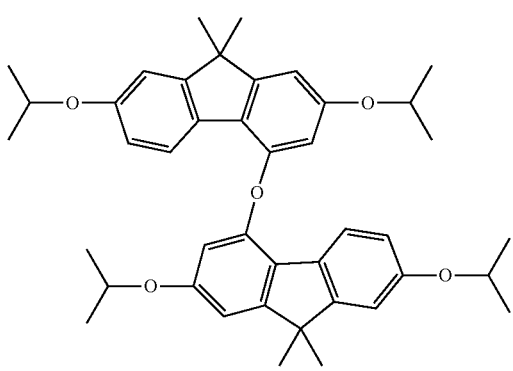
AA-23
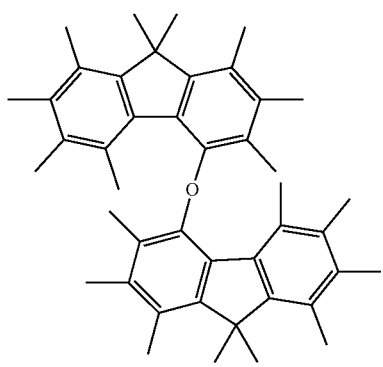
AA-28
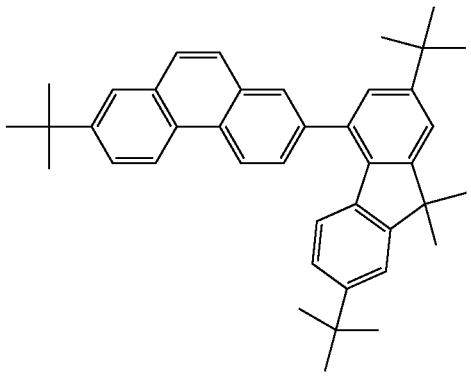
AA-29
AA-34
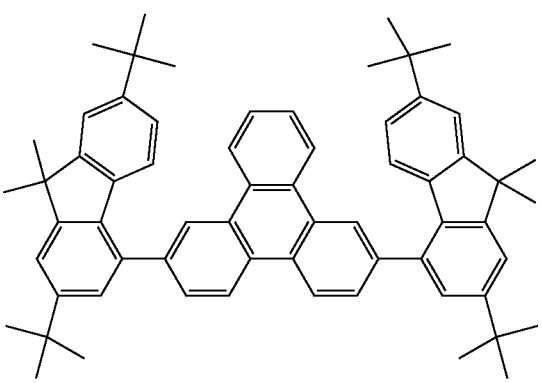

-continued

AA-35

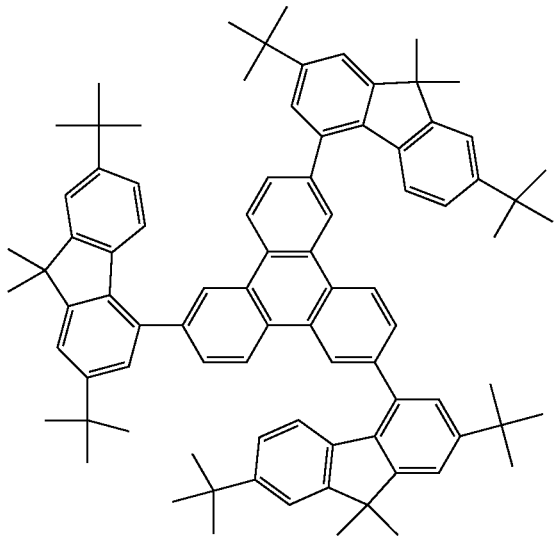

Of the listed compounds, Exemplified Compounds AA-1 to AA-4 are a group of compounds each corresponding to the organic compound represented by the general formula [4]. Each of those compounds has a high deposition speed at the time of its vacuum deposition because of the following reason: the compound has a small molecular weight, and hence has high sublimability and sublimates at a low temperature.

Of the listed compounds, Exemplified Compounds AA-9 to AA-11 are a group of compounds each corresponding to the organic compound represented by the general formula [3] and are a group of compounds in each of which $Z_2$ represents a naphthyl group or a fluorenyl group. The $T_1$'s of the compounds themselves are high because each of a naphthyl group and a fluorenyl group is a substituent having a $T_1$ of 500 nm or less. Accordingly, the use of any such compound as a host to be incorporated into an emission layer constituting an organic light-emitting device or as a constituent material for a charge transport layer or charge-blocking layer may improve its emission efficiency. The compounds are particularly preferred in green phosphorescent light-emitting devices.

Of the listed compounds, Exemplified Compounds AA-17 to AA-19 are a group of compounds each corresponding to the organic compound represented by the general formula [3] and are a group of compounds in each of which $Z_2$ represents a carbon atom or an aliphatic condensed polycyclic group. Each compound belonging to the compound group is of such a structure that conjugation with a fluorene skeleton does not occur. Accordingly, both of its band gap and $T_1$ enlarge. Therefore, the compound is preferred in a blue phosphorescent device.

Of the listed compounds, Exemplified Compounds AA-20 to AA-23 are a group of compounds each corresponding to the organic compound represented by the general formula [3] and are a group of compounds in each of which $Z_2$ represents an oxygen atom. Each compound belonging to the compound group has a low ionization potential because the compound has an electron-donating effect based on an oxygen atom. Accordingly, the use of the compound as a host to be incorporated into an emission layer constituting an organic light-emitting device or as a constituent material for a hole transport layer or electron-blocking layer promotes the injection of a hole and reduces its driving voltage.

Of the listed compounds, Exemplified Compounds AA-28 to AA-35 are a group of compounds each corresponding to the organic compound represented by the general formula [3] and are a group of compounds in each of which $Z_2$ represents an aromatic condensed polycyclic group obtained by condensing three or more rings. Here, the aromatic condensed polycyclic group obtained by condensing three or more rings is a substituent having a $T_1$ of 580 nm or less and high planarity, specifically, a phenanthryl group or a triphenylenyl group. Each compound belonging to the compound group has a high $T_1$, and hence its use as a host to be incorporated into an emission layer constituting an organic light-emitting device or as a constituent material for a hole transport layer or electron-blocking layer may improve its emission efficiency. The compound is particularly preferably used as a constituent material for a green or red phosphorescent light-emitting device. In addition, each compound belonging to the compound group has a substituent having high planarity, and hence carrier hopping between its molecules may be promoted and its carrier mobility may be high.

The organic compound of the present invention, which is mainly used as a constituent material for an organic light-emitting device, can be used as a material not only for the organic light-emitting device but also for a living organism internal indicator or filter film.

When the organic compound of the present invention is used as a constituent material for the organic light-emitting device, embodiments of the organic light-emitting device including the organic compound of the present invention are roughly classified into two embodiments, specifically, the following embodiments (2A) and (2B):

(2A) an organic light-emitting device including at least an anode, a cathode, an emission layer formed between the anode and the cathode, and an organic compound layer formed between the anode and the emission layer, the organic compound layer containing a compound having a tertiary amine structure; and (2B) an organic light-emitting device including an anode, a cathode, and an organic compound layer formed between the anode and the cathode.

When the organic compound of the present invention is used as a constituent material for the organic light-emitting device according to the aspect (2A), the organic compound of the present invention is incorporated into the organic compound layer together with the compound having a tertiary amine structure ("Compound B" described in the section "(1) Organic light-emitting device"). Here, the organic compound layer constituting the organic light-emitting device according to the aspect (2A) is a layer formed between the anode and the emission layer. Accordingly, the organic compound of the present invention is incorporated into a layer formed between the anode and the emission layer such as a hole transport layer, a hole injection layer, or an electron-blocking layer.

By the way, the aspect (2B) can be subdivided into the following (2B-1) to (2B-3):

(2B-1) an organic light-emitting device including an anode, a cathode, an emission layer formed between the anode and the cathode, and an organic compound layer (hole injection/transport layer) formed between the anode and the emission layer;

(2B-2) an organic light-emitting device including an anode, a cathode, an emission layer formed between the anode and the cathode, and an organic compound layer (electron injection/transport layer) formed between the cathode and the emission layer; and (2B-3) an organic light-emitting device including an anode, a cathode, and an emission layer formed between the anode and the cathode (an organic light-emitting device including an emission layer as the "organic compound layer" in the aspect (2B)).

When the organic compound of the present invention is used as a constituent material for the organic light-emitting device according to the aspect (2B), examples of the organic compound layer containing the organic compound of the present invention include an emission layer, a hole injection/transport layer (a hole injection layer, a hole transport layer, or an electron-blocking layer), and an electron injection/transport layer (an electron injection layer, an electron transport layer, or a hole• exciton-blocking layer). In addition, when the organic compound of the present invention is used as a constituent material for the organic light-emitting device according to the aspect (2B), the layer containing the organic compound of the present invention may be a single layer or may be multiple layers. Further, when the organic compound of the present invention is used as a constituent material for the organic light-emitting device according to the aspect (2B), the layer containing the organic compound of the present invention may be a layer formed only of the organic compound of the present invention, or may be a layer obtained by mixing the organic compound of the present invention and any other compound.

The basic construction of the organic light-emitting device including the organic compound of the present invention is, for example, described in each of the following constructions (a) to (e), provided that the present invention is not limited thereto.

(a) (Substrate/) anode/emission layer/cathode
(b) (Substrate/) anode/hole transport layer/electron transport layer/cathode
(c) (Substrate/) anode/hole transport layer/emission layer/electron transport layer/cathode
(d) (Substrate/) anode/hole injection layer/hole transport layer/emission layer/electron transport layer/cathode
(e) (Substrate/) anode/hole transport layer/emission layer/hole• exciton-blocking layer/electron transport layer/cathode Although each of the constructions (a) to (e) is a construction in the case where an electrode close to the substrate is the anode, the present invention is not limited thereto and a construction in the case where the electrode close to the substrate is the cathode is of course included in the present invention.

(3) Other Constituent Materials for Organic Light-Emitting Device

Next, other constituent materials for the organic light-emitting device of the present invention (materials except the compound A (including a compound corresponding to the organic compound of the present invention) and the compound B) are described. In the organic light-emitting device of the present invention, conventionally known low-molecular weight and high-molecular weight materials can be used as required. More specifically, a hole injectable/transportable material, an emission assist material, an electron injectable/transportable material, or the like can be used.

Hereinafter, examples of these materials are described.

Examples of the hole injectable/transportable material include a triarylamine derivative, a phenylenediamine derivative, a stilbene derivative, a phthalocyanine derivative, a porphyrin derivative, poly(vinyl carbazole), poly(thiophene), and any other conductive polymer. It should be noted that the present invention is not limited to these materials.

As a light-emitting material (guest) mainly involved in light-emitting function, there are given, for example: a fluorescent light-emitting material that emits blue, green, or red light such as a triarylamine derivative, a phenylene derivative, a condensed ring aromatic compound (e.g., a fluoranthene derivative, a benzofluoranthene derivative, a pyrene derivative, a chrysene derivative, or a derivative obtained by substitution thereof with a diarylamine), or a stilbene derivative; and a phosphorescent light-emitting material that emits blue, green, or red light such as an organic metal complex (e.g., an organic iridium complex, an organic platinum complex, or a rare earth metal complex).

In the present invention, the content of the guest is preferably 0.1 mass % or more and 30 mass % or less, more preferably 0.5 mass % or more and 10 mass % or less with reference to the total amount of the emission layer.

The host in the emission layer is a material having the highest weight ratio in the emission layer. Examples of the host include, but of course not limited to, a triarylamine derivative, a phenylene derivative, a condensed ring aromatic compound (e.g., a naphthalene derivative, a phenanthrene derivative, a fluorene derivative, or a chrysene derivative), an organic metal complex (e.g., an organic aluminum complex such as tris(8-quinolinolato)aluminum, an organic beryllium complex, an organic iridium complex, or an organic platinum complex), and a polymer derivative such as a poly(phenylene vinylene) derivative, a poly(fluorene) derivative, a poly(phenylene) derivative, a poly(thienylene vinylene) derivative, or a poly(acetylene) derivative.

More specific examples of the host include the group of compounds represented in Table 5.

TABLE 5

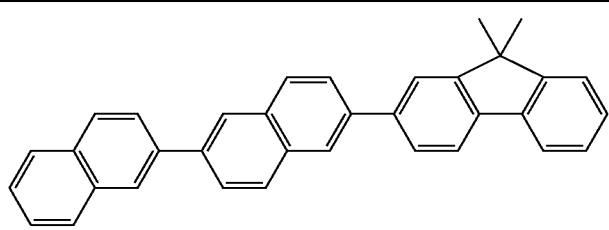

H1

TABLE 5-continued
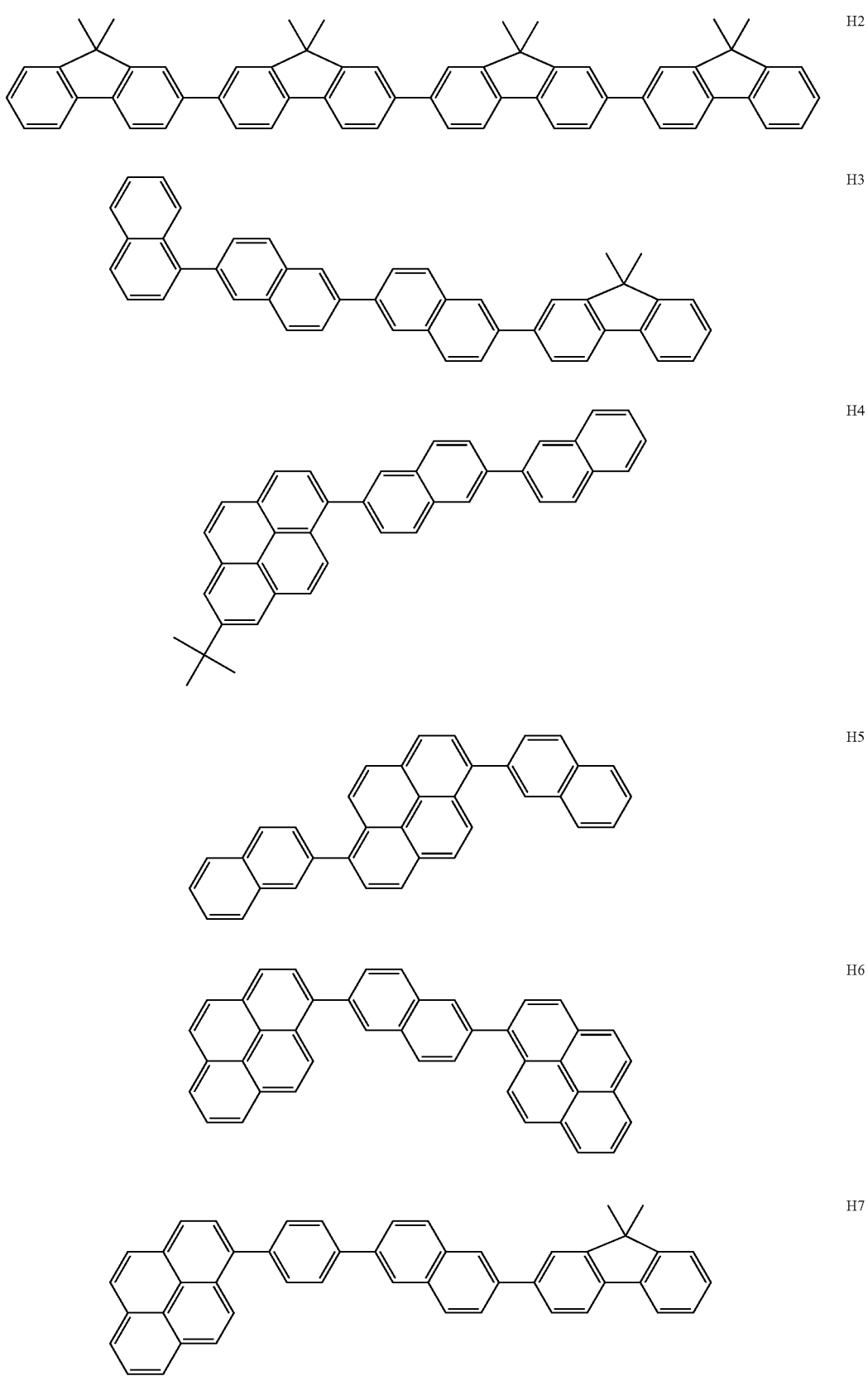

TABLE 5-continued
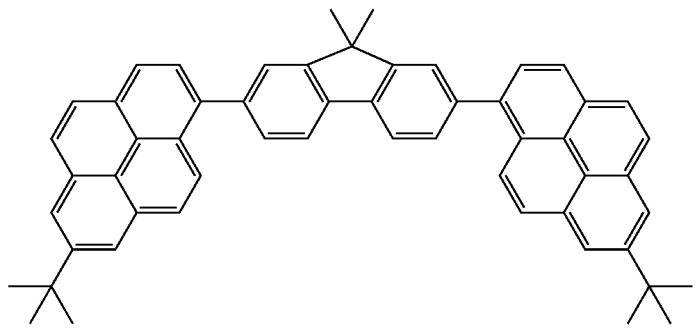 [SMILES: CC(C)(C)c1cc2ccc3ccc(-c4ccc5c(c4)C(C)(C)c4cc(-c6ccc7ccc8cc(C(C)(C)C)cc9ccc6c7c89)ccc4-5)c4ccc(c1)c2c34] H8
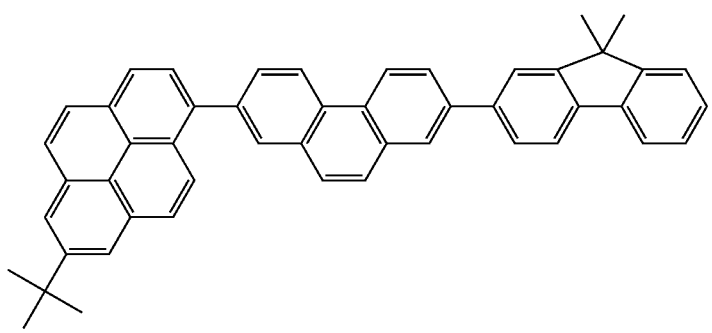 [SMILES: CC(C)(C)c1cc2ccc3ccc(-c4ccc5c(ccc6cc(-c7ccc8c(c7)C(C)(C)c7ccccc7-8)ccc65)c4)c4ccc(c1)c2c34] H9
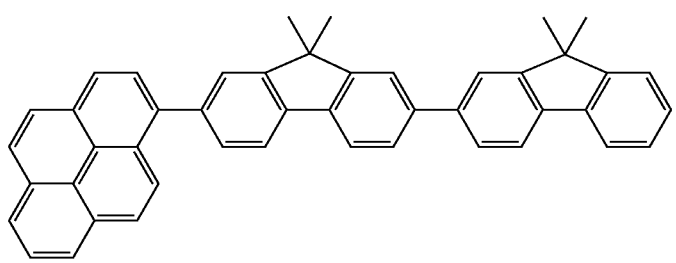 [SMILES: CC1(C)c2ccccc2-c2ccc(-c3ccc4c(c3)C(C)(C)c3cc(-c5ccc6ccc7cccc8ccc5c6c78)ccc3-4)cc21] H10
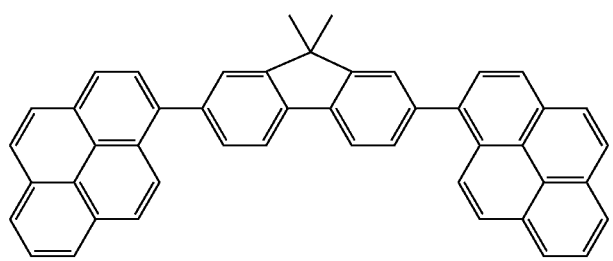 [SMILES: CC1(C)c2cc(-c3ccc4ccc5cccc6ccc3c4c56)ccc2-c2ccc(-c3ccc4ccc5cccc6ccc3c4c56)cc21] H11
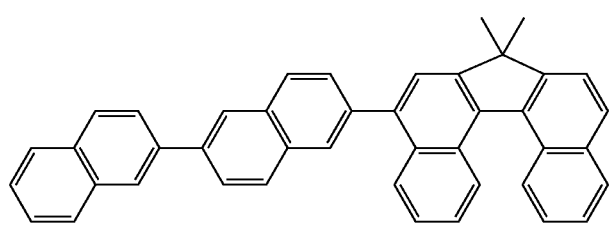 [SMILES: CC1(C)c2ccc3ccccc3c2-c2c1cc(-c1ccc3cc(-c4ccc5ccccc5c4)ccc3c1)c1ccccc21] H12

TABLE 5-continued
| | |
|---|---|
| 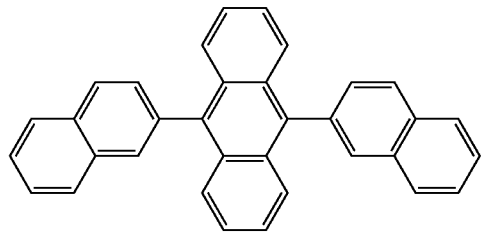 [SMILES: c1ccc2cc(-c3c4ccccc4c(-c4ccc5ccccc5c4)c4ccccc34)ccc2c1] | H13 |
| 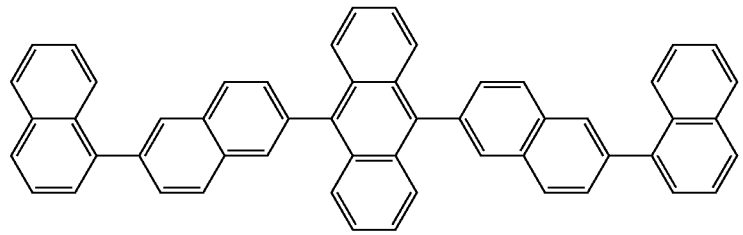 [SMILES: c1ccc2c(-c3ccc4cc(-c5c6ccccc6c(-c6ccc7cc(-c8cccc9ccccc89)ccc7c6)c6ccccc56)ccc4c3)cccc2c1] | H14 |
| 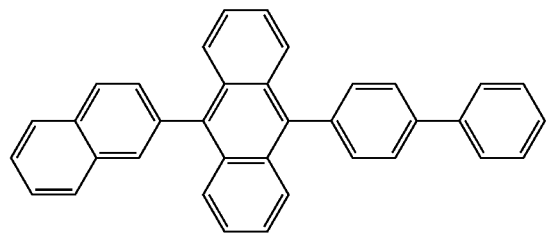 [SMILES: c1ccc(-c2ccc(-c3c4ccccc4c(-c4ccc5ccccc5c4)c4ccccc34)cc2)cc1] | H15 |
| 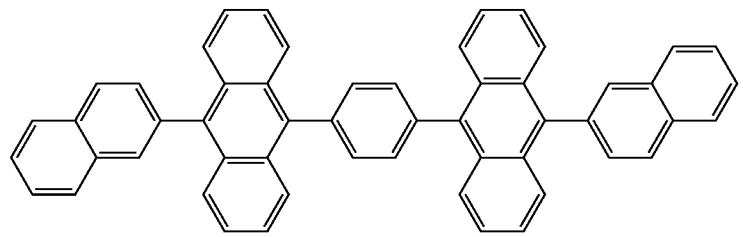 [SMILES: c1ccc2cc(-c3c4ccccc4c(-c4ccc(-c5c6ccccc6c(-c6ccc7ccccc7c6)c6ccccc56)cc4)c4ccccc34)ccc2c1] | H16 |
| 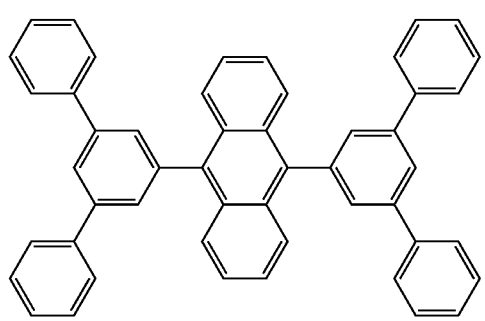 [SMILES: c1ccc(-c2cc(-c3ccccc3)cc(-c3c4ccccc4c(-c4cc(-c5ccccc5)cc(-c5ccccc5)c4)c4ccccc34)c2)cc1] | H17 |
| 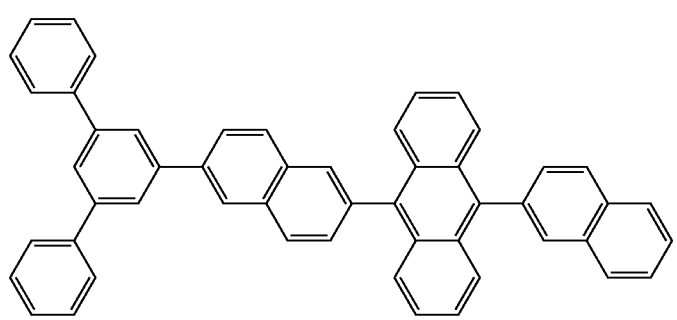 [SMILES: c1ccc(-c2cc(-c3ccccc3)cc(-c3ccc4cc(-c5c6ccccc6c(-c6ccc7ccccc7c6)c6ccccc56)ccc4c3)c2)cc1] | H18 |

TABLE 5-continued
| | |
|---|---|
| 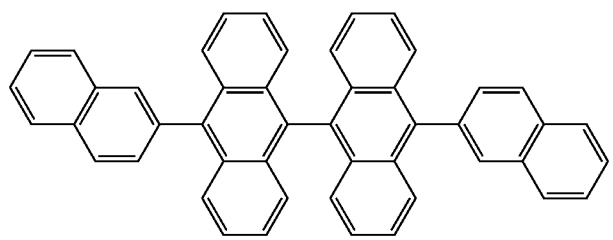 [SMILES: c1ccc2cc(-c3c4ccccc4c(-c4c5ccccc5c(-c5ccc6ccccc6c5)c5ccccc45)c4ccccc34)ccc2c1] | H19 |
| 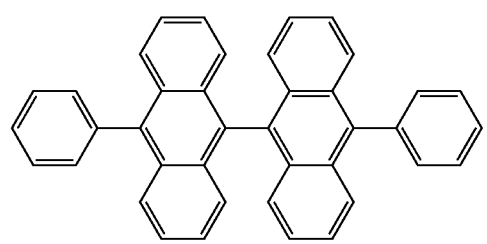 [SMILES: c1ccc(-c2c3ccccc3c(-c3c4ccccc4c(-c4ccccc4)c4ccccc34)c3ccccc23)cc1] | H20 |
| 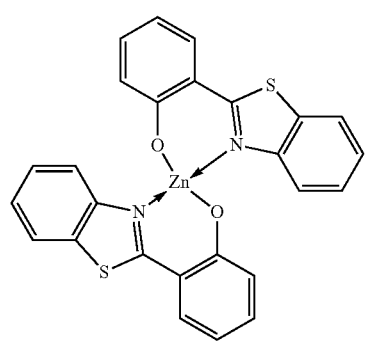 | H21 |
| 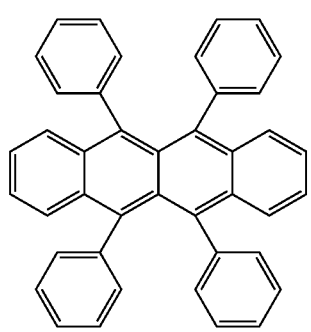 [SMILES: c1ccc(-c2c3ccccc3c(-c3ccccc3)c3c(-c4ccccc4)c4ccccc4c(-c4ccccc4)c23)cc1] | H22 |
| 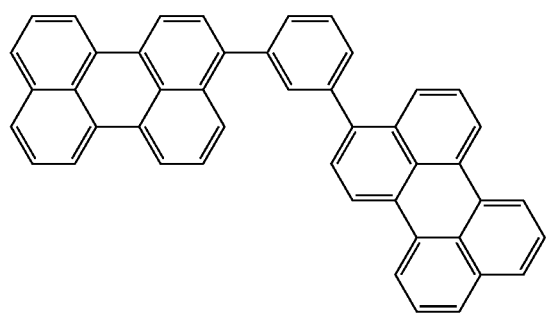 [SMILES: c1cc(-c2ccc3c4cccc5cccc(c6cccc2c63)c54)cc(-c2ccc3c4cccc5cccc(c6cccc2c63)c54)c1] | H23 |

TABLE 5-continued

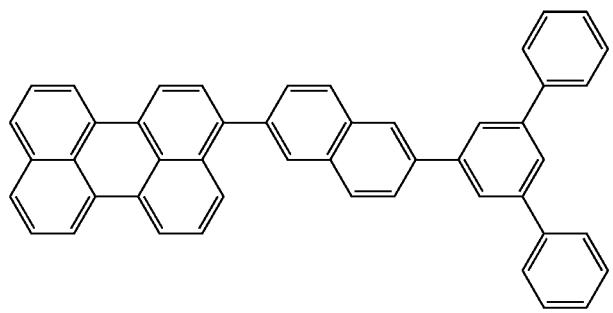 [SMILES: c1ccc(-c2cc(-c3ccccc3)cc(-c3ccc4cc(-c5ccc6c7cccc8cccc(c9cccc5c96)c87)ccc4c3)c2)cc1]
H24

Examples of the host include, but of course not limited to: condensed ring compounds (such as a fluorene derivative, a naphthalene derivative, an anthracene derivative, a pyrene derivative, a carbazole derivative, a quinoxaline derivative, and a quinoline derivative); an organic aluminum complex such as tris(8-quinolinolato)aluminum; an organic zinc complex; a triphenylamine derivative; and polymer derivatives such as a poly(fluorene) derivative and a poly(phenylene) derivative in addition to the group of compounds represented in Table 5 above.

The electron injectable/transportable material can be arbitrarily selected from materials that allow electrons to be easily injected from the cathode and can transport the injected electrons to the emission layer in consideration of, for example, the balance with the hole mobility of the hole transportable material. Examples of the material having electron-injecting performance and electron-transporting performance include an oxadiazole derivative, an oxazole derivative, a pyrazine derivative, a triazole derivative, a triazine derivative, a quinoline derivative, a quinoxaline derivative, a phenanthroline derivative, and an organic aluminum complex.

A constituent material for the anode desirably has as large a work function as possible. Examples thereof may include: metal simple substances such as gold, platinum, silver, copper, nickel, palladium, cobalt, selenium, vanadium, and tungsten or alloys obtained by combining these metal simple substances; metal oxides such as tin oxide, zinc oxide, indium oxide, indium tin oxide (ITO), and indium zinc oxide; and conductive polymers such as polyaniline, polypyrrole, and polythiophene.

One kind of those electrode substances may be used alone, or two or more kinds thereof may be used in combination. In addition, the anode may be of a single-layer construction or may be of a multilayer construction.

On the other hand, a constituent material for the cathode desirably has as small a work function as possible. Examples thereof include: metal simple substances such as alkali metals such as lithium; alkaline earth metals such as calcium; and aluminum, titanium, manganese, silver, lead, and chromium. Alternatively, alloys obtained by combining those metal simple substances can be used. For example, a magnesium-silver alloy, an aluminum-lithium alloy, or an aluminum-magnesium alloy can be used. A metal oxide such as indium tin oxide (ITO) can also be utilized. One kind of those electrode substances may be used alone, or two or more kinds thereof may be used in combination. In addition, the cathode may be of a single-layer construction or may be of a multilayer construction.

The organic compound layer (such as the hole injection layer, the hole transport layer, the electron-blocking layer, the emission layer, the hole-blocking layer, the electron transport layer, or the electron injection layer) for forming the organic light-emitting device of the present invention is formed by the following method.

A dry process such as a vacuum deposition method, an ionized vapor deposition method, sputtering, or a plasma process can be used for the formation of the organic compound layer for forming the organic light-emitting device of the present invention. In addition, a wet process involving dissolving the constituent materials in an appropriate solvent and forming a layer by a known application method (such as spin coating, dipping, a casting method, an LB method, or an ink jet method) can be used instead of the dry process.

Here, when the layer is formed by the vacuum deposition method, the solution application method, or the like, the layer hardly undergoes crystallization or the like and is excellent in stability over time. In addition, when the layer is formed by the application method, the film can be formed in combination with an appropriate binder resin.

Examples of the binder resin include, but not limited to, a polyvinyl carbazole resin, a polycarbonate resin, a polyester resin, an ABS resin, an acrylic resin, a polyimide resin, a phenol resin, an epoxy resin, a silicone resin, and a urea resin.

In addition, one kind of those binder resins may be used alone as a homopolymer or a copolymer, or two or more kinds thereof may be used as a mixture. Further, a known additive such as a plasticizer, an antioxidant, or a UV absorber may be used in combination as required.

(4) Application of Organic Light-Emitting Device

The organic light-emitting device of the present invention can be used as a constituent member for a display apparatus or lighting apparatus. In addition, the organic light-emitting device finds use in applications such as an exposure light source for an image-forming apparatus of an electrophotographic system, a backlight for a liquid crystal display apparatus, and a light-emitting apparatus including a white light source and a color filter. Examples of the color filter include filters that transmit light beams having three colors, i.e., red, green, and blue colors.

A display apparatus of the present invention includes the organic light-emitting device of the present invention in its display portion. It should be noted that the display portion includes multiple pixels.

In addition, the pixels each include the organic light-emitting device of the present invention and a transistor as an example of an active device (switching device) or amplifying device for controlling emission luminance, and the anode or cathode of the organic light-emitting device and the drain electrode or source electrode of the transistor are electrically connected to each other. Here, the display apparatus can be used as an image display apparatus for a PC or the like. The transistor is, for example, a TFT device and the TFT device is provided on, for example, the insulating surface of a substrate. In addition, the TFT device preferably includes an electrode formed of a transparent oxide semiconductor.

The display apparatus may be an image information processing apparatus that includes an image input portion for inputting image information from, for example, an area CCD, a linear CCD, or a memory card, and displays an input image on its display portion.

In addition, the display portion of an imaging apparatus or inkjet printer may have a touch panel function. The drive system of the touch panel function is not particularly limited.

In addition, the display apparatus may be used in the display portion of a multifunction printer.

A lighting apparatus is an apparatus for lighting, for example, the inside of a room. The lighting apparatus may emit light having any one of the following colors: a white color (having a color temperature of 4,200 K), a daylight color (having a color temperature of 5,000 K), and colors ranging from blue to red colors.

A lighting apparatus of the present invention includes the organic light-emitting device of the present invention and an AC/DC converter circuit (circuit for converting an AC voltage into a DC voltage) connected to the organic light-emitting device and supplying a driving voltage to the organic light-emitting device. It should be noted that the lighting apparatus may further include a color filter.

An image-forming apparatus of the present invention is an image-forming apparatus including: a photosensitive member; a charging portion for charging the surface of the photosensitive member; an exposure portion for exposing the photosensitive member to form an electrostatic latent image; and a developing unit for developing the electrostatic latent image formed on the surface of the photosensitive member. Here, the exposing unit to be provided in the image-forming apparatus includes the organic light-emitting device of the present invention.

In addition, the organic light-emitting device of the present invention can be used as a constituent member (light-emitting member) for an exposing machine for exposing a photosensitive member. An exposing machine including the organic light-emitting device of the present invention is, for example, an exposing machine in which a plurality of the organic light-emitting devices of the present invention are placed to form a line along a predetermined linear direction.

Next, the display apparatus of the present invention is described with reference to the drawing. The FIGURE is a schematic sectional view illustrating an example of a display apparatus including an organic light-emitting device and a switching device connected to the organic light-emitting device. It should be noted that the organic light-emitting device of the present invention is used as the organic light-emitting device constituting a display apparatus 1 of the FIGURE.

The display apparatus 1 of the FIGURE includes a substrate 11 made of glass or the like and a moisture-proof film 12 for protecting a TFT device 18 or organic compound layer as the switching device, the film being formed on the substrate. In addition, a metal gate electrode 13 is represented by reference numeral 13, a gate insulating film 14 is represented by reference numeral 14, and a semiconductor layer is represented by reference numeral 15.

The TFT device 18 includes the semiconductor layer 15, a drain electrode 16, and a source electrode 17. An insulating film 19 is formed on the TFT device 18. An anode 21 constituting the organic light-emitting device and the source electrode 17 are connected to each other through a contact hole 20.

It should be noted that a system for the electrical connection between the electrode (anode or cathode) in the organic light-emitting device and the electrode (source electrode or drain electrode) in the TFT is not limited to the aspect illustrated in the FIGURE. In other words, one of the anode and the cathode, and one of the source electrode and drain electrode of the TFT device have only to be electrically connected to each other.

Although multiple organic compound layers are illustrated like one layer in the display apparatus 1 of the FIGURE, an organic compound layer 22 may be multiple layers. A first protective layer 24 and second protective layer 25 for suppressing the deterioration of the organic light-emitting device are formed on a cathode 23.

When the display apparatus 1 of the FIGURE is a display apparatus that emits white light, an emission layer in the organic compound layer 22 in the FIGURE may be a layer obtained by mixing a red light-emitting material, a green light-emitting material, and a blue light-emitting material. In addition, the layer may be a laminated emission layer obtained by laminating a layer formed of the red light-emitting material, a layer formed of the green light-emitting material, and a layer formed of the blue light-emitting material. Further, alternatively, the following aspect is permitted: the layer formed of the red light-emitting material, the layer formed of the green light-emitting material, and the layer formed of the blue light-emitting material are, for example, arranged side by side to form domains in one emission layer.

Although the transistor is used as the switching device in the display apparatus 1 of the FIGURE, an MIM device may be used instead of the transistor as the switching device.

In addition, the transistor to be used in the display apparatus 1 of the FIGURE is not limited to a transistor using a monocrystalline silicon wafer and may be a thin-film transistor including an active layer on the insulating surface of a substrate. A thin-film transistor using monocrystalline silicon as the active layer, a thin-film transistor using non-monocrystalline silicon such as amorphous silicon or microcrystalline silicon as the active layer, or a thin-film transistor using a non-monocrystalline oxide semiconductor such as an indium zinc oxide or an indium gallium zinc oxide as the active layer is also permitted. It should be noted that the thin-film transistor is also called a TFT device.

The transistor in the display apparatus 1 of the FIGURE may be formed in a substrate such as an Si substrate. Here, the phrase "formed in a substrate" means that the transistor is produced by processing the substrate itself such as an Si substrate. In other words, the presence of the transistor in the substrate can be regarded as follows: the substrate and the transistor are integrally formed.

Whether the transistor is provided in the substrate is selected depending on definition. In the case of, for example, a definition of about a QVGA per inch, the organic light-emitting device is preferably provided in the Si substrate.

As described above, the driving of the display apparatus using the organic light-emitting device of the present invention enables display that has good image quality and is stable over a long time period.

EXAMPLES

Hereinafter, the present invention is described in detail by way of Examples, but the present invention is not limited to Examples described below.

Example 1 Synthesis of Exemplified Compound AA-1

Exemplified Compound AA-1 was synthesized according to the following synthesis scheme.

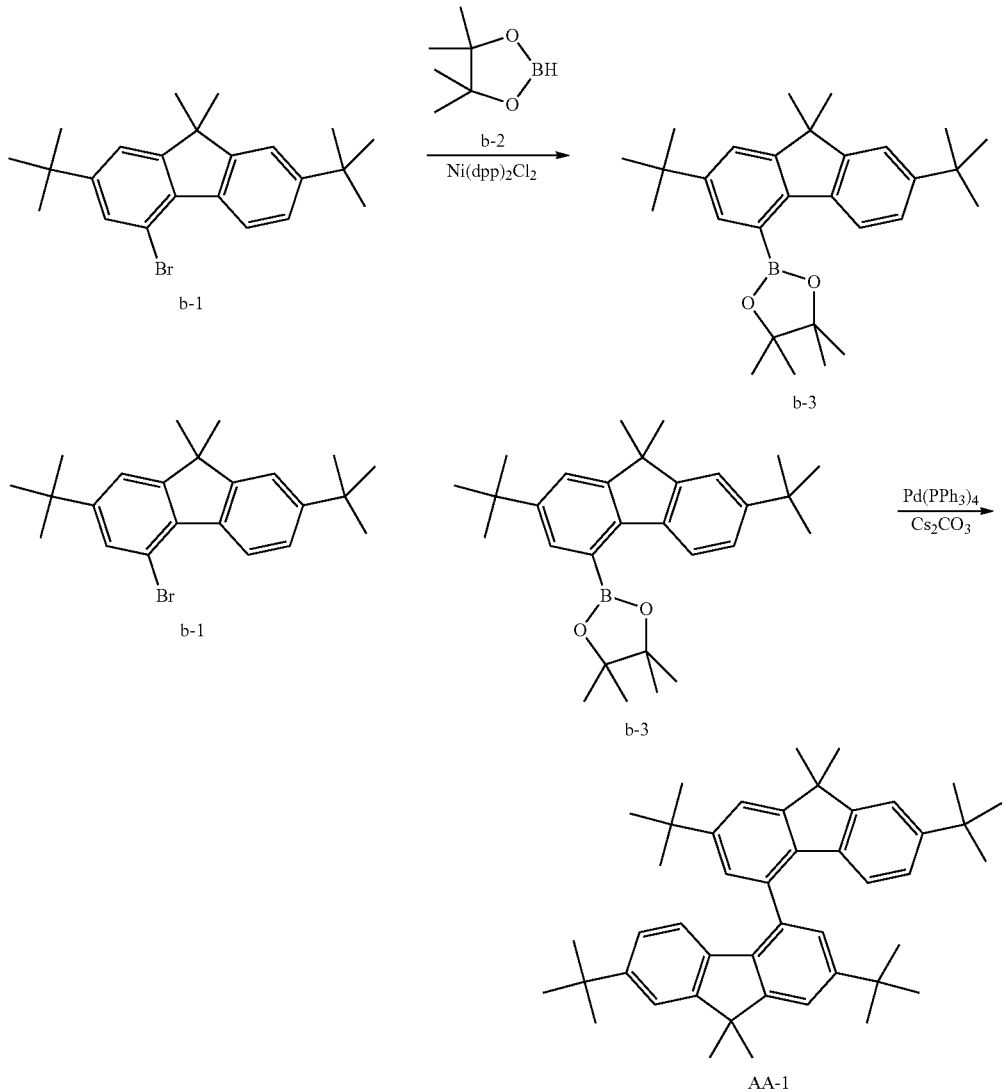

The details of the synthesis scheme are described below.
(1) Synthesis of Compound b-3
The following reagents and solvents were loaded into a 100-ml three-necked flask.
Compound b-1: 10.3 g (34.3 mmol)
[1,1'-Bis(diphenylphosphino)propane]dichloronickel: 1.88 g (3.43 mmol)
Compound b-2: 9.9 ml (68.5 mmol)
Toluene: 200 ml
Triethylamine: 30 ml Next, in a nitrogen atmosphere, the temperature of the reaction solution was increased to 90° C. and then the solution was stirred at the temperature (90° C.) for 6 hours. After the completion of the reaction, 200 ml of water were added to the resultant, and then an organic layer was extracted with toluene and dried with anhydrous sodium sulfate. Next, a crude product obtained by concentrating the organic layer under reduced pressure was purified by silica gel column chromatography (developing solvent: a mixed solvent of toluene and heptane) to provide 12.2 g (yield: 82%) of Compound b-3 as a white crystal.

(2) Synthesis of Exemplified Compound AA-1
The following reagents and solvents were loaded into a 100-ml three-necked flask.
Compound b-1: 2.50 g (6.50 mmol)
Compound b-3: 3.65 g (8.43 mmol)
Cesium carbonate: 6.35 g
Toluene: 30 ml
Ethanol: 10 ml
Water: 30 ml Next, in a nitrogen atmosphere, 376 mg of tetrakis(triphenylphosphine)palladium(0) were added while the reaction solution was stirred at room temperature. Next, the temperature of the reaction solution was increased to 80° C. and then the solution was stirred at the temperature (80° C.) for 5 hours. After the completion of the reaction, an organic layer was extracted with toluene and dried with anhydrous sodium sulfate. Next, a crude product obtained by concentrating the organic layer under reduced pressure was purified by silica gel column chromatography (developing solvent: a mixed solvent of toluene and heptane) to provide 3.70 g (yield: 93%) of Compound AA-1 as a white crystal.

Mass spectrometry confirmed 611 as the $M^+$ of Exemplified Compound AA-1. In addition, $^1$H-NMR measurement confirmed the structure of Exemplified Compound AA-1.

$^1$H-NMR (CDCl$_3$, 400 MHz) σ (ppm): 7.51 (s, 2H), 7.34-7.33 (m, 4H), 6.86 (d, 2H), 6.36 (s, 2H), 1.56 (s, 6H), 1.52 (s, 6H), 1.41 (s, 18H), 1.27 (s, 18H)

Example 2 Synthesis of Exemplified Compound AA-6

Exemplified Compound AA-6 was synthesized according to the following synthesis scheme.

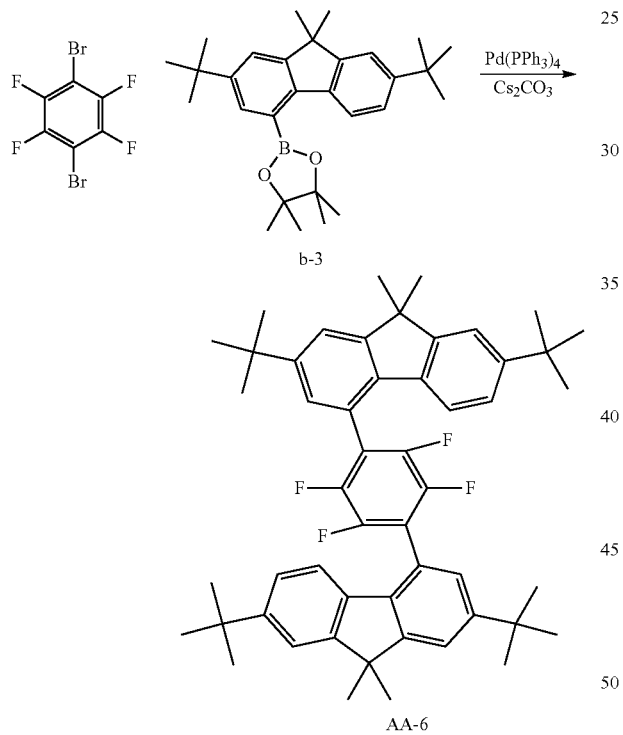

AA-6

The details of the synthesis scheme are described below.
The following reagents and solvents were loaded into a 100-ml three-necked flask.
1,4-Dibromo-2,3,5,6-tetrafluorobenzene: 1.0 g (3.3 mmol)
Compound b-3: 3.1 g (7.2 mmol)
Cesium carbonate: 9.3 g
Toluene: 30 ml
Ethanol: 15 ml
Water: 15 ml
Next, in a nitrogen atmosphere, 0.23 g of tetrakis(triphenylphosphine)palladium(0) was added while the reaction solution was stirred at room temperature. Next, the temperature of the reaction solution was increased to 90° C. and then the solution was stirred at the temperature (90° C.) for 5 hours. After the completion of the reaction, an organic layer was extracted with toluene and dried with anhydrous sodium sulfate. Next, a crude product obtained by concentrating the organic layer under reduced pressure was purified by silica gel column chromatography (developing solvent: a mixed solvent of toluene and heptane) to provide 1.9 g (yield: 77%) of Exemplified Compound AA-6 as a white crystal.

Mass spectrometry confirmed 759 as the $M^+$ of Exemplified Compound AA-6.

Example 3 Synthesis of Exemplified Compound AA-8

Exemplified Compound AA-8 was synthesized according to the following synthesis scheme.

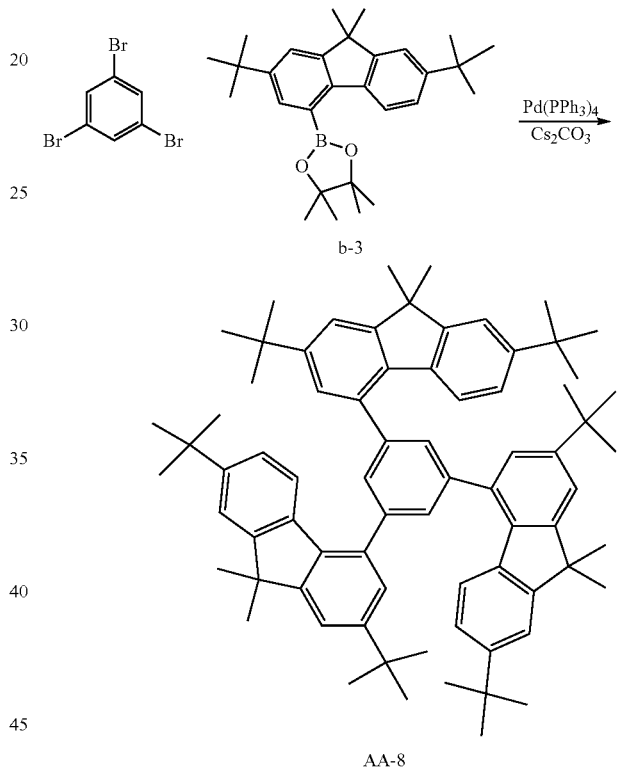

AA-8

The details of the synthesis scheme are described below.
The following reagents and solvents were loaded into a 100-ml three-necked flask.
1,3,5-Tribromobenzene: 0.630 g (2.00 mmol)
Compound b-3: 3.46 g (8.00 mmol)
Cesium carbonate: 7.0 g
Toluene: 30 ml
Ethanol: 10 ml
Water: 30 ml
Next, in a nitrogen atmosphere, 231 mg of tetrakis(triphenylphosphine)palladium(0) were added while the reaction solution was stirred at room temperature. Next, the temperature of the reaction solution was increased to 80° C. and then the solution was stirred at the temperature (80° C.) for 5 hours. After the completion of the reaction, an organic layer was extracted with toluene and dried with anhydrous sodium sulfate. Next, a crude product obtained by concentrating the organic layer under reduced pressure was purified by silica gel column chromatography (developing solvent: a mixed solvent of chloroform and heptane) to provide 0.85 g (yield: 43%) of Exemplified Compound AA-8 as a white crystal.

Mass spectrometry confirmed 991 as the M⁺ of Exemplified Compound AA-8.

Example 4 Synthesis of Exemplified Compound AA-9

Exemplified Compound AA-9 was synthesized according to the following synthesis scheme.

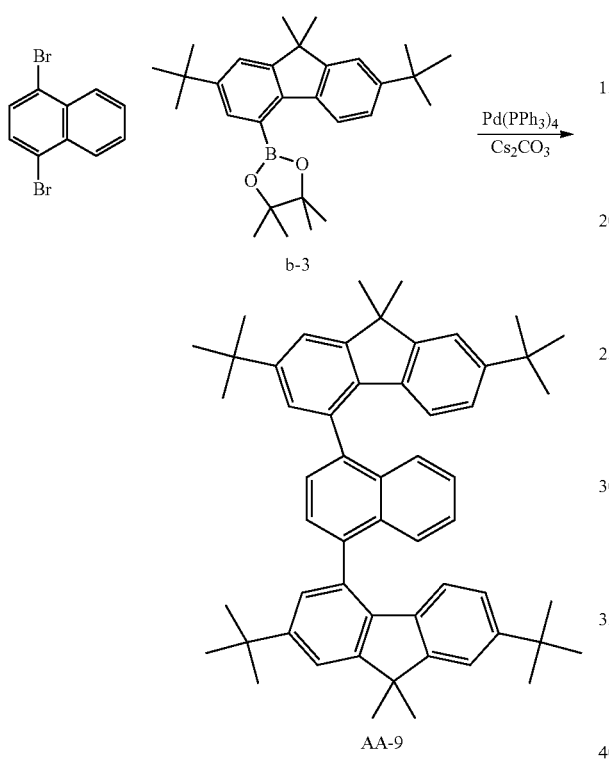

AA-9

The details of the synthesis scheme are described below.
The following reagents and solvents were loaded into a 100-ml three-necked flask.
1,4-Dibromonaphthalene: 0.66 g (2.31 mmol)
Compound b-3: 2 g (4.62 mmol)
Cesium carbonate: 3.01 g
Toluene: 40 ml
Ethanol: 20 ml
Water: 7 ml Next, in a nitrogen atmosphere, 267 mg of tetrakis(triphenylphosphine)palladium(0) were added while the reaction solution was stirred at room temperature. Next, the temperature of the reaction solution was increased to 80° C. and then the solution was stirred at the temperature (80° C.) for 5 hours. After the completion of the reaction, an organic layer was extracted with toluene and dried with anhydrous sodium sulfate. Next, a crude product obtained by concentrating the organic layer under reduced pressure was purified by silica gel column chromatography (developing solvent: a mixed solvent of toluene and heptane) to provide 1.65 g (yield: 97%) of Exemplified Compound AA-9 as a white crystal.

Mass spectrometry confirmed 737 as the M⁺ of Exemplified Compound AA-9. In addition, ¹H-NMR measurement confirmed the structure of Exemplified Compound AA-9.

¹H-NMR (CDCl₃, 400 MHz) σ (ppm): 7.70-7.67 (q, 2H), 7.63 (s, 2H), 7.54 (s, 2H), 7.42 (s, 2H), 7.37 (s, 2H), 7.32-7.28 (q, 2H), 6.90 (d, 2H), 6.48 (d, 2H), 1.61 (s, 6H), 1.59 (s, 6H), 1.44 (s, 18H), 1.30 (s, 18H)

Example 5 Synthesis of Exemplified Compound AA-7

Exemplified Compound AA-7 was synthesized according to the following synthesis scheme.

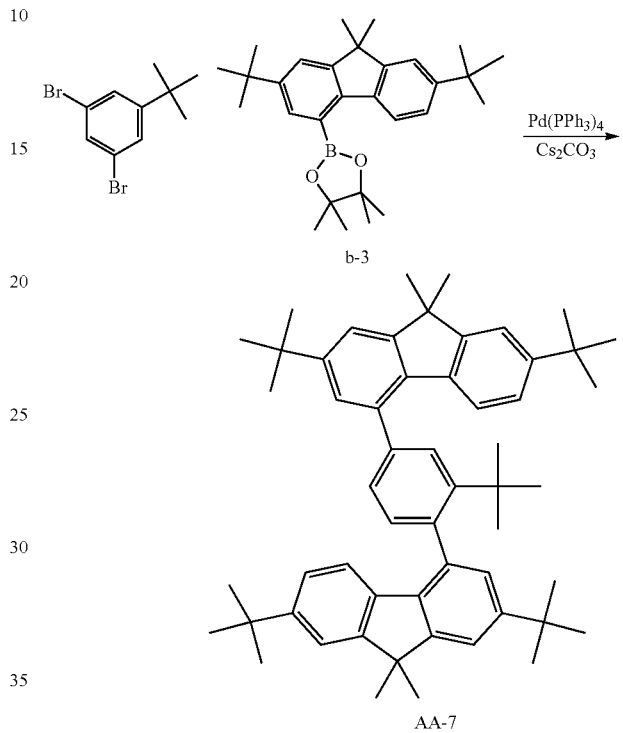

AA-7

The details of the synthesis scheme are described below.
The following reagents and solvents were loaded into a 100-ml three-necked flask.
1-tert-Butyl-3,5-dibromobenzene: 0.675 g (2.31 mmol)
Compound b-3: 2 g (4.62 mmol)
Cesium carbonate: 3.0 g
Toluene: 40 ml
Ethanol: 20 ml
Water: 7 ml Next, in a nitrogen atmosphere, 267 mg of tetrakis(triphenylphosphine)palladium(0) were added while the reaction solution was stirred at room temperature. Next, the temperature of the reaction solution was increased to 80° C. and then the solution was stirred at the temperature (80° C.) for 4 hours. After the completion of the reaction, an organic layer was extracted with toluene and dried with anhydrous sodium sulfate. Next, a crude product obtained by concentrating the organic layer under reduced pressure was purified by silica gel column chromatography (developing solvent: a mixed solvent of chloroform and heptane) to provide 1.42 g (yield: 83%) of Exemplified Compound AA-7 as a white crystal.

Mass spectrometry confirmed 743 as the M⁺ of Exemplified Compound AA-7.

Example 6 Synthesis of Exemplified Compound AA-20

Exemplified Compound AA-20 was synthesized according to the following synthesis scheme. It should be noted that tBu represents a tert-butyl group.

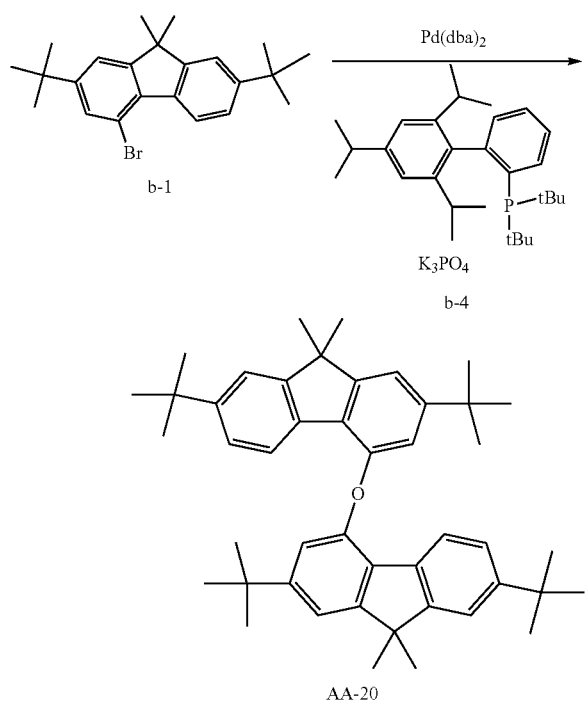

The details of the synthesis scheme are described below.
The following reagents and solvents were loaded into a 100-ml three-necked flask.

Compound b-1: 1.0 g (2.60 mmol)
Compound b-4: 0.11 g (0.26 mmol)
Potassium phosphate: 0.55 g
Dioxane: 10 ml
Water: 10 ml Next, in a nitrogen atmosphere, 75 mg of palladium dibenzylideneacetone were added while the reaction solution was stirred at room temperature. Next, the temperature of the reaction solution was increased to 80° C. and then the solution was stirred at the temperature (80° C.) for 5 hours. After the completion of the reaction, an organic layer was extracted with toluene and dried with anhydrous sodium sulfate. Next, a crude product obtained by concentrating the organic layer under reduced pressure was purified by silica gel column chromatography (developing solvent: a mixed solvent of chloroform and heptane) to provide 33 mg of Exemplified Compound AA-20 as a white crystal.

Mass spectrometry confirmed 627 as the $M^+$ of Exemplified Compound AA-20. In addition, $^1$H-NMR measurement confirmed the structure of Exemplified Compound AA-20.

$^1$H-NMR (CDCl$_3$, 400 MHz) σ (ppm): 8.04 (d, 2H), 7.44 (s, 2H), 7.28 (d, 2H), 7.16 (s, 2H), 6.94 (s, 2H), 1.56 (s, 6H), 1.54 (s, 6H), 1.37 (s, 18H), 1.27 (s, 18H)

Example 7 Synthesis of Exemplified Compound AA-2

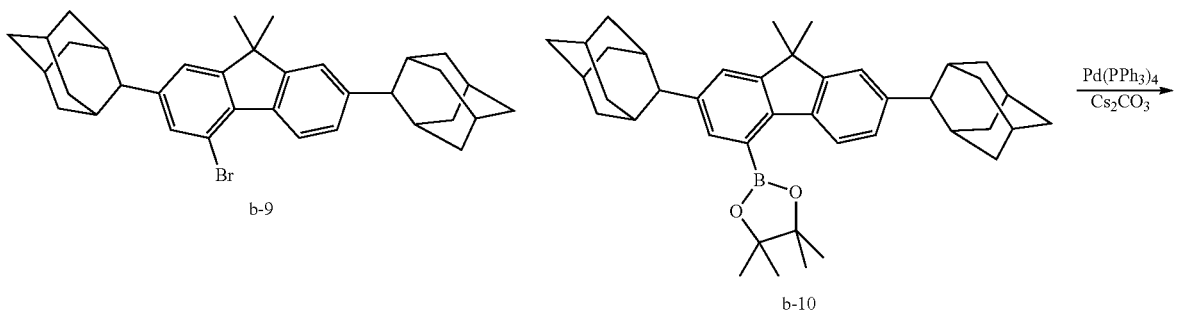

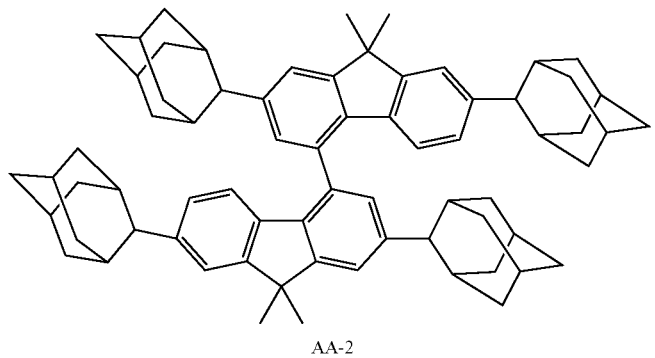

Exemplified Compound AA-2 was synthesized by the same method as that of Example 1 except that: Compound b-10 was synthesized by using Compound b-9 instead of Compound b-1 in the section (1) of Example 1; and Compound b-9 was used instead of Compound b-1 and Compound b-10 was used instead of Compound b-3 in the section (2) of Example 1.

Mass spectrometry confirmed 923 as the M⁺ of Exemplified Compound AA-2.

Example 8 Synthesis of Exemplified Compound AA-13

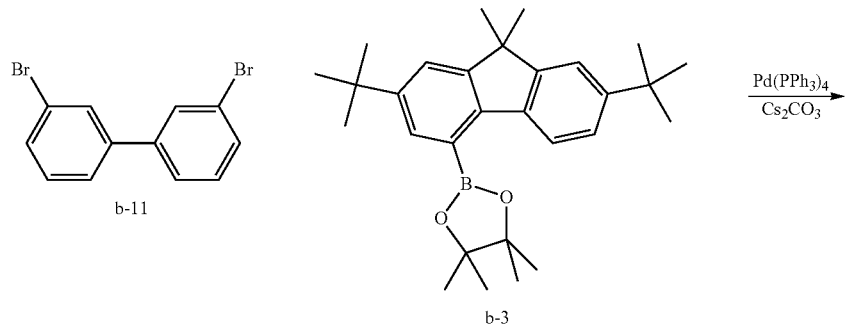

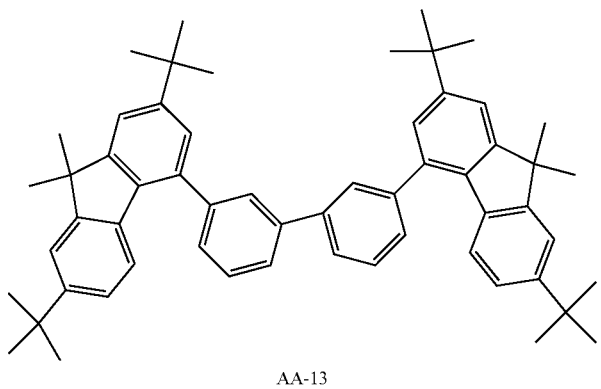

Exemplified Compound AA-13 was synthesized by the same method as that of Example 1 except that Compound b-11 (1,4-dibromonaphthalene) was used instead of Compound b-1 in the section (2) of Example 1.

Mass spectrometry confirmed 763 as the M⁺ of Exemplified Compound AA-13.

Example 9 Synthesis of Exemplified Compound AA-28

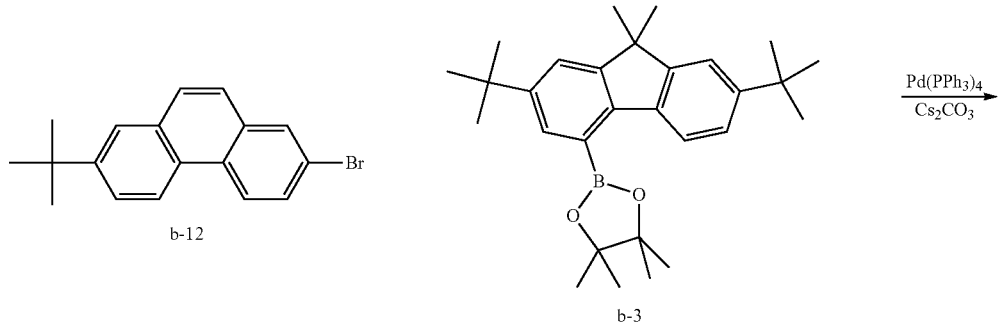

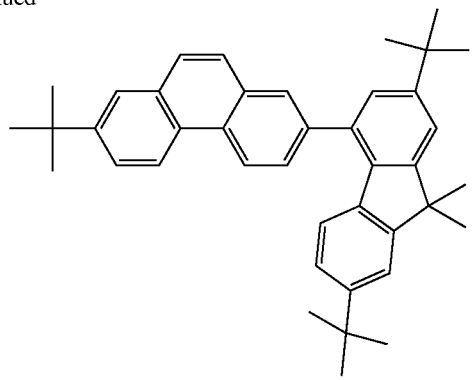
AA-28
Exemplified Compound AA-28 was synthesized by the same method as that of Example 1 except that Compound b-12 was used instead of Compound b-1 in the section (2) of Example 1.
Mass spectrometry confirmed 538 as the $M^+$ of Exemplified Compound AA-28.
Example 10 Synthesis of Exemplified Compound AA-35
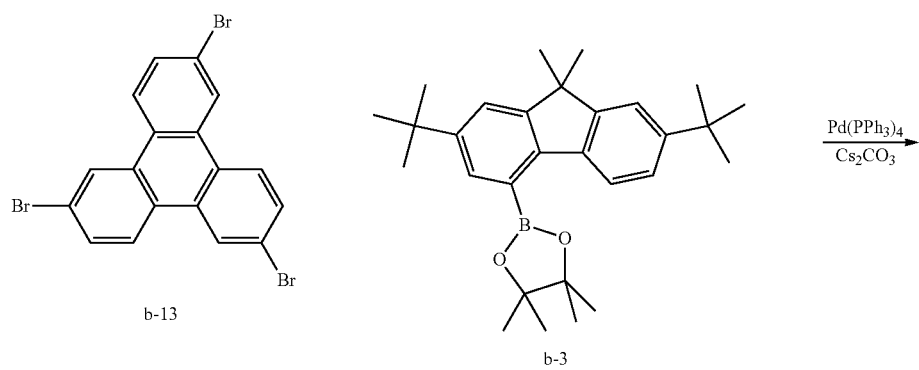
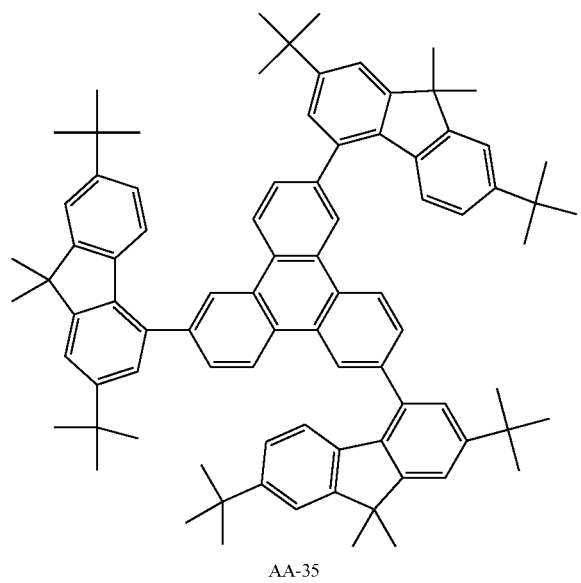
AA-35

Exemplified Compound AA-35 was synthesized by the same method as that of Example 1 except that Compound b-13 (1,3,5-tribromobenzene) was used instead of Compound b-1 in the section (2) of Example 1.

Mass spectrometry confirmed 1,141 as the M+ of Exemplified Compound AA-35.

Synthesis of Comparative Compound AZ-1

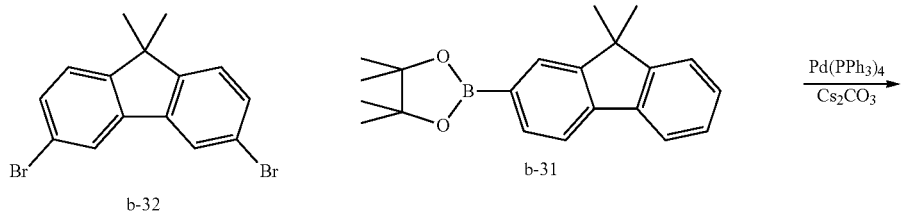

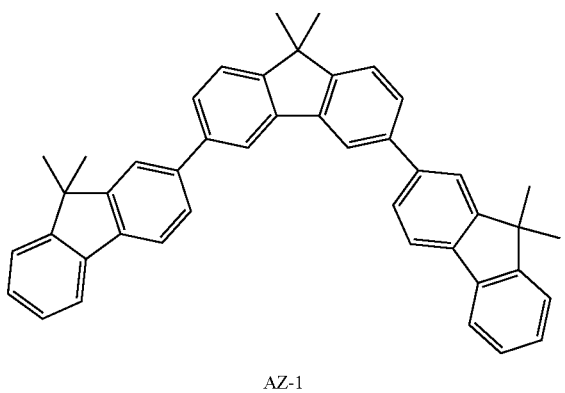

Comparative Compound AZ-1 was synthesized by the same method as that of Example 4 except that Compound b-32 was used instead of 1,4-dibromonaphthalene and Compound b-31 was used instead of Compound b-3 in Example 4. Mass spectrometry confirmed 578 as the M+ of Comparative Compound AZ-1.

[Synthesis Example 1] Synthesis of Exemplified Compound AB-3

Exemplified Compound AB-3 was synthesized according to the following synthesis scheme.

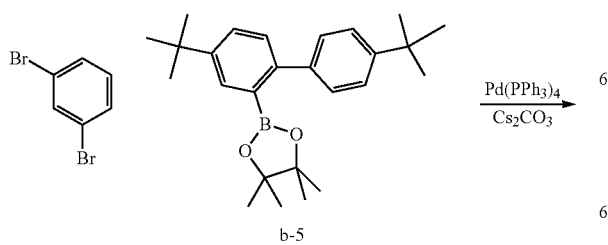

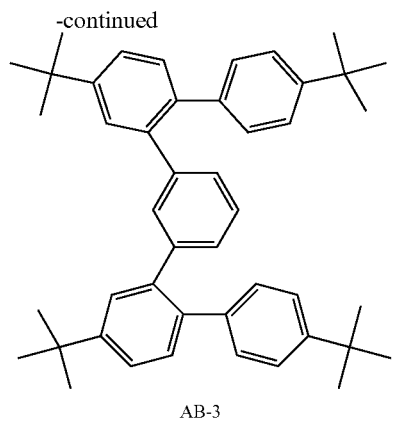

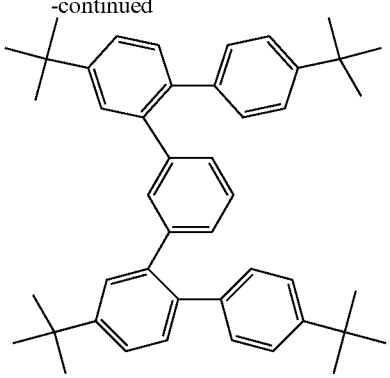

The details of the synthesis scheme are described below.
The following reagents and solvents were loaded into a 100-ml three-necked flask.
3,5-Dibromobenzene: 0.708 g (3.00 mmol)
Compound b-5: 2.71 g (7.00 mmol)
Cesium carbonate: 3.9 g
Toluene: 30 ml
Ethanol: 10 ml
Water: 30 ml Next, in a nitrogen atmosphere, 173 mg of tetrakis(triphenylphosphine)palladium(0) were added while the reaction solution was stirred at room temperature. Next, the temperature of the reaction solution was increased to 80° C. and then the solution was stirred at the temperature (80° C.) for 5 hours. After the completion of the reaction, an organic layer was extracted with toluene and dried with anhydrous sodium sulfate. Next, a crude product obtained by concentrating the organic layer under reduced pressure was purified by silica gel column chromatography (developing solvent: a mixed solvent of chloroform and heptane) to provide 1.56 g (yield: 86%) of Compound AB-3 as a white crystal.

Mass spectrometry confirmed 607 as the M⁺ of Exemplified Compound AB-3.

[Synthesis Example 2] Synthesis of Exemplified Compound AC-6

Exemplified Compound AC-6 was synthesized according to the following synthesis scheme.

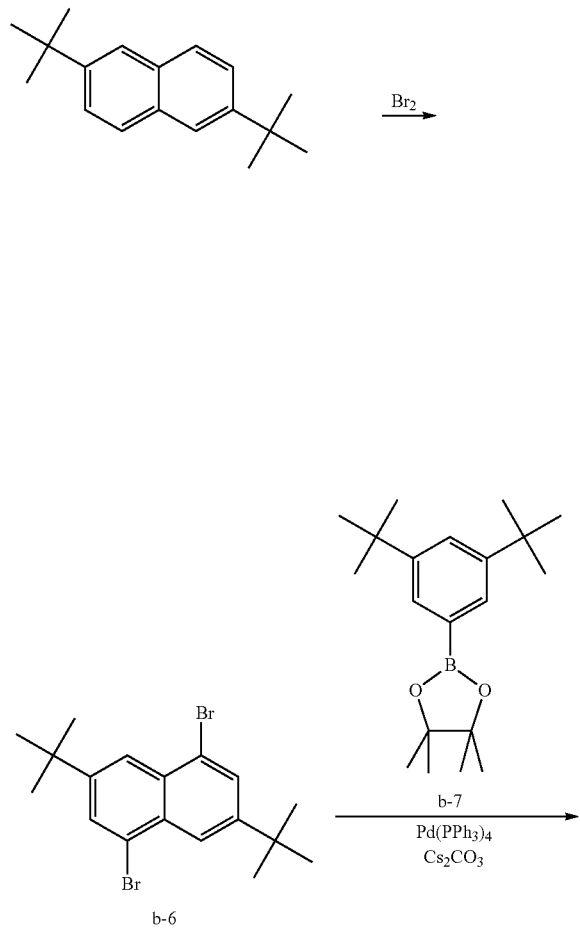

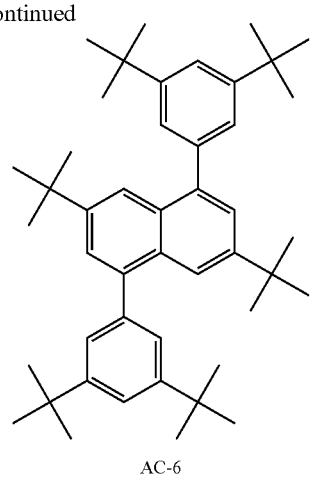

AC-6

The details of the synthesis scheme are described below.
(1) Synthesis of Compound b-6

The following reagents and solvent were loaded into a 100-ml three-necked flask.

2,6-Di-tert-butylnaphthalene: 1.0 g (4.17 mmol)
Bromine: 9.60 ml
Chloroform: 30 ml Next, the temperature of the reaction solution was increased to 65° C. and then the solution was stirred at the temperature (65° C.) for 3.5 hours. After the completion of the reaction, an organic layer was extracted with chloroform and dried with anhydrous sodium sulfate. Next, the organic layer was concentrated under reduced pressure and then 30 ml of methanol were added to the concentrate to precipitate a crystal. The crystal was filtered to provide 1.23 g (yield: 76%) of Compound b-6 as a white crystal.

(2) Synthesis of Exemplified Compound AC-6

The following reagents and solvents were loaded into a 100-ml three-necked flask.

Compound b-6: 0.750 g (1.89 mmol)
Compound b-7: 1.80 g (3.16 mmol)
Cesium carbonate: 3.69 g
Toluene: 20 ml
Ethanol: 10 ml
Water: 20 ml Next, in a nitrogen atmosphere, 109 mg of tetrakis (triphenylphosphine) palladium(0) were added while the reaction solution was stirred at room temperature. Next, the temperature of the reaction solution was increased to 80° C. and then the solution was stirred at the temperature (80° C.) for 5 hours. After the completion of the reaction, an organic layer was extracted with toluene and dried with anhydrous sodium sulfate. Next, a crude product obtained by concentrating the organic layer under reduced pressure was purified by silica gel column chromatography (developing solvent: a mixed solvent of chloroform and heptane) to provide 0.75 g (yield: 65%) of Exemplified Compound AC-6 as a white crystal.

Mass spectrometry confirmed 617 as the M⁺ of Exemplified Compound AC-6. In addition, ¹H-NMR measurement confirmed the structure of Exemplified Compound AC-6.

¹H-NMR (CDCl₃, 400 MHz) σ (ppm): 7.88 (s, 2H), 7.55 (s, 2H), 7.49 (s, 2H), 7.42 (s, 2H), 7.41 (s, 2H), 1.41 (s, 36H), 1.33 (s, 18H)

[Synthesis Example 3] Synthesis of Exemplified Compound AB-7

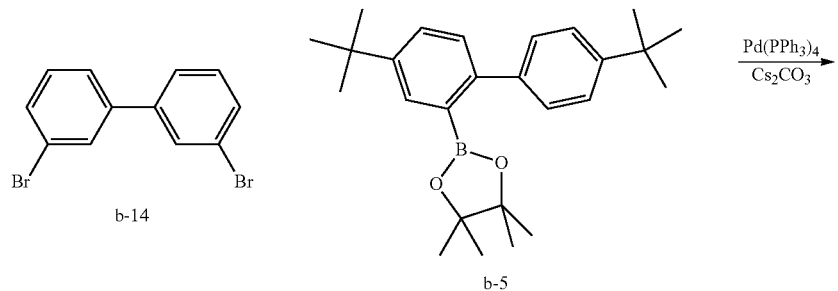

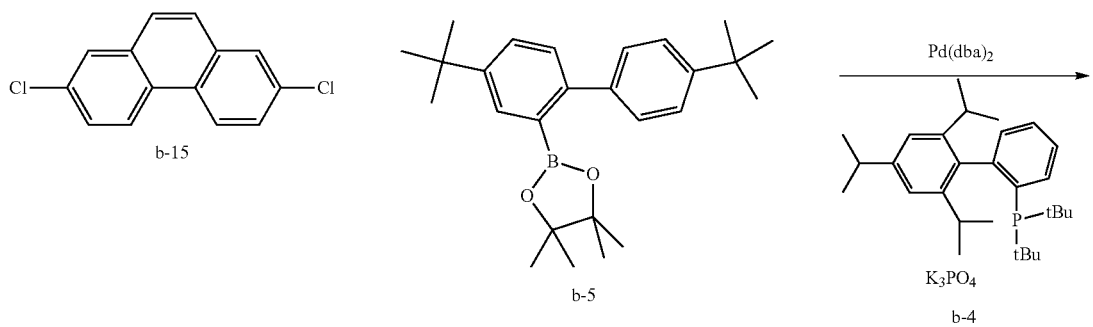

AB-7

Exemplified Compound AB-7 was synthesized by the same method as that of Synthesis Example 1 except that Compound b-14 was used instead of 1,3-dibromobenzene in Synthesis Example 1.

Mass spectrometry confirmed 683 as the $M^+$ of Exemplified Compound AB-7.

[Synthesis Example 4] Synthesis of Exemplified Compound AB-6

Exemplified Compound AB-6 was synthesized according to the following synthesis scheme.

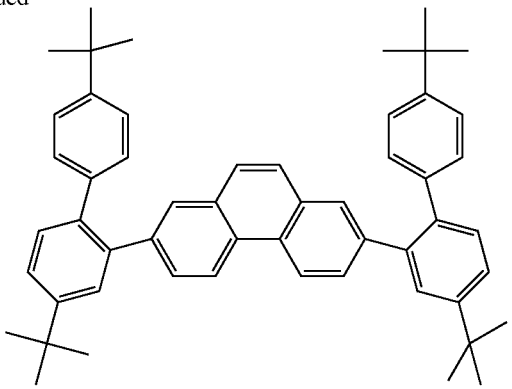

AB-6

The details of the synthesis scheme are described below.
The following reagents and solvents were loaded into a 100-ml three-necked flask.
Compound b-15: 0.25 g (1.0 mmol)
Compound b-5: 1.0 g (2.60 mmol)
Compound b-4: 0.11 g (0.26 mmol)
Potassium phosphate: 0.55 g
Dioxane: 10 ml
Water: 10 ml Next, in a nitrogen atmosphere, 75 mg of palladium dibenzylideneacetone were added while the reaction solution was stirred at room temperature. Next, the temperature of the reaction solution was increased to 80° C. and then the solution was stirred at the temperature (80° C.) for 5 hours. After the completion of the reaction, an organic layer was extracted with toluene and dried with anhydrous sodium sulfate. Next, a crude product obtained by concentrating the organic layer under reduced pressure was purified by silica gel column chromatography (developing solvent: a mixed solvent of chloroform and heptane) to provide 0.37 g (yield: 53%) of Exemplified Compound AB-6 as a white crystal.

Mass spectrometry confirmed 707 as the M⁺ of Exemplified Compound AB-6.

Example 11

In this example, an organic light-emitting device in which an anode, a hole transport layer, an emission layer, a hole-blocking layer, an electron transport layer, and a cathode were formed in the stated order on a substrate was produced by a method described below. Here, part of the compounds used in this example are listed below.

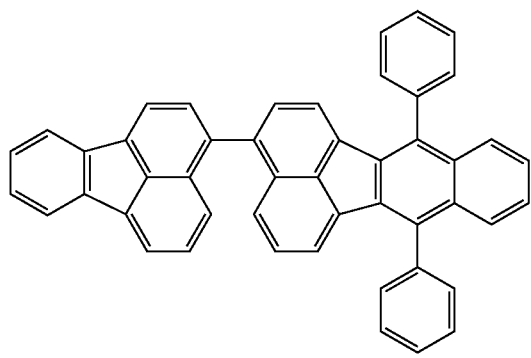

c-1

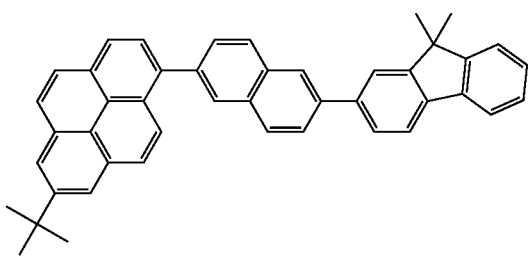

c-2

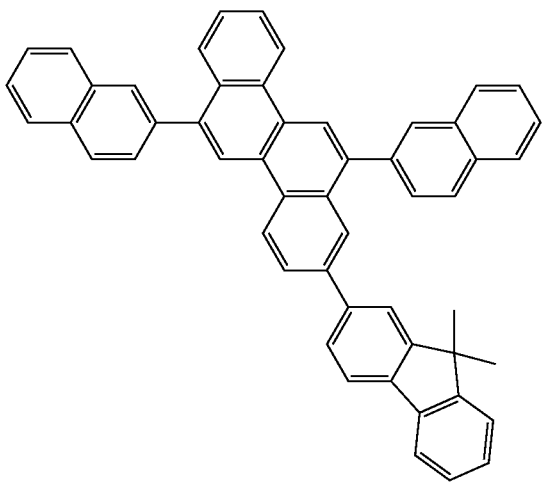

c-3

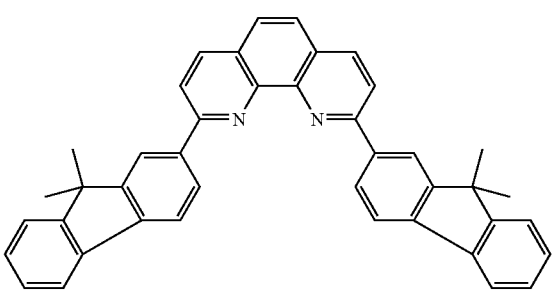

c-4

Indium tin oxide (ITO) was formed into a film on a glass substrate by a sputtering method. Thus, the anode was formed. At this time, the thickness of the anode was set to 120 nm. Next, the substrate with the anode formed thereon was sequentially subjected to ultrasonic washing with acetone and ultrasonic washing with isopropyl alcohol (IPA), and was then subjected to boil washing with IPA, followed by drying. Further, the dried product was subjected to UV/ozone washing, and the resultant was used as a transparent conductive supporting substrate in the following steps.

Next, Exemplified Compound AC-6 (hereinafter referred to as "compound A") and chloroform were mixed to prepare a material solution A having a concentration of 0.25 wt %. In addition, BC-4 (hereinafter referred to as "compound B") and chloroform were mixed to prepare a material solution B having a concentration of 0.25 wt %.

Next, a mixed liquid was prepared by mixing the material solution A and the material solution B so that their weight ratio became 2:1.

Next, the mixed liquid was dropped onto the anode (ITO electrode) and then a thin film was formed by spin coating at 500 RPM for 10 seconds and then at 1,000 RPM for 1 minute. After that, the solvent in the thin film was completely removed by drying the thin film in a vacuum oven at 80° C. for 10 minutes. Thus, the hole transport layer was formed. At this time, the thickness of the hole transport layer was 30 nm.

Next, organic compound layers and electrode layers shown in Table 6 below were continuously formed on the hole transport layer by a vacuum deposition method involving using resistance heating in a vacuum chamber at $1 \times 10^{-5}$ Pa to produce the organic light-emitting device.

TABLE 6

|  | Constituent material | Thickness [nm] |
|---|---|---|
| Emission layer | c-2 (host) c-1 (guest) (host:guest = 95:5 (weight ratio)) | 20 |
| Hole-blocking layer | c-3 | 10 |
| Electron transport layer | c-4 | 50 |
| First electrode layer (cathode) | LiF | 0.5 |
| Second electrode layer (cathode) | Al | 150 |

A current was passed through the resultant organic light-emitting device, and then its emission characteristics when its emission luminance was set to 2,000 cd/m² were measured and evaluated. As a result, the device had an emission efficiency (cd/A) of 13.0 cd/A and an external quantum yield of 7.5%. In addition, the device had CIE chromaticity coordinates of (0.16, 0.26) and was observed to emit blue light satisfactorily.

Examples 12 to 17

Organic light-emitting devices were each produced by the same method as that of Example 11 except that the compound A and the compound B were changed to compounds shown in Table 7 below in Example 11. In addition, the resultant organic light-emitting devices were evaluated by the same method as that of Example 11. Table 7 shows the results.

Examples 18 to 20

Organic light-emitting devices were each produced by the same method as that of Example 11 except that Exemplified Compound AA-1 was used as the compound A and the compound B was changed to a compound shown in Table 7 below in Example 11. In addition, the resultant organic light-emitting devices were evaluated by the same method as that of Example 11. Table 7 shows the results.

TABLE 7

|  | Compound A | Compound B | Emission efficiency [cd/A] | External quantum yield [%] | Chromaticity coordinates [x, y] |
|---|---|---|---|---|---|
| Example 11 | AC-6 | BC-4 | 13.0 | 7.5 | (0.15, 0.26) |
| Example 12 | AA-1 | BC-4 | 11.7 | 6.5 | (0.16, 0.26) |
| Example 13 | AA-7 | BC-4 | 11.3 | 6.3 | (0.16, 0.26) |
| Example 14 | AA-9 | BC-4 | 11.1 | 6.2 | (0.15, 0.26) |
| Example 15 | AB-3 | BC-4 | 12.3 | 6.9 | (0.16, 0.25) |
| Example 16 | AB-7 | BC-4 | 11.5 | 6.6 | (0.15, 0.25) |
| Example 17 | AB-6 | BC-4 | 12.1 | 6.8 | (0.15, 0.25) |
| Example 18 | AA-1 | BB-4 | 8.7 | 4.7 | (0.16, 0.26) |
| Example 19 | AA-1 | BF-1 | 8.9 | 5.0 | (0.16, 0.26) |
| Example 20 | AA-1 | BF-2 | 8.8 | 4.9 | (0.16, 0.26) |

Comparative Examples 1 to 3

Organic light-emitting devices were each produced by the same method as that of Example 11 except that the compound A and the compound B were changed to compounds shown in Table 8 below in Example 11. In addition, the resultant organic light-emitting devices were evaluated by the same method as that of Example 11. Table 8 shows the results.

Comparative Example 4

An organic light-emitting device was produced by the same method as that of Example 11 except that the hole transport layer was formed using only the material solution B in Example 11. In addition, the resultant organic light-emitting device was evaluated by the same method as that of Example 11. Table 8 shows the results.

Comparative Examples 5 to 7

Organic light-emitting devices were each produced by the same method as that of Comparative Example 4 except that the compound B was changed to a compound shown in Table 8 below in Comparative Example 4. In addition, the resultant organic light-emitting devices were evaluated by the same method as that of Example 11. Table 8 shows the results.

TABLE 8

|  | Compound A | Compound B | Emission efficiency [cd/A] | External quantum yield [%] | Chromaticity coordinates [x, y] |
|---|---|---|---|---|---|
| Comparative Example 1 | AZ-1 | BC-4 | 8.8 | 4.9 | (0.16, 0.24) |
| Comparative Example 2 | AZ-2 | BC-4 | AZ-2 emitted light. | | |
| Comparative Example 3 | AZ-3 | BC-4 | 7.8 | 4.3 | (0.15, 0.25) |
| Comparative Example 4 | — | BC-4 | 8.3 | 4.7 | (0.15, 0.25) |
| Comparative Example 5 | — | BB-4 | 3.2 | 1.8 | (0.15, 0.25) |

TABLE 8-continued

|  | Compound A | Compound B | Emission efficiency [cd/A] | External quantum yield [%] | Chromaticity coordinates [x, y] |
|---|---|---|---|---|---|
| Comparative Example 6 | — | BF-1 | 2.4 | 1.3 | (0.15, 0.25) |
| Comparative Example 7 | — | BF-2 | 2.2 | 1.2 | (0.15, 0.25) |

Example 21

In this example, an organic light-emitting device was produced. An organic light-emitting device in which an anode, a hole transport layer, an emission layer, a hole-blocking layer, an electron transport layer, and a cathode were formed in the stated order on a substrate was produced by a method described below. Here, part of the compounds used in this example are listed below.

c-1

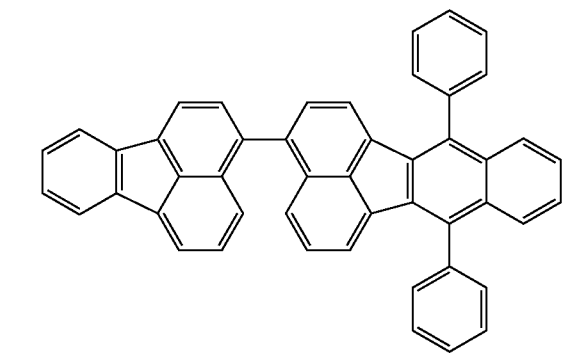

c-5

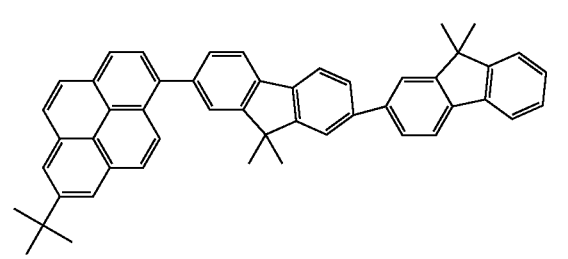

c-6

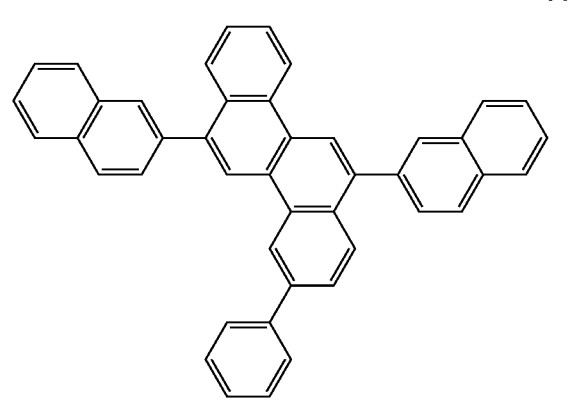

c-7

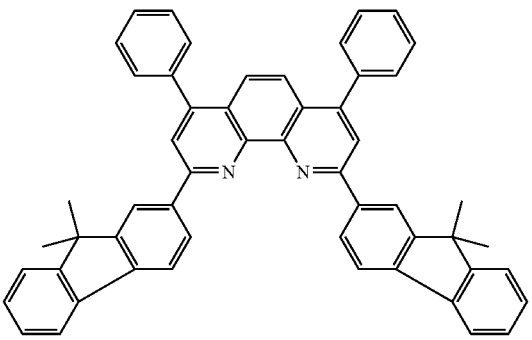

First, a transparent conductive supporting substrate was produced by the same method as that of Example 11.

Next, a chloroform solution having a concentration of 0.25 wt % was prepared by mixing Exemplified Compound AA-1 and chloroform. Next, the chloroform solution was dropped onto the anode (ITO electrode) and then a thin film was formed by spin coating at 500 RPM for 10 seconds and then at 1,000 RPM for 1 minute. After that, the solvent in the thin film was completely removed by drying the thin film in a vacuum oven at 80° C. for 10 minutes. Thus, the hole transport layer was formed. At this time, the thickness of the hole transport layer was 30 nm.

Next, organic compound layers and electrode layers shown in Table 9 below were continuously formed on the hole transport layer by a vacuum deposition method involving using resistance heating in a vacuum chamber at $1 \times 10^{-5}$ Pa to produce the organic light-emitting device.

TABLE 9

|  | Constituent material | Thickness [nm] |
|---|---|---|
| Emission layer | c-5 (host) c-1 (guest) (host:guest = 95:5 (weight ratio)) | 20 |
| Hole-blocking layer | c-6 | 40 |
| Electron transport layer | c-7 | 40 |
| First electrode layer (cathode) | LiF | 0.5 |
| Second electrode layer (cathode) | Al | 150 |

A current was passed through the resultant organic light-emitting device, and then its emission characteristics when its emission luminance was set to 2,000 cd/m² were measured and evaluated. As a result, the device had an emission efficiency (cd/A) of 7.2 cd/A and was observed to emit blue light satisfactorily.

Example 22

An organic light-emitting device was produced by the same method as that of Example 21 except that Exemplified Compound AA-20 was used instead of Exemplified Compound AA-1 in Example 21. The emission characteristics of the organic light-emitting device were measured and evaluated by the same method as that of Example 21. As a result, the device had an emission efficiency (cd/A) of 8.0 cd/A and was observed to emit blue light satisfactorily.

Example 23

An organic light-emitting device was produced by the same method as that of Example 21 except that Exemplified Compound AA-35 was used instead of Exemplified Compound AA-1 in Example 21. The emission characteristics of the organic light-emitting device were measured and evaluated by the same method as that of Example 21. As a result, the device had an emission efficiency (cd/A) of 7.1 cd/A and was observed to emit blue light satisfactorily.

Example 24

Part of the compounds used in this example are listed below.

d-1

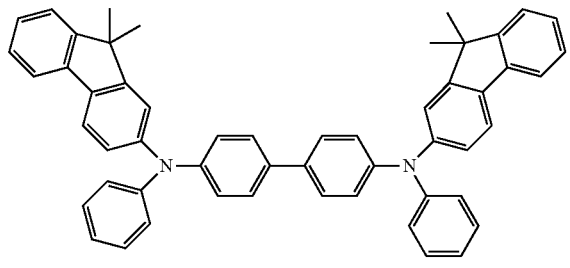

d-2

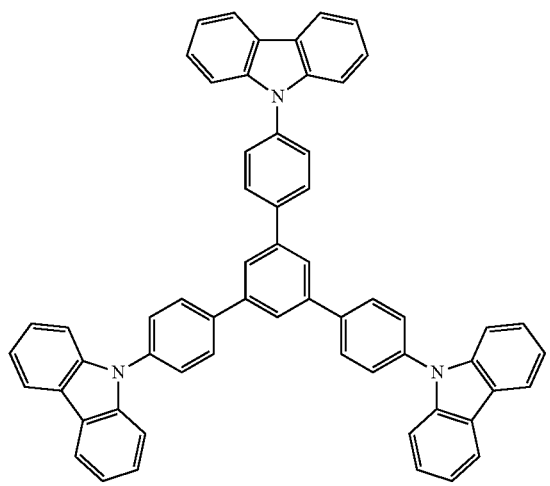

d-3

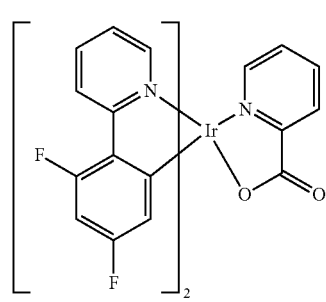

d-4 d-5

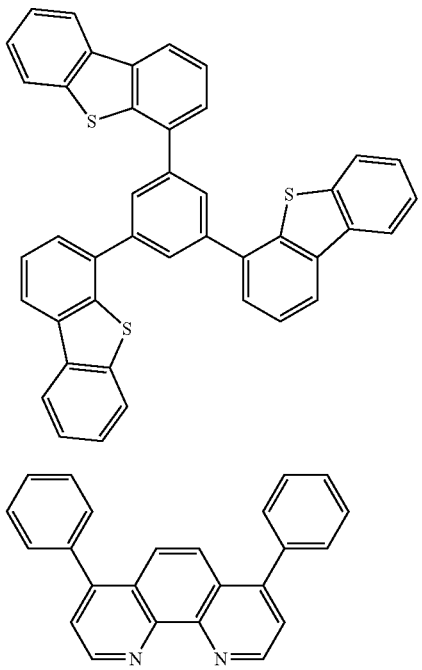

Indium tin oxide (ITO) was formed into a film on a glass substrate by a sputtering method. Thus, an anode was formed. At this time, the thickness of the anode was set to 120 nm. Next, the substrate with the anode formed thereon was sequentially subjected to ultrasonic washing with acetone and ultrasonic washing with isopropyl alcohol (IPA), and was then subjected to boil washing with IPA, followed by drying. Further, the dried product was subjected to UV/ozone washing, and the resultant was used as a transparent conductive supporting substrate in the following steps.

Next, organic compound layers and electrode layers shown in Table 10 below were continuously formed by a vacuum deposition method involving using resistance heating in a vacuum chamber at $1\times10^{-5}$ Pa to produce an organic light-emitting device.

TABLE 10

| | Constituent material | Thickness [nm] |
|---|---|---|
| Hole injection layer | d-1 | 40 |
| Hole transport layer | d-2 | 10 |
| Emission layer | Exemplified Compound AA-1 (host) d-3 (guest) (host:guest = 95:5 (weight ratio)) | 30 |
| Hole-blocking layer | d-4 | 10 |
| Electron transport layer | d-5 | 30 |
| First electrode layer (cathode) | LiF | 0.5 |
| Second electrode layer (cathode) | Al | 150 |

A predetermined voltage was applied to the resultant organic light-emitting device while its ITO electrode was defined as a positive electrode and its Al electrode was defined as a negative electrode. As a result, the device was observed to emit blue light having CIE chromaticity coordinates of (0.21, 0.48).

Example 25

An organic light-emitting device was produced by the same method as that of Example 24 except that Exemplified Compound AA-20 was used instead of Exemplified Compound AA-1 in Example 24. The emission characteristics of the organic light-emitting device were measured and evaluated by the same method as that of Example 24. As a result, the device was observed to emit blue light having CIE chromaticity coordinates of (0.21, 0.48).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-077439, filed Apr. 3, 2013, and Japanese Patent Application No. 2014-076287, filed Apr. 2, 2014, which are hereby incorporated by reference herein in their entirety.

REFERENCE SIGNS LIST

17: TFT device, 20: anode, 21: organic compound layer, 22: cathode

The invention claimed is:

1. An organic compound having general formula [3]:

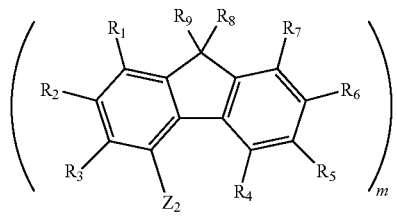

[3]

wherein, in the general formula [3], $Z_2$ represents a fluoren-4-yl group, a phenanthryl group, a triphenylenyl group, an aliphatic condensed polycyclic group, a carbon atom, or an oxygen atom, and when $Z_2$ represents a fluoren-4-yl group, a phenanthryl group, a triphenylenyl group, or an aliphatic condensed polycyclic group, $Z_2$ can be substituted with a substituent selected from the group consisting of an alkyl group, an alkoxy group, an aryl group, and a halogen atom, wherein, in the general formula [3], $R_1$ to $R_9$ each represent a hydrogen atom, an alkyl group, an alkoxy group, or a halogen atom, provided that at least two of substituents represented by $R_1$ to $R_9$ comprise alkyl groups, wherein, in the general formula [3], m represents an integer of from 1 to 6, provided that when $Z_2$ represents a carbon atom, m represents 4, and when $Z_2$ represents an oxygen atom, m represents 2, and when m represents 2 or more, structures in parentheses may be identical to or different from each other.

2. The organic compound according to claim 1, wherein $Z_2$ represents an aliphatic condensed polycyclic group, carbon atom, or oxygen atom and the aliphatic condensed polycyclic group can be substituted by a substituent selected from the group consisting of an alkyl group, an alkoxy group, an aryl group, and a halogen atom.

3. The organic compound according to claim 1, wherein the compound has general formula [5]:

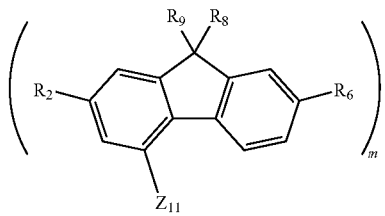

[5]

wherein, in the general formula [5], $Z_{11}$ represents a fluoren-4-yl group, a phenanthryl group, a triphenylenyl group, an aliphatic condensed polycyclic group, a carbon atom, or an oxygen atom, and when $Z_{11}$ represents a fluoren-4-yl group, a phenanthryl group, a triphenylenyl group, or an aliphatic condensed polycyclic group, $Z_{11}$ can be substituted by a substituent selected from the group consisting of an alkyl group, an alkoxy group, an aryl group, and a halogen atom, wherein, in the general formula [5], $R_2$, $R_6$, $R_8$, and $R_9$ each represent an alkyl group or an alkoxy group, and may be identical to or different from one another, wherein, in the general formula [5], m represents an integer of from 1 to 6, provided that when $Z_{11}$ represents a carbon atom, m represents 4, and when $Z_{11}$ represents an oxygen atom, m represents 2, and when m represents 2 or more, structures in parentheses may be identical to or different from each other.

4. The organic compound according to claim 3, wherein $Z_{11}$ represents an aliphatic condensed polycyclic group, carbon atom, or oxygen atom and the aliphatic condensed polycyclic group can be substituted with a substituent selected from the group consisting of an alkyl group, an alkoxy group, an aryl group, and a halogen atom.

5. The organic compound according to claim 3, wherein the compound has general formula [6]:

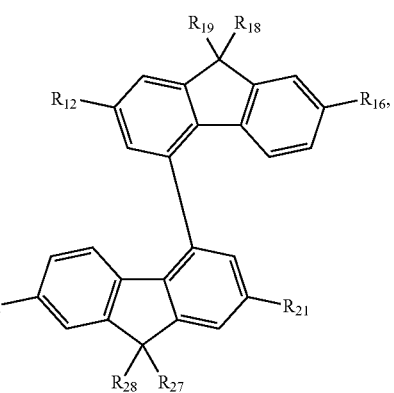

[6]

wherein, in the general formula [6], $R_{12}$, $R_{16}$, $R_{18}$, $R_{19}$, $R_{21}$, $R_{24}$, $R_{27}$, and $R_{28}$ each represent an alkyl group or an alkoxy group, and may be identical to or different from one another.

6. The organic compound according to claim 1, wherein the compound has $SP^2$ carbon atoms and $SP^3$ carbon atoms and has a ratio of the number of the $SP^3$ carbon atoms to the number of the $SP^2$ carbon atoms of 40% or more.

7. An organic light-emitting device comprising:
an anode;
a cathode;
an emission layer placed between the anode and the cathode; and
an organic compound layer placed between the anode and the emission layer, wherein the organic compound layer contains the organic compound according to claim 1.

8. An organic light-emitting device comprising:
an anode;
a cathode;
an emission layer placed between the anode and the cathode; and
an organic compound layer placed between the cathode and the emission layer,
wherein the organic compound layer contains the organic compound according to claim 1.

9. An organic light-emitting device comprising:
an anode;
a cathode; and
an emission layer placed between the anode and the cathode,
wherein the emission layer contains the organic compound according to claim 1.

10. A device comprising:
an anode;
a cathode;
an emission layer placed between the anode and the cathode; and
an organic compound layer placed between the anode and the emission layer,
wherein the organic compound layer contains compound A and compound B, compound A being an organic compound free of a nitrogen atom and a metal atom, the compound having $SP^2$ carbon atoms and $SP^3$ carbon atoms, and compound B being a compound having a tertiary amine structure,
wherein compound A has general formula [3]:

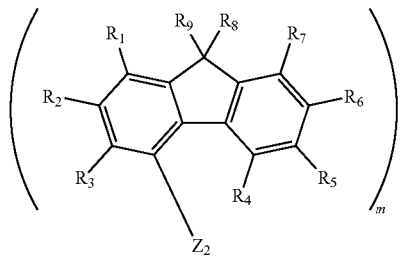

[3]

wherein, in the general formula [3], $Z_2$ represents a naphthyl group, a fluorenyl group, a phenanthryl group, a triphenylenyl group, an aliphatic condensed polycyclic group, a carbon atom, or an oxygen atom, and when $Z_2$ represents a naphthyl group, a fluorenyl group, a phenanthryl group, a triphenylenyl group, or an aliphatic condensed polycyclic group, $Z_2$ can be substituted with a substituent selected from the group consisting of an alkyl group, an alkoxy group, an aryl group, and a halogen atom,
wherein, in the general formula [3], $R_1$ to $R_9$ each represent a hydrogen atom, an alkyl group, an alkoxy group, or a halogen atom, provided that at least two of substituents represented by $R_1$ to $R_9$ comprise alkyl groups,
wherein, in the general formula [3], m represents an integer of from 1 to 6, provided that when $Z_2$ represents a carbon atom, m represents 4, and when $Z_2$ represents an oxygen atom, m represents 2, and when m represents 2 or more, structures in parentheses may be identical to or different from each other, and
with the proviso that $Z_2$, m and $R_1$-$R_9$ are selected so that compound A has a ratio of the number of the $SP^3$ carbon atoms to the number of the $SP^2$ carbon atoms of 40% or more.

11. The device according to claim 10, wherein the ratio of the number of the $SP^3$ carbon atoms of the compound A to the number of the $SP^2$ carbon atoms of the compound A is 80% or more.

12. The device according to claim 10, wherein a ratio of the compound B in the organic compound layer with reference to a total of the compound A and the compound B is from 10 wt % to 90 wt %.

13. The device according to claim 10, wherein a ratio of the compound B in the organic compound layer with reference to a total of the compound A and the compound B is from 20 wt % to 70 wt %.

14. The device according to claim 10, wherein compound A has general formula [5]:

[5]

wherein, in the general formula [5], $Z_{11}$ represents a naphthyl group, a fluorenyl group, a phenanthryl group, a triphenylenyl group, an aliphatic condensed polycyclic group, a carbon atom, or an oxygen atom, and when $Z_{11}$ represents a naphthyl group, a fluorenyl group, a phenanthryl group, a triphenylenyl group, or an aliphatic condensed polycyclic group, $Z_{11}$ may be substituted with a substituent selected from the group consisting of an alkyl group, an alkoxy group, an aryl group, and a halogen atom,
wherein, in the general formula [5], $R_2$, $R_6$, $R_8$, and $R_9$ each represent an alkyl group or an alkoxy group, and may be identical to or different from one another,
wherein, in the general formula [5], m represents an integer of from 1 to 6, provided that when $Z_{11}$ represents a carbon atom, m represents 4, and when $Z_{11}$ represents an oxygen atom, m represents 2, and when m represents 2 or more, structures in parentheses may be identical to or different from each other, and
with the proviso that $Z_{11}$, m, $R_2$, $R_6$, $R_8$, and $R_9$ are selected so that compound A has a ratio of the number of the $SP^3$ carbon atoms to the number of the $SP^2$ carbon atoms of 40% or more.

15. The device according to claim 14, wherein compound A has general formula [6]:

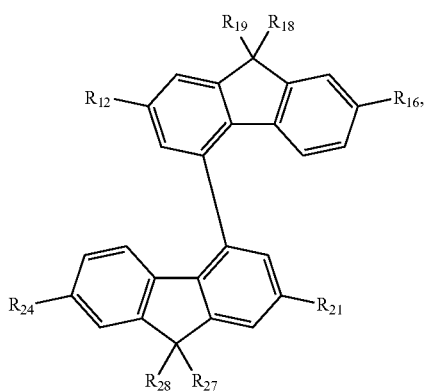

wherein, in the general formula [6], $R_{12}$, $R_{16}$, $R_{18}$, $R_{19}$, $R_{21}$, $R_{24}$, $R_{27}$, and $R_{28}$ each represent an alkyl group or an alkoxy group, and may be identical to or different from one another, with the proviso that $R_{12}$, $R_{16}$, $R_{18}$, $R_{19}$, $R_{21}$, $R_{24}$, $R_{27}$, and $R_{28}$ are selected so that compound A has a ratio of the number of the $SP^3$ carbon atoms to the number of the $SP^2$ carbon atoms of 40% or more.

16. A display apparatus comprising multiple pixels, at least one of the multiple pixels including the device according to claim 10, and an active device connected to the device.

17. A lighting apparatus comprising the device according to claim 10, and an AC/DC converter circuit for supplying a driving voltage to the device.

18. An image-forming apparatus comprising:
a photosensitive member;
a charging portion for charging a surface of the photosensitive member;
an exposure portion for exposing the photosensitive member; and
a developing unit for developing an electrostatic latent image formed on the surface of the photosensitive member,
wherein the exposure portion includes the device according to claim 10.

19. The device according to claim 10, wherein compound A has general formula [4]:

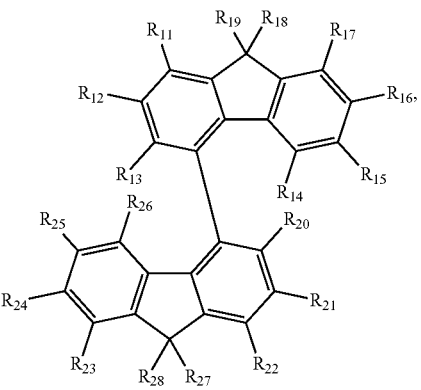

wherein, in the general formula [4], $R_{11}$ to $R_{28}$ each represent a hydrogen atom, an alkyl group, an alkoxy group, or a halogen atom, provided that at least two of substituents represented by $R_{11}$ to $R_{28}$ comprise alkyl groups, and
with the proviso that $R_{11}$-$R_{28}$ are selected so that compound A has a ratio of the number of the $SP^3$ carbon atoms to the number of the $SP^2$ carbon atoms of 40% or more.

20. The organic compound according to claim 1, wherein the compound has general formula [4]:

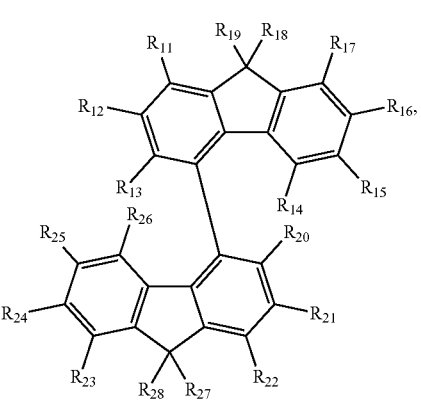

wherein, in the general formula [4], $R_{11}$ to $R_{28}$ each represent a hydrogen atom, an alkyl group, an alkoxy group, or a halogen atom, provided that at least two of substituents represented by $R_{11}$ to $R_{28}$ comprise alkyl groups.

* * * * *